US010870838B2

(12) United States Patent
Baunsgaard et al.

(10) Patent No.: US 10,870,838 B2
(45) Date of Patent: Dec. 22, 2020

(54) METHODS FOR PRODUCING LIPASES

(71) Applicant: NOVOZYMES A/S, Bagsvaerd (DK)

(72) Inventors: Lone Baunsgaard, Helsingør (DK);
Allan Svendsen, Hoersholm (DK); Kim Borch, Birkerød (DK); Rakhi Saikia, Bangalore (IN); Jakob Skjold-Jørgensen, København N (DK)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

(21) Appl. No.: 15/778,330

(22) PCT Filed: Nov. 30, 2016

(86) PCT No.: PCT/EP2016/079277
§ 371 (c)(1),
(2) Date: May 23, 2018

(87) PCT Pub. No.: WO2017/093318
PCT Pub. Date: Jun. 8, 2017

(65) Prior Publication Data
US 2018/0340159 A1 Nov. 29, 2018

(30) Foreign Application Priority Data

Dec. 1, 2015 (IN) .......................... 6448/CHE/2015
Jan. 28, 2016 (EP) ..................... 16153166

(51) Int. Cl.
*C12N 9/20* (2006.01)
*C11D 3/386* (2006.01)

(52) U.S. Cl.
CPC ............ *C12N 9/20* (2013.01); *C11D 3/38627* (2013.01); *C12Y 301/01003* (2013.01)

(58) Field of Classification Search
CPC ....................................................... C12N 9/20
USPC ....................................................... 435/198
See application file for complete search history.

(56) References Cited

U.S. PATENT DOCUMENTS 10,221,404 B2 * 3/2019 Reiser ....................... C12N 9/20
2019/0153410 A1 * 5/2019 Reiser ....................... C12N 9/20

FOREIGN PATENT DOCUMENTS

WO      2015/181118 A1    12/2015

OTHER PUBLICATIONS

Han et al, 2009, Appl Microbiol Biotechnol 85(1), 117-126.
Liu et al, 2013, Curr Microbiol 68(2), 186-191.
Yu et al, 2012, PLOS ONE 7(10), e 46388, Figure S1.
Yu et al, 2012, PLOS ONE 7(10), e46388.

* cited by examiner

*Primary Examiner* — Tekchand Saidha
(74) *Attorney, Agent, or Firm* — Elias Lambiris

(57) ABSTRACT

The present invention relates to a method for generating a preparation of a lipase variant of a parent lipase comprising a step of altering one or more nucleotides in a polynucleotide encoding the parent lipase, wherein the alteration provides at least one disulfide bond and a hydrolytic activity of said lipase variant which is reduced as compared with the hydrolytic activity of the parent lipase. The invention also relates to a polynucleotide encoding the lipase variant, the lipase variant and its use.

15 Claims, No Drawings
Specification includes a Sequence Listing.

SEQUENCE LISTING

```
<160> NUMBER OF SEQ ID NOS: 16

<210> SEQ ID NO 1
<211> LENGTH: 1110
<212> TYPE: DNA
<213> ORGANISM: Rhizomucor miehei
<220> FEATURE:
<221> NAME/KEY: CDS
<222> LOCATION: (13)..(1101)
<220> FEATURE:
<221> NAME/KEY: sig_peptide
<222> LOCATION: (13)..(84)
<220> FEATURE:
<221> NAME/KEY: misc_feature
<222> LOCATION: (85)..(294)
<220> FEATURE:
<221> NAME/KEY: mat_peptide
<222> LOCATION: (295)..(930)

<400> SEQUENCE: 1
ggatccttca cc atg gtt ctc aag cag cgt gca aac tac cta gga ttt ctg      51
              Met Val Leu Lys Gln Arg Ala Asn Tyr Leu Gly Phe Leu
                  -90                     -85 att gta ttc ttc acg gcc ttc ctg gtg gaa gcg gta ccc atc aag aga        99
Ile Val Phe Phe Thr Ala Phe Leu Val Glu Ala Val Pro Ile Lys Arg
    -80                 -75                 -70 caa tcg aat tcc acg gtc gac agt ctg ccg cct ctc atc ccc tcg aga       147
Gln Ser Asn Ser Thr Val Asp Ser Leu Pro Pro Leu Ile Pro Ser Arg
-65                 -60                 -55                 -50
```

```
acc tcg gca cct tca tca tca cca agc aca acc gac cct gaa gct cca      195
Thr Ser Ala Pro Ser Ser Ser Pro Ser Thr Thr Asp Pro Glu Ala Pro
            -45              -40             -35 gcc atg agt cgc aat gga ccg ctg ccc tcg gat gta gag act aaa tat      243
Ala Met Ser Arg Asn Gly Pro Leu Pro Ser Asp Val Glu Thr Lys Tyr
            -30              -25             -20 ggc atg gct ttg aat gct act tcc tat ccg gat tct gtg gtc caa gca      291
Gly Met Ala Leu Asn Ala Thr Ser Tyr Pro Asp Ser Val Val Gln Ala
            -15              -10             -5 atg agc att gat ggt ggt atc cgc gct gcg acc tcg caa gaa atc aat      339
Met Ser Ile Asp Gly Gly Ile Arg Ala Ala Thr Ser Gln Glu Ile Asn
-1  1                5                10              15 gaa ttg act tat tac act aca cta tct gcc aac tcg tac tgc cgc act      387
Glu Leu Thr Tyr Tyr Thr Thr Leu Ser Ala Asn Ser Tyr Cys Arg Thr
            20               25              30 gtc att cct gga gct acc tgg gac tgt atc cac tgt gat gca acg gag      435
Val Ile Pro Gly Ala Thr Trp Asp Cys Ile His Cys Asp Ala Thr Glu
            35               40              45 gat ctc aag att atc aag act tgg agc acg ctc atc tat gat aca aat      483
Asp Leu Lys Ile Ile Lys Thr Trp Ser Thr Leu Ile Tyr Asp Thr Asn
            50               55              60 gca atg gtt gca cgt ggt gac agc gaa aaa act atc tat atc gtt ttc      531
Ala Met Val Ala Arg Gly Asp Ser Glu Lys Thr Ile Tyr Ile Val Phe
            65               70              75 cga ggt tcg agc tct atc cgc aac tgg att gct gat ctc acc ttt gtg      579
Arg Gly Ser Ser Ser Ile Arg Asn Trp Ile Ala Asp Leu Thr Phe Val
80              85               90              95 cca gtt tca tat cct ccg gtc agt ggt aca aaa gta cac aag gga ttc      627
Pro Val Ser Tyr Pro Pro Val Ser Gly Thr Lys Val His Lys Gly Phe
                100              105             110 ctg gac agt tac ggg gaa gtt caa aac gag ctt gtt gct act gtt ctt      675
Leu Asp Ser Tyr Gly Glu Val Gln Asn Glu Leu Val Ala Thr Val Leu
            115              120             125 gat caa ttc aag caa tat cca agc tac aag gtt gct gtt aca ggt cac      723
Asp Gln Phe Lys Gln Tyr Pro Ser Tyr Lys Val Ala Val Thr Gly His
            130              135             140 tca ctc ggt ggt gct act gcg ttg ctt tgc gcc ctg gat ctc tat caa      771
Ser Leu Gly Gly Ala Thr Ala Leu Leu Cys Ala Leu Asp Leu Tyr Gln
    145              150             155 cga gaa gaa gga ctc tca tcc agc aac ttg ttc ctt tac act caa ggt      819
Arg Glu Glu Gly Leu Ser Ser Ser Asn Leu Phe Leu Tyr Thr Gln Gly
160              165             170             175 caa cca cgg gta ggc gac cct gcc ttt gcc aac tac gtt gtt agc acc      867
Gln Pro Arg Val Gly Asp Pro Ala Phe Ala Asn Tyr Val Val Ser Thr
            180              185             190 ggc att cct tac agg cgc acg gtc aat gaa cga gat atc gtt cct cat      915
Gly Ile Pro Tyr Arg Arg Thr Val Asn Glu Arg Asp Ile Val Pro His
            195              200             205 ctt cca cct gct gct ttt ggt ttt ctc cac gct ggc gag gag tat tgg      963
Leu Pro Pro Ala Ala Phe Gly Phe Leu His Ala Gly Glu Glu Tyr Trp
            210              215             220 att act gac aat agc cca gag act gtt cag gtc tgc aca agc gat ctg     1011
Ile Thr Asp Asn Ser Pro Glu Thr Val Gln Val Cys Thr Ser Asp Leu
            225              230             235 gaa acc tct gat tgc tct aac agc att gtt ccc ttc aca agt gtt ctt     1059
Glu Thr Ser Asp Cys Ser Asn Ser Ile Val Pro Phe Thr Ser Val Leu
240              245             250             255 gac cat ctc tcg tac ttt ggt atc aac aca ggc ctc tgt act taactcgag  1110
Asp His Leu Ser Tyr Phe Gly Ile Asn Thr Gly Leu Cys Thr
            260              265
```

<210> SEQ ID NO 2
<211> LENGTH: 363
<212> TYPE: PRT
<213> ORGANISM: Rhizomucor miehei

<400> SEQUENCE: 2

```
Met Val Leu Lys Gln Arg Ala Asn Tyr Leu Gly Phe Leu Ile Val Phe
             -90                 -85                 -80

Phe Thr Ala Phe Leu Val Glu Ala Val Pro Ile Lys Arg Gln Ser Asn
         -75                 -70                 -65

Ser Thr Val Asp Ser Leu Pro Pro Leu Ile Pro Ser Arg Thr Ser Ala
         -60                 -55                 -50

Pro Ser Ser Ser Pro Ser Thr Thr Asp Pro Glu Ala Pro Ala Met Ser
         -45                 -40                 -35

Arg Asn Gly Pro Leu Pro Ser Asp Val Glu Thr Lys Tyr Gly Met Ala
-30                 -25                 -20                 -15

Leu Asn Ala Thr Ser Tyr Pro Asp Ser Val Val Gln Ala Met Ser Ile
             -10                 -5                  -1   1

Asp Gly Gly Ile Arg Ala Ala Thr Ser Gln Glu Ile Asn Glu Leu Thr
             5                   10                  15

Tyr Tyr Thr Thr Leu Ser Ala Asn Ser Tyr Cys Arg Thr Val Ile Pro
             20                  25                  30

Gly Ala Thr Trp Asp Cys Ile His Cys Asp Ala Thr Glu Asp Leu Lys
35                  40                  45                  50

Ile Ile Lys Thr Trp Ser Thr Leu Ile Tyr Asp Thr Asn Ala Met Val
             55                  60                  65

Ala Arg Gly Asp Ser Glu Lys Thr Ile Tyr Ile Val Phe Arg Gly Ser
             70                  75                  80

Ser Ser Ile Arg Asn Trp Ile Ala Asp Leu Thr Phe Val Pro Val Ser
             85                  90                  95

Tyr Pro Pro Val Ser Gly Thr Lys Val His Lys Gly Phe Leu Asp Ser
             100                 105                 110

Tyr Gly Glu Val Gln Asn Glu Leu Val Ala Thr Val Leu Asp Gln Phe
115                 120                 125                 130

Lys Gln Tyr Pro Ser Tyr Lys Val Ala Val Thr Gly His Ser Leu Gly
             135                 140                 145

Gly Ala Thr Ala Leu Leu Cys Ala Leu Asp Leu Tyr Gln Arg Glu Glu
             150                 155                 160

Gly Leu Ser Ser Ser Asn Leu Phe Leu Tyr Thr Gln Gly Gln Pro Arg
             165                 170                 175

Val Gly Asp Pro Ala Phe Ala Asn Tyr Val Val Ser Thr Gly Ile Pro
             180                 185                 190

Tyr Arg Arg Thr Val Asn Glu Arg Asp Ile Val Pro His Leu Pro Pro
195                 200                 205                 210

Ala Ala Phe Gly Phe Leu His Ala Gly Glu Glu Tyr Trp Ile Thr Asp
             215                 220                 225

Asn Ser Pro Glu Thr Val Gln Val Cys Thr Ser Asp Leu Glu Thr Ser
             230                 235                 240

Asp Cys Ser Asn Ser Ile Val Pro Phe Thr Ser Val Leu Asp His Leu
             245                 250                 255

Ser Tyr Phe Gly Ile Asn Thr Gly Leu Cys Thr
             260                 265
```

```
<210> SEQ ID NO 3
<211> LENGTH: 269
<212> TYPE: PRT
<213> ORGANISM: Rhizomucor miehei

<400> SEQUENCE: 3

Ser Ile Asp Gly Gly Ile Arg Ala Ala Thr Ser Gln Glu Ile Asn Glu
1               5                   10                  15

Leu Thr Tyr Tyr Thr Thr Leu Ser Ala Asn Ser Tyr Cys Arg Thr Val
            20                  25                  30

Ile Pro Gly Ala Thr Trp Asp Cys Ile His Cys Asp Ala Thr Glu Asp
        35                  40                  45

Leu Lys Ile Ile Lys Thr Trp Ser Thr Leu Ile Tyr Asp Thr Asn Ala
50                  55                  60

Met Val Ala Arg Gly Asp Ser Glu Lys Thr Ile Tyr Ile Val Phe Arg
65                  70                  75                  80

Gly Ser Ser Ser Ile Arg Asn Trp Ile Ala Asp Leu Thr Phe Val Pro
                85                  90                  95

Val Ser Tyr Pro Pro Val Ser Gly Thr Lys Val His Lys Gly Phe Leu
            100                 105                 110

Asp Ser Tyr Gly Glu Val Gln Asn Glu Leu Val Ala Thr Val Leu Asp
        115                 120                 125

Gln Phe Lys Gln Tyr Pro Ser Tyr Lys Val Ala Val Thr Gly His Ser
130                 135                 140

Leu Gly Gly Ala Thr Ala Leu Leu Cys Ala Leu Asp Leu Tyr Gln Arg
145                 150                 155                 160

Glu Glu Gly Leu Ser Ser Ser Asn Leu Phe Leu Tyr Thr Gln Gly Gln
                165                 170                 175

Pro Arg Val Gly Asp Pro Ala Phe Ala Asn Tyr Val Val Ser Thr Gly
            180                 185                 190

Ile Pro Tyr Arg Arg Thr Val Asn Glu Arg Asp Ile Val Pro His Leu
        195                 200                 205

Pro Pro Ala Ala Phe Gly Phe Leu His Ala Gly Glu Glu Tyr Trp Ile
210                 215                 220

Thr Asp Asn Ser Pro Glu Thr Val Gln Val Cys Thr Ser Asp Leu Glu
225                 230                 235                 240

Thr Ser Asp Cys Ser Asn Ser Ile Val Pro Phe Thr Ser Val Leu Asp
                245                 250                 255

His Leu Ser Tyr Phe Gly Ile Asn Thr Gly Leu Cys Thr
            260                 265

<210> SEQ ID NO 4
<211> LENGTH: 70
<212> TYPE: PRT
<213> ORGANISM: Rhizomucor miehei

<400> SEQUENCE: 4

Val Pro Ile Lys Arg Gln Ser Asn Ser Thr Val Asp Ser Leu Pro Pro
1               5                   10                  15

Leu Ile Pro Ser Arg Thr Ser Ala Pro Ser Ser Pro Ser Thr Thr
            20                  25                  30

Asp Pro Glu Ala Pro Ala Met Ser Arg Asn Gly Pro Leu Pro Ser Asp
        35                  40                  45

Val Glu Thr Lys Tyr Gly Met Ala Leu Asn Ala Thr Ser Tyr Pro Asp
50                  55                  60

Ser Val Val Gln Ala Met
```

-continued

```
<210> SEQ ID NO 5
<211> LENGTH: 876
<212> TYPE: DNA
<213> ORGANISM: Thermomyces lanuginosus
<220> FEATURE:
<221> NAME/KEY: CDS
<222> LOCATION: (1)..(873)
<220> FEATURE:
<221> NAME/KEY: sig_peptide
<222> LOCATION: (1)..(51)
<220> FEATURE:
<221> NAME/KEY: misc_feature
<222> LOCATION: (52)..(66)
<220> FEATURE:
<221> NAME/KEY: mat_peptide
<222> LOCATION: (67)..(873)

<400> SEQUENCE: 5
```

| | | | | | | | | | | | | | | | | |
|---|---|---|---|---|---|---|---|---|---|---|---|---|---|---|---|---|
| atg | agg | agc | tcc | ctt | gtg | ctg | ttc | ttt | gtc | tct | gcg | tgg | acg | gcc | ttg | 48 |
| Met | Arg | Ser | Ser | Leu | Val | Leu | Phe | Phe | Val | Ser | Ala | Trp | Thr | Ala | Leu | |
| | | | -20 | | | | -15 | | | | -10 | | | | | |
| gcc | agt | cct | att | cgt | cga | gag | gtc | tcg | cag | gat | ctg | ttt | aac | cag | ttc | 96 |
| Ala | Ser | Pro | Ile | Arg | Arg | Glu | Val | Ser | Gln | Asp | Leu | Phe | Asn | Gln | Phe | |
| | -5 | | | | -1 | 1 | | | 5 | | | | | 10 | | |
| aat | ctc | ttt | gca | cag | tat | tct | gca | gcc | gca | tac | tgc | gga | aaa | aac | aat | 144 |
| Asn | Leu | Phe | Ala | Gln | Tyr | Ser | Ala | Ala | Ala | Tyr | Cys | Gly | Lys | Asn | Asn | |
| | | | | 15 | | | | | 20 | | | | | 25 | | |
| gat | gcc | cca | gct | ggt | aca | aac | att | acg | tgc | acg | gga | aat | gcc | tgc | ccc | 192 |
| Asp | Ala | Pro | Ala | Gly | Thr | Asn | Ile | Thr | Cys | Thr | Gly | Asn | Ala | Cys | Pro | |
| | | | 30 | | | | | 35 | | | | | 40 | | | |
| gag | gta | gag | aag | gcg | gat | gca | acg | ttt | ctc | tac | tcg | ttt | gaa | gac | tct | 240 |
| Glu | Val | Glu | Lys | Ala | Asp | Ala | Thr | Phe | Leu | Tyr | Ser | Phe | Glu | Asp | Ser | |
| | | 45 | | | | | 50 | | | | | 55 | | | | |
| gga | gtg | ggc | gat | gtc | acc | ggc | ttc | ctt | gct | ctc | gac | aac | acg | aac | aaa | 288 |
| Gly | Val | Gly | Asp | Val | Thr | Gly | Phe | Leu | Ala | Leu | Asp | Asn | Thr | Asn | Lys | |
| | 60 | | | | | 65 | | | | | 70 | | | | | |
| ttg | atc | gtc | ctc | tct | ttc | cgt | ggc | tct | cgt | tcc | ata | gag | aac | tgg | atc | 336 |
| Leu | Ile | Val | Leu | Ser | Phe | Arg | Gly | Ser | Arg | Ser | Ile | Glu | Asn | Trp | Ile | |
| 75 | | | | | 80 | | | | | 85 | | | | | 90 | |
| ggg | aat | ctt | aac | ttc | gac | ttg | aaa | gaa | ata | aat | gac | att | tgc | tcc | ggc | 384 |
| Gly | Asn | Leu | Asn | Phe | Asp | Leu | Lys | Glu | Ile | Asn | Asp | Ile | Cys | Ser | Gly | |
| | | | | 95 | | | | | 100 | | | | | 105 | | |
| tgc | agg | gga | cat | gac | ggc | ttc | act | tcg | tcc | tgg | agg | tct | gta | gcc | gat | 432 |
| Cys | Arg | Gly | His | Asp | Gly | Phe | Thr | Ser | Ser | Trp | Arg | Ser | Val | Ala | Asp | |
| | | | 110 | | | | | 115 | | | | | 120 | | | |
| acg | tta | agg | cag | aag | gtg | gag | gat | gct | gtg | agg | gag | cat | ccc | gac | tat | 480 |
| Thr | Leu | Arg | Gln | Lys | Val | Glu | Asp | Ala | Val | Arg | Glu | His | Pro | Asp | Tyr | |
| | | 125 | | | | | 130 | | | | | 135 | | | | |
| cgc | gtg | gtg | ttt | acc | gga | cat | agc | ttg | ggt | ggt | gca | ttg | gca | act | gtt | 528 |
| Arg | Val | Val | Phe | Thr | Gly | His | Ser | Leu | Gly | Gly | Ala | Leu | Ala | Thr | Val | |
| | 140 | | | | | 145 | | | | | 150 | | | | | |
| gcc | gga | gca | gac | ctg | cgt | gga | aat | ggg | tat | gat | atc | gac | gtg | ttt | tca | 576 |
| Ala | Gly | Ala | Asp | Leu | Arg | Gly | Asn | Gly | Tyr | Asp | Ile | Asp | Val | Phe | Ser | |
| 155 | | | | | 160 | | | | | 165 | | | | | 170 | |
| tat | ggc | gcc | ccc | cga | gtc | gga | aac | agg | gct | ttt | gca | gaa | ttc | ctg | acc | 624 |
| Tyr | Gly | Ala | Pro | Arg | Val | Gly | Asn | Arg | Ala | Phe | Ala | Glu | Phe | Leu | Thr | |
| | | | | 175 | | | | | 180 | | | | | 185 | | |
| gta | cag | acc | ggc | gga | aca | ctc | tac | cgc | att | acc | cac | acc | aat | gat | att | 672 |
| Val | Gln | Thr | Gly | Gly | Thr | Leu | Tyr | Arg | Ile | Thr | His | Thr | Asn | Asp | Ile | |
| | | | | 190 | | | | | 195 | | | | | 200 | | |
| gtc | cct | aga | ctc | ccg | ccg | cgc | gaa | ttc | ggt | tac | agc | cat | tct | agc | cca | 720 |

```
Val Pro Arg Leu Pro Pro Arg Glu Phe Gly Tyr Ser His Ser Ser Pro
        205                 210                 215 gag tac tgg atc aaa tct gga acc ctt gtc ccc gtc acc cga aac gat      768
Glu Tyr Trp Ile Lys Ser Gly Thr Leu Val Pro Val Thr Arg Asn Asp
        220                 225                 230 atc gtg aag ata gaa ggc atc gat gcc acc ggc ggc aat aac cag cct      816
Ile Val Lys Ile Glu Gly Ile Asp Ala Thr Gly Gly Asn Asn Gln Pro
235                 240                 245                 250 aac att ccg gat atc cct gcg cac cta tgg tac ttc ggg tta att ggg      864
Asn Ile Pro Asp Ile Pro Ala His Leu Trp Tyr Phe Gly Leu Ile Gly
                255                 260                 265 aca tgt ctt tag                                                      876
Thr Cys Leu <210> SEQ ID NO 6
<211> LENGTH: 291
<212> TYPE: PRT
<213> ORGANISM: Thermomyces lanuginosus

<400> SEQUENCE: 6

Met Arg Ser Ser Leu Val Leu Phe Phe Val Ser Ala Trp Thr Ala Leu
            -20                 -15                 -10

Ala Ser Pro Ile Arg Arg Glu Val Ser Gln Asp Leu Phe Asn Gln Phe
         -5             -1   1               5                  10

Asn Leu Phe Ala Gln Tyr Ser Ala Ala Tyr Cys Gly Lys Asn Asn
                 15                  20                  25

Asp Ala Pro Ala Gly Thr Asn Ile Thr Cys Thr Gly Asn Ala Cys Pro
                 30                  35                  40

Glu Val Glu Lys Ala Asp Ala Thr Phe Leu Tyr Ser Phe Glu Asp Ser
                 45                  50                  55

Gly Val Gly Asp Val Thr Gly Phe Leu Ala Leu Asp Asn Thr Asn Lys
                 60                  65                  70

Leu Ile Val Leu Ser Phe Arg Gly Ser Arg Ser Ile Glu Asn Trp Ile
 75                  80                  85                  90

Gly Asn Leu Asn Phe Asp Leu Lys Glu Ile Asn Asp Ile Cys Ser Gly
                 95                 100                 105

Cys Arg Gly His Asp Gly Phe Thr Ser Ser Trp Arg Ser Val Ala Asp
                110                 115                 120

Thr Leu Arg Gln Lys Val Glu Asp Ala Val Arg Glu His Pro Asp Tyr
                125                 130                 135

Arg Val Val Phe Thr Gly His Ser Leu Gly Gly Ala Leu Ala Thr Val
                140                 145                 150

Ala Gly Ala Asp Leu Arg Gly Asn Gly Tyr Asp Ile Asp Val Phe Ser
155                 160                 165                 170

Tyr Gly Ala Pro Arg Val Gly Asn Arg Ala Phe Ala Glu Phe Leu Thr
                175                 180                 185

Val Gln Thr Gly Gly Thr Leu Tyr Arg Ile Thr His Thr Asn Asp Ile
                190                 195                 200

Val Pro Arg Leu Pro Pro Arg Glu Phe Gly Tyr Ser His Ser Ser Pro
                205                 210                 215

Glu Tyr Trp Ile Lys Ser Gly Thr Leu Val Pro Val Thr Arg Asn Asp
                220                 225                 230

Ile Val Lys Ile Glu Gly Ile Asp Ala Thr Gly Gly Asn Asn Gln Pro
235                 240                 245                 250

Asn Ile Pro Asp Ile Pro Ala His Leu Trp Tyr Phe Gly Leu Ile Gly
                255                 260                 265
```

Thr Cys Leu

<210> SEQ ID NO 7
<211> LENGTH: 269
<212> TYPE: PRT
<213> ORGANISM: Thermomyces lanuginosus

<400> SEQUENCE: 7

```
Glu Val Ser Gln Asp Leu Phe Asn Gln Phe Asn Leu Phe Ala Gln Tyr
1               5                   10                  15

Ser Ala Ala Ala Tyr Cys Gly Lys Asn Asn Asp Ala Pro Ala Gly Thr
            20                  25                  30

Asn Ile Thr Cys Thr Gly Asn Ala Cys Pro Glu Val Glu Lys Ala Asp
        35                  40                  45

Ala Thr Phe Leu Tyr Ser Phe Glu Asp Ser Gly Val Gly Asp Val Thr
    50                  55                  60

Gly Phe Leu Ala Leu Asp Asn Thr Asn Lys Leu Ile Val Leu Ser Phe
65                  70                  75                  80

Arg Gly Ser Arg Ser Ile Glu Asn Trp Ile Gly Asn Leu Asn Phe Asp
                85                  90                  95

Leu Lys Glu Ile Asn Asp Ile Cys Ser Gly Cys Arg Gly His Asp Gly
            100                 105                 110

Phe Thr Ser Ser Trp Arg Ser Val Ala Asp Thr Leu Arg Gln Lys Val
        115                 120                 125

Glu Asp Ala Val Arg Glu His Pro Asp Tyr Arg Val Val Phe Thr Gly
    130                 135                 140

His Ser Leu Gly Gly Ala Leu Ala Thr Val Ala Gly Ala Asp Leu Arg
145                 150                 155                 160

Gly Asn Gly Tyr Asp Ile Asp Val Phe Ser Tyr Gly Ala Pro Arg Val
                165                 170                 175

Gly Asn Arg Ala Phe Ala Glu Phe Leu Thr Val Gln Thr Gly Gly Thr
            180                 185                 190

Leu Tyr Arg Ile Thr His Thr Asn Asp Ile Val Pro Arg Leu Pro Pro
        195                 200                 205

Arg Glu Phe Gly Tyr Ser His Ser Ser Pro Glu Tyr Trp Ile Lys Ser
    210                 215                 220

Gly Thr Leu Val Pro Val Thr Arg Asn Asp Ile Val Lys Ile Glu Gly
225                 230                 235                 240

Ile Asp Ala Thr Gly Gly Asn Asn Gln Pro Asn Ile Pro Asp Ile Pro
                245                 250                 255

Ala His Leu Trp Tyr Phe Gly Leu Ile Gly Thr Cys Leu
            260                 265
```

<210> SEQ ID NO 8
<211> LENGTH: 338
<212> TYPE: PRT
<213> ORGANISM: Absidia sp

<400> SEQUENCE: 8

```
Met His Ser His Phe Val Val Leu Leu Leu Ala Val Phe Ile Cys Met
1               5                   10                  15

Cys Ser Val Ser Gly Val Pro Leu Gln Ile Asp Pro Arg Asp Asp Lys
            20                  25                  30

Ser Tyr Val Pro Glu Gln Tyr Pro Leu Lys Val Asn Gly Pro Leu Pro
        35                  40                  45
```

```
Glu Gly Val Ser Val Ile Gln Gly Tyr Cys Glu Asn Cys Thr Met Tyr
 50                  55                  60

Pro Glu Glu Asn Ser Val Ser Ala Phe Ser Ser Ser Thr Gln Asp
 65                  70                  75                  80

Tyr Arg Ile Ala Ser Glu Ala Glu Ile Lys Ala His Thr Phe Tyr Thr
                 85                  90                  95

Ala Leu Ser Ala Asn Ala Tyr Cys Arg Thr Val Ile Pro Gly Gly Arg
            100                 105                 110

Trp Ser Cys Pro His Cys Gly Val Ala Ser Asn Leu Gln Ile Thr Lys
        115                 120                 125

Thr Phe Ser Thr Leu Ile Thr Asp Thr Asn Val Leu Ala Val Gly
130                 135                 140

Glu Lys Glu Lys Thr Ile Tyr Val Val Phe Arg Gly Thr Ser Ser Ile
145                 150                 155                 160

Arg Asn Ala Ile Ala Asp Ile Val Phe Val Pro Val Asn Tyr Pro Pro
                165                 170                 175

Val Asn Gly Ala Lys Val His Lys Gly Phe Leu Asp Ser Tyr Asn Glu
            180                 185                 190

Val Gln Asp Lys Leu Val Ala Glu Val Lys Ala Gln Leu Asp Arg His
        195                 200                 205

Pro Gly Tyr Lys Ile Val Val Thr Gly His Ser Leu Gly Gly Ala Thr
210                 215                 220

Ala Val Leu Ser Ala Leu Asp Leu Tyr His His Gly His Ala Asn Ile
225                 230                 235                 240

Glu Ile Tyr Thr Gln Gly Gln Pro Arg Ile Gly Thr Pro Ala Phe Ala
                245                 250                 255

Asn Tyr Val Ile Gly Thr Lys Ile Pro Tyr Gln Arg Leu Val His Glu
            260                 265                 270

Arg Asp Ile Val Pro His Leu Pro Pro Gly Ala Phe Gly Phe Leu His
        275                 280                 285

Ala Gly Glu Glu Phe Trp Ile Met Lys Asp Ser Ser Leu Arg Val Cys
290                 295                 300

Pro Asn Gly Ile Glu Thr Asp Asn Cys Ser Asn Ser Ile Val Pro Phe
305                 310                 315                 320

Thr Ser Val Ile Asp His Leu Ser Tyr Leu Asp Met Asn Thr Gly Leu
                325                 330                 335

Cys Leu

<210> SEQ ID NO 9
<211> LENGTH: 389
<212> TYPE: PRT
<213> ORGANISM: Rhizopus microsporus var. chinensis

<400> SEQUENCE: 9

Met Val Ser Phe Ile Ser Ile Ser Gln Gly Val Ser Leu Cys Leu Leu
  1               5                  10                  15

Val Ser Ser Met Met Leu Gly Ser Ser Ala Val Pro Val Ala Gly His
             20                  25                  30

Lys Gly Ser Val Lys Ala Thr Asn Gly Thr Asp Phe Gln Leu Pro Pro
         35                  40                  45

Leu Ile Ser Ser Arg Cys Thr Pro Pro Ser His Pro Glu Thr Thr Gly
     50                  55                  60

Asp Pro Asp Ala Glu Ala Tyr Tyr Ile Asn Lys Ser Val Gln Trp Tyr
 65                  70                  75                  80
```

```
Gln Ala His Gly Gly Asn Tyr Thr Ala Leu Ile Lys Arg Asp Thr Glu
                85                  90                  95

Thr Val Gly Gly Met Thr Leu Asp Leu Pro Glu Asn Pro Pro Pro Ile
            100                 105                 110

Pro Ala Thr Ser Thr Ala Pro Ser Ser Asp Ser Gly Glu Val Val Thr
        115                 120                 125

Ala Thr Ala Ala Gln Ile Lys Glu Leu Thr Asn Tyr Ala Gly Val Ala
    130                 135                 140

Ala Thr Ala Tyr Cys Arg Ser Val Val Pro Gly Thr Lys Trp Asp Cys
145                 150                 155                 160

Lys Gln Cys Leu Lys Tyr Val Pro Asp Gly Lys Leu Ile Lys Thr Phe
                165                 170                 175

Thr Ser Leu Leu Thr Asp Thr Asn Gly Phe Ile Leu Arg Ser Asp Ala
            180                 185                 190

Gln Lys Thr Ile Tyr Val Thr Phe Arg Gly Thr Asn Ser Phe Arg Ser
        195                 200                 205

Ala Ile Thr Asp Met Val Phe Thr Phe Thr Asp Tyr Ser Pro Val Lys
    210                 215                 220

Gly Ala Lys Val His Ala Gly Phe Leu Ser Ser Tyr Asn Gln Val Val
225                 230                 235                 240

Lys Asp Tyr Phe Pro Val Val Gln Asp Gln Leu Thr Ala Tyr Pro Asp
                245                 250                 255

Tyr Lys Val Ile Val Thr Gly His Ser Leu Gly Gly Ala Gln Ala Leu
            260                 265                 270

Leu Ala Gly Met Asp Leu Tyr Gln Arg Glu Lys Arg Leu Ser Pro Lys
        275                 280                 285

Asn Leu Ser Ile Tyr Thr Val Gly Cys Pro Arg Val Gly Asn Asn Ala
    290                 295                 300

Phe Ala Tyr Tyr Val Asp Ser Thr Gly Ile Pro Phe His Arg Thr Val
305                 310                 315                 320

His Lys Arg Asp Ile Val Pro His Val Pro Pro Gln Ala Phe Gly Tyr
                325                 330                 335

Leu His Pro Gly Val Glu Ser Trp Ile Lys Glu Asp Pro Ala Asp Val
            340                 345                 350

Gln Ile Cys Thr Ser Asn Ile Glu Thr Lys Gln Cys Ser Asn Ser Ile
        355                 360                 365

Val Pro Phe Thr Ser Ile Ala Asp His Leu Thr Tyr Phe Gly Ile Asn
    370                 375                 380

Glu Gly Ser Cys Leu
385

<210> SEQ ID NO 10
<211> LENGTH: 363
<212> TYPE: PRT
<213> ORGANISM: Phycomyces nitens

<400> SEQUENCE: 10

Met Lys Phe Thr Pro Leu Ser Val Val Ala Ile Ala Met Leu Phe Val
1               5                   10                  15

Ser Ser Pro Val Ser Met Ala Ala Pro Ala Thr Glu Asn Thr Leu Asn
            20                  25                  30

Thr Thr Val Thr Gln Pro Phe Thr Leu Pro Ala Ile Leu Ala Gly Arg
        35                  40                  45

Thr Ser Val Pro Lys Asn Leu Pro Asp Val Asn Leu Ser Ala Glu Lys
    50                  55                  60
```

```
Thr Ala Ile Lys Thr Asn Gly Pro Leu Pro Ala Asn Val Glu Gln Lys
 65                  70                  75                  80

Gly Gly Met Gly Leu Asn Ser Thr Thr Ile Asp Phe Ser Ala Ser Gly
                 85                  90                  95

Ser Gly Val Ser Arg Arg Ala Asp Val Tyr Ala Thr Ala Lys Val
            100                 105                 110

Gln Glu Leu Lys Leu Tyr Thr Gln Leu Ala Ala Asn Ala Tyr Cys Arg
            115                 120                 125

Ala Val Val Pro Gly Asn Lys Trp Asn Cys Lys His Cys Ser Gln Asp
130                 135                 140

Asp Ile Leu Val Ser Thr Phe Asp Ser Ser Lys Tyr Asp Thr Asn Gly
145                 150                 155                 160

Tyr Val Ala Arg Asn Asp Lys Ser Lys Val Ile Asn Leu Val Phe Arg
                165                 170                 175

Gly Thr Ser Ser Leu Pro Asn Phe Val Ala Asp Phe Glu Phe Ile Ala
            180                 185                 190

Gln Thr Tyr Pro Pro Val Ser Gly Ala Lys Val His Thr Gly Phe Tyr
            195                 200                 205

Lys Ala Tyr Met Glu Val Gln Lys Asp Val Val Ser Ser Met Ile Glu
210                 215                 220

Gln Ile Thr Ala Tyr Pro Asn Tyr Gln Val Val Ser Gly His Ser
225                 230                 235                 240

Leu Gly Gly Ala Leu Ala Thr Ile Gly Ala Leu Asp Leu Tyr Gln Arg
                245                 250                 255

Asp Thr Arg Phe Asn Ala Lys Asn Leu Ala Ile Arg Thr Tyr Gly Gly
            260                 265                 270

Pro Arg Val Gly Asn Pro Thr Phe Ala Tyr Tyr Val Thr Gly Thr Gly
            275                 280                 285

Ile Asp Leu Glu Arg Thr Val Asp Arg Gln Asp Ile Val Pro His Leu
290                 295                 300

Pro Pro Gln Ser Phe Gly Phe Leu His Pro Gly Val Glu Tyr Trp Ile
305                 310                 315                 320

Arg Glu Gly Asp Asn Val Lys Ile Cys Asp Val Leu Asp Ser Ser
                325                 330                 335

Glu Cys Ser Asn Ser Ile Val Pro Phe Thr Lys Leu Ser Asp His Leu
            340                 345                 350

Ser Tyr Phe Asp Ile Asn Thr Gly Leu Cys Leu
            355                 360

<210> SEQ ID NO 11
<211> LENGTH: 395
<212> TYPE: PRT
<213> ORGANISM: Mucor circinelloides

<400> SEQUENCE: 11

Met Val Leu Ile Ser Ser Leu Thr Lys Asp Val Lys Phe Val Leu Ala
1               5                   10                  15

Ala Ser Tyr Val Leu Phe Ala Ala Val Ser Asp Ala Ala Pro Thr Ser
            20                  25                  30

Ile Pro Leu Ile Glu Arg Ser Ser Ala Ser Ser Gly Asn Val Thr His
            35                  40                  45

Val Asn Gly Thr Leu Thr Asp Ala Asp Val Thr Leu Pro Pro Leu Ile
 50                  55                  60

Pro Lys Arg Val Ile Pro Ala Thr Lys Val Pro His Asp Tyr Asp Val
```

```
                65                  70                  75                  80
        Glu Ser Asp Tyr Ile Val Lys Asn Thr Glu Trp Tyr Asn Glu His Gly
                            85                  90                  95

Gly Asn Tyr Thr Leu Thr Lys Arg Asp Glu Ile Glu Thr Val Gly Asn
                            100                 105                 110

Phe Thr Met Asp Leu Pro Pro Asn Pro Pro Leu Pro Ala Tyr Pro
                        115                 120                 125

Lys Asp Val Leu Val Lys Ala Asp Thr Asn Lys Ile Lys Glu Leu
                    130                 135                 140

Thr Lys Tyr Ala Gly Ile Ala Ala Ala Tyr Cys Arg Asp Val Val
        145                 150                 155                 160

Pro Ala Asn Asn Trp Lys Cys Lys Gln Cys Leu Lys Gln Val Pro Asp
                            165                 170                 175

Gly Lys Leu Ile Lys Thr Phe Thr Ser Phe Ile Ser Asp Thr Asn Gly
                            180                 185                 190

Phe Val Leu Arg Ser Asp Lys Glu Lys Val Ile Tyr Leu Val Phe Arg
                        195                 200                 205

Gly Thr Asn Ser Ile Arg Ser Ser Ile Ala Asp Ile Gln Phe Asp Phe
                    210                 215                 220

Thr Asn Tyr Pro Asn Val Lys Gly Ala Lys Val His Arg Gly Phe Leu
        225                 230                 235                 240

Asn Ser Tyr Asn Glu Val Val Arg Ser Phe Phe Pro Asp Ile Gln Asp
                            245                 250                 255

Gln Ile Thr Ala Phe Pro Ser Tyr Lys Val Ile Val Thr Gly His Ser
                        260                 265                 270

Leu Gly Gly Ala Gln Ala Leu Leu Ala Gly Met Asp Leu Tyr Gln Arg
                    275                 280                 285

Asp Ser Arg Leu Ser Ala Lys Asn Leu Ala Ile Tyr Thr Val Gly Met
        290                 295                 300

Pro Arg Thr Gly Asn Ala Ala Phe Ala Tyr Tyr Val Asp Ser Thr Gly
        305                 310                 315                 320

Ile Pro Leu Ser Arg Ser Val Asn Glu Arg Asp Ile Val Pro His Val
                        325                 330                 335

Pro Pro Gln Ala Phe Gly Tyr Leu His Pro Gly Val Glu Ala Trp Thr
                        340                 345                 350

Arg Ser Ser Gly Asn Val Gln Ile Cys Thr Glu Asn Ile Glu Ser Asp
                    355                 360                 365

Leu Cys Ser Asn Thr Ile Val Pro Phe Thr Ser Ile Thr Asp His Leu
            370                 375                 380

Ser Tyr Tyr Asp Ile Asn Glu Gly Leu Cys Leu
        385                 390                 395

<210> SEQ ID NO 12
<211> LENGTH: 384
<212> TYPE: PRT
<213> ORGANISM: Mucor circinelloides

<400> SEQUENCE: 12

Met Val Ser Phe Val Ser Ile Ser Gln Gly Ile Ser Leu Phe Ile Val
1               5                   10                  15

Val Ser Ser Met Leu Thr Gly Ser Ala His Ala Ala Pro Ala Ser Ser
                20                  25                  30

His Ser Asn Ser Ser Lys Asn Ala Thr Thr Ser Asp Ala Ser Thr Phe
            35                  40                  45
```

```
Thr Leu Pro Pro Ile Ile Ser Ser Arg Val Thr Pro Pro Lys Val Pro
     50                  55                  60

Ser Gly Ser His Asn Val Glu Asp Ala Asn Val Ala Lys Asn Lys Lys
 65                  70                  75                  80

Trp Phe Glu Ala His Gly Gly Lys Leu Asn Val Thr Lys Arg Ala Asp
                 85                  90                  95

Glu Thr Val Gly Gly Tyr Thr Met Asp Leu Pro Ser Asn Ala Pro Pro
            100                 105                 110

Leu Pro Ala Val Pro Ser Thr Ser Thr Val Val Ile Ala Ser Thr Ala
        115                 120                 125

Gln Ile Ser Glu Phe Lys Lys Tyr Ala Gly Ile Ala Ser Thr Ala Tyr
130                 135                 140

Cys Arg Ser Val Val Pro Leu Asn Gln Trp Ser Cys Thr Asn Cys Leu
145                 150                 155                 160

Lys Phe Val Pro Asp Gly Lys Leu Ile Lys Thr Phe Thr Ser Leu Val
                165                 170                 175

Thr Asp Thr Asn Gly Phe Val Leu Arg Ser Asp Ala Gln Lys Thr Ile
            180                 185                 190

Tyr Val Val Phe Arg Gly Thr Asn Ser Ile Arg Ser Ala Ile Thr Asp
        195                 200                 205

Leu Val Phe Glu Leu Thr Asn Tyr Thr Pro Val Ser Gly Ala Lys Val
210                 215                 220

His Thr Gly Phe Tyr Ala Ser Tyr Lys Ala Val Val Ser Asp Tyr Phe
225                 230                 235                 240

Pro Ala Val Gln Ser Gln Leu Thr Ala Tyr Pro Gly Tyr Lys Val Ile
                245                 250                 255

Val Thr Gly His Ser Leu Gly Gly Ala Gln Ala Leu Leu Ala Gly Met
            260                 265                 270

Asp Leu Tyr Gln Arg Glu Pro Arg Leu Ser Lys Ser Asn Leu Ala Ile
        275                 280                 285

Tyr Thr Val Gly Cys Pro Arg Val Gly Asn Pro Ala Phe Ala Tyr Tyr
290                 295                 300

Val Asp Ser Thr Gly Ile Thr Phe Ser Arg Ser Val Asn Asn Arg Asp
305                 310                 315                 320

Ile Val Pro His Val Pro Pro Gln Ala Trp Gly Phe Leu His Pro Gly
                325                 330                 335

Val Glu Ala Trp Ala Arg Ser Ser Asn Val Gln Ile Cys Thr Pro
            340                 345                 350        Pro

Asn Ile Glu Thr Gly Leu Cys Ser Asn Ser Ile Val Pro Phe Thr Ser
        355                 360                 365

Phe Thr Asp His Leu Thr Tyr Tyr Asp Leu Asn Glu Gly Leu Cys Leu
370                 375                 380
```

<210> SEQ ID NO 13
<211> LENGTH: 378
<212> TYPE: PRT
<213> ORGANISM: Actinomucor elegans

<400> SEQUENCE: 13

```
Met Val Ser Phe Ala Ser Ile Pro Gln Ala Val Gln Tyr Leu Ile Ile
 1               5                  10                  15

Ala Ser Cys Leu Met Met Ser Thr Ser Glu Ala Ala Pro Val Ala Gly
            20                  25                  30

Asn Arg Thr Leu Thr Asp Leu Val Ser Phe Thr Leu Pro Pro Ile Ile
        35                  40                  45
```

```
Ser Asp Arg Val Ile Ala Pro Lys Val Pro Ala Val Asn His Asn Lys
     50                  55                  60

Glu Lys Asp Asn Ile Ala Lys Asn Leu Lys Trp Tyr Arg Glu His Gly
 65                  70                  75                  80

Gly Lys Val Lys Ile Gly Lys Arg Asp Gly Glu Leu Val Gly Gly Met
                     85                  90                  95

Thr Met Asp Leu Pro Ala Asp Ala Pro Pro Thr Pro Pro Glu Pro Ala
                100                 105                 110

Glu Gly Ser Val Tyr Ile Ala Ser Ala Ser Glu Ile Ala Glu Phe Lys
                115                 120                 125

Lys Tyr Ala Gly Ile Ala Ala Thr Ala Tyr Cys Arg Asp Val Val Pro
130                 135                 140

Gly Thr Asn Trp Asp Cys Thr Gln Cys Gln Lys Tyr Ala Pro Asp Gly
145                 150                 155                 160

Gln Leu Ile Lys Thr Phe Thr Ser Leu Ile Thr Asp Thr Asn Gly Phe
                165                 170                 175

Val Leu Arg Ser Asp Ser Gln Lys Thr Ile Tyr Leu Val Phe Arg Gly
                180                 185                 190

Thr Asn Ser Ile Arg Ser Ala Ile Thr Asp Leu Val Phe Asp Leu Thr
                195                 200                 205

Asp Tyr Ala Pro Val Ala Gly Ala Lys Val His Lys Gly Phe Leu Ala
210                 215                 220

Ser Tyr Lys Glu Val Val Asn Lys Tyr Phe Pro Val Ile Gln Asp Glu
225                 230                 235                 240

Leu Thr Ala Phe Pro Thr Tyr Lys Ile Ile Val Thr Gly His Ser Leu
                245                 250                 255

Gly Gly Ala Gln Ala Leu Leu Ala Ala Leu Asp Leu Tyr Gln Arg Asp
                260                 265                 270

Lys Arg Ile Gly Pro Asn Asn Leu Ser Ile Phe Thr Val Gly Ala Pro
275                 280                 285

Arg Val Gly Asn Pro Thr Phe Ala Tyr Tyr Val Asp Ser Thr Asp Leu
290                 295                 300

Pro Phe Ser Arg Ser Val Asn Asp Arg Asp Ile Val Pro His Val Pro
305                 310                 315                 320

Pro Gln Ala Phe Gly Tyr Leu His Ala Gly Val Glu Ala Trp Ala Arg
                325                 330                 335

Thr Ser Thr His Val Gln Ile Cys Asn Ser Gln Ile Glu Thr Gly Ser
                340                 345                 350

Cys Ser Asn Ser Ile Val Pro Phe Thr Ser Phe Thr Asp His Leu Thr
355                 360                 365

Tyr Tyr Gly Ile Asn Glu Gly Leu Cys Leu
370                 375

<210> SEQ ID NO 14
<211> LENGTH: 383
<212> TYPE: PRT
<213> ORGANISM: Actinomucor elegans

<400> SEQUENCE: 14

Met Val Ser Phe Thr Leu Ile Ser His Gly Val Lys Leu Val Leu Val
 1               5                  10                  15

Thr Ser Cys Leu Met Met Gly Ser Ser Glu Ser Ala Pro Val Ala Gly
                 20                  25                  30

Asn Lys Thr Val Ala Asn Ser Ser Asn Val Thr Ser Asp Ser Phe Val
```

```
            35                  40                  45
Leu Pro Ser Ile Ile Ala Glu Arg Val Ile Ala Pro Lys Val Pro Val
 50                  55                  60

Gly Asn His Asn Met Glu Lys Asp Ala Ile Thr Lys Asn Leu Lys Trp
 65                  70                  75                  80

Tyr Glu Glu His Val Gly Lys Ala Asn Ile Thr Lys Arg Gly Gly Glu
                 85                  90                  95

Thr Val Gly Gly Met Thr Met Asp Leu Pro Ala Asn Ala Pro Pro Thr
                100                 105                 110

Pro Ala Ile Thr Thr Ser Asp Ala Ile Tyr Val Ala Ser Thr Ala Gln
                115                 120                 125

Val Thr Glu Phe Lys Lys Tyr Ala Gly Ile Ala Ala Thr Ala Tyr Cys
130                 135                 140

Arg Asp Val Val Pro Gly Thr Lys Trp Asn Cys Ala Gln Cys Leu Lys
145                 150                 155                 160

Tyr Ala Pro Asp Gly Lys Leu Ile Lys Thr Phe Thr Ser Leu Ile Ser
                165                 170                 175

Asp Thr Asn Gly Phe Val Met Arg Ser Asp Ser Gln Lys Thr Ile Tyr
                180                 185                 190

Leu Val Phe Arg Gly Thr Asn Ser Ile Arg Ser Ala Ile Thr Asp Met
                195                 200                 205

Val Phe Asp Leu Ala Ala Tyr Gly Pro Val Ser Gly Ala Lys Val His
210                 215                 220

Arg Gly Phe Leu Ala Ser Tyr Gln Gln Val Val Gly Ser Tyr Phe Pro
225                 230                 235                 240

Val Val Gln Asn Gln Leu Thr Ser Tyr Pro Thr Tyr Lys Val Ile Val
                245                 250                 255

Thr Gly His Ser Leu Gly Gly Ala Gln Ala Leu Leu Ala Ala Leu Asp
                260                 265                 270

Leu Tyr Gln Arg Asp Lys Arg Phe Gly Pro Asn Asn Met Ser Ile Phe
                275                 280                 285

Thr Val Gly Cys Pro Arg Val Gly Asn Pro Thr Phe Ala Tyr Tyr Val
290                 295                 300

Asp Ser Thr Asn Ile Pro Phe Ser Arg Ser Val Asn Asp Arg Asp Ile
305                 310                 315                 320

Val Pro His Leu Pro Pro Gln Ala Phe Gly Tyr Leu His Pro Gly Val
                325                 330                 335

Glu Ala Trp Ala Arg Ser Ser Thr Asn Val Gln Ile Cys Asn Ser Gln
                340                 345                 350

Ile Glu Thr Ser Ser Cys Ser Asn Ser Ile Val Pro Phe Thr Ser Ile
                355                 360                 365

Glu Asp His Leu Thr Tyr Tyr Gly Ile Asn Glu Gly Lys Cys Leu
                370                 375                 380

<210> SEQ ID NO 15
<211> LENGTH: 377
<212> TYPE: PRT
<213> ORGANISM: Mucor wutungkiao

<400> SEQUENCE: 15

Met Val Ser Phe Val Ser Ile Ser Gln Gly Ile Ser Leu Phe Ile Ile
 1               5                  10                  15

Val Ser Ser Met Leu Thr Gly Ser Thr Asn Ala Ala Pro Thr Ser Thr
                20                  25                  30
```

```
Asn Lys Thr Thr Glu Ala Thr Thr Phe Thr Leu Pro Pro Leu Ile Ser
         35                  40                  45

Ser Arg Ile Ile Ala Pro Lys Val Pro Ser Gly Ser His Asp Val Glu
 50                  55                  60

Ala Ala Asn Ile Leu Lys Asn Lys Glu Trp Phe Glu Ala Asn Gly Gly
 65                  70                  75                  80

Lys Leu Asn Val Thr Lys Arg Asp Asp Glu Thr Val Gly Gly Met Tyr
                 85                  90                  95

Met Asp Leu Pro Ser Asn Ser Pro Ala Ile Pro Ala Val Ser Asn Glu
                100                 105                 110

Ser Thr Val Val Ile Ala Thr Ala Gln Ile Thr Glu Leu Lys Met
                115                 120                 125

Tyr Ala Gly Ile Ala Ser Thr Ala Tyr Cys Arg Ser Val Val Pro Leu
130                 135                 140

Asn Ala Trp Thr Cys Thr Asn Cys Leu Lys Phe Val Pro Asp Gly Lys
145                 150                 155                 160

Leu Ile Thr Thr Phe Ser Ser Leu Ile Thr Asp Thr Asn Gly Phe Val
                165                 170                 175

Leu Arg Ser Asp Ala Gln Lys Thr Ile Tyr Leu Val Phe Arg Gly Thr
                180                 185                 190

Asn Ser Ile Arg Ser Ala Ile Thr Asp Leu Ile Phe Asp Phe Thr Asp
                195                 200                 205

Tyr Thr Pro Val Ser Gly Ala Lys Val His Lys Gly Phe Tyr Ala Ser
210                 215                 220

Tyr Lys Glu Val Val Asn Ser Tyr Phe Pro Tyr Ile Gln Ser Gln Leu
225                 230                 235                 240

Thr Ala Tyr Pro Thr Tyr Lys Val Ile Val Thr Gly His Ser Leu Gly
                245                 250                 255

Gly Ala Gln Ala Leu Leu Ala Gly Met Asp Leu Tyr Gln Arg Glu Ser
                260                 265                 270

Arg Leu Ser Lys Ser Asn Leu Ala Ile Tyr Thr Val Gly Cys Pro Arg
                275                 280                 285

Thr Gly Asn Pro Ala Phe Ala Tyr Tyr Val Glu Ser Thr Gly Ile Thr
290                 295                 300

Phe Ser Arg Ser Val Asn Asn Arg Asp Ile Val Pro His Val Pro Pro
305                 310                 315                 320

Gln Ala Phe Gly Tyr Leu His Pro Gly Val Glu Ala Trp Ala Arg Ser
                325                 330                 335

Ser Ser Lys Val Gln Ile Cys Thr Pro Asp Ile Glu Thr Ser Leu Cys
                340                 345                 350

Ser Asn Ser Ile Val Pro Phe Thr Ser Phe Thr Asp His Leu Thr Tyr
                355                 360                 365

Tyr Asp Ile Asn Glu Gly Leu Cys Leu
370                 375

<210> SEQ ID NO 16
<211> LENGTH: 392
<212> TYPE: PRT
<213> ORGANISM: Rhizopus oryzae

<400> SEQUENCE: 16

Met Val Ser Phe Ile Ser Ile Ser Gln Gly Val Ser Leu Cys Leu Leu
1               5                   10                  15

Val Ser Ser Met Met Leu Gly Ser Ala Val Pro Val Ser Gly Lys
                20                  25                  30
```

-continued

```
Ser Gly Ser Ser Asn Thr Ala Val Ser Ala Ser Asp Asn Ala Ala Leu
        35                  40                  45
Pro Pro Leu Ile Ser Ser Arg Cys Ala Pro Pro Ser Asn Lys Gly Ser
 50                  55                  60
Lys Ser Asp Leu Gln Ala Glu Pro Tyr Asn Met Gln Lys Asn Thr Glu
 65                  70                  75                  80
Trp Tyr Glu Ser His Gly Gly Asn Leu Thr Ser Ile Gly Lys Arg Asp
                 85                  90                  95
Asp Asn Leu Val Gly Gly Met Thr Leu Asp Leu Pro Ser Asp Ala Pro
                100                 105                 110
Pro Ile Ser Leu Ser Ser Thr Asn Ser Ala Ser Asp Gly Gly Lys
                115                 120                 125
Val Val Ala Ala Thr Thr Ala Gln Ile Gln Glu Phe Thr Lys Tyr Ala
    130                 135                 140
Gly Ile Ala Ala Thr Ala Tyr Cys Arg Ser Val Val Pro Gly Asn Lys
145                 150                 155                 160
Trp Asp Cys Val Gln Cys Gln Lys Trp Val Pro Asp Gly Lys Ile Ile
                165                 170                 175
Thr Thr Phe Thr Ser Leu Leu Ser Asp Thr Asn Gly Tyr Val Leu Arg
                180                 185                 190
Ser Asp Lys Gln Lys Thr Ile Tyr Leu Val Phe Arg Gly Thr Asn Ser
            195                 200                 205
Phe Arg Ser Ala Ile Thr Asp Ile Val Phe Asn Phe Ser Asp Tyr Lys
        210                 215                 220
Pro Val Lys Gly Ala Lys Val His Ala Gly Phe Leu Ser Ser Tyr Glu
225                 230                 235                 240
Gln Val Val Asn Asp Tyr Phe Pro Val Val Gln Glu Gln Leu Thr Ala
                245                 250                 255
His Pro Thr Tyr Lys Val Ile Val Thr Gly His Ser Leu Gly Gly Ala
                260                 265                 270
Gln Ala Leu Leu Ala Gly Met Asp Leu Tyr Gln Arg Glu Pro Arg Leu
            275                 280                 285
Ser Pro Lys Asn Leu Ser Ile Phe Thr Val Gly Gly Pro Arg Val Gly
        290                 295                 300
Asn Pro Thr Phe Ala Tyr Tyr Val Glu Ser Thr Gly Ile Pro Phe Gln
305                 310                 315                 320
Arg Thr Val His Lys Arg Asp Ile Val Pro His Val Pro Pro Gln Ser
                325                 330                 335
Phe Gly Phe Leu His Pro Gly Val Glu Ser Trp Ile Lys Ser Gly Thr
            340                 345                 350
Ser Asn Val Gln Ile Cys Thr Ser Glu Ile Glu Thr Lys Asp Cys Ser
        355                 360                 365
Asn Ser Ile Val Pro Phe Thr Ser Ile Leu Asp His Leu Ser Tyr Phe
    370                 375                 380
Asp Ile Asn Glu Gly Ser Cys Leu
385                 390
```

METHODS FOR PRODUCING LIPASES

CROSS-REFERENCE TO RELATED APPLICATIONS

This application is a 35 U.S.C. 371 national application of PCT/EP2016/079277 filed Nov. 30, 2016, which claims priority or the benefit under 35 U.S.C. 119 of European application no. 16153166.0 filed on Jan. 28, 2016, and of Indian application no. 6448/CHE/2015 filed on Dec. 1, 2015, the contents of which are fully incorporated herein by reference.

REFERENCE TO A SEQUENCE LISTING

This application contains a Sequence Listing in computer readable form, which is incorporated herein by reference.

FIELD OF THE INVENTION

The present invention relates to lipase variants, polynucleotides encoding the variants, methods of producing the variants, and methods of using the variants.

BACKGROUND OF THE INVENTION

Lipases are important biocatalysts which have shown to be useful for various applications. Lipases have been employed in the removal of lipid stains and have been added to various compositions. Current cleaning and/or fabric care compositions comprise many active ingredients which are interfering with the ability of lipases to remove lipid stains and in particular the stability of lipases in such compositions is still a challenge. A need exists for lipases that can function in the harsh environment of compositions used for cleaning.

SUMMARY OF THE INVENTION

Lipases have for many years been employed with success in various applications. However, the selection of efficient lipases available for use in cleaning compositions is still quite limited. Attempts have been made to modify lipases to obtain variants with altered characteristics such as activity, stability, etc. to provide lipases with better compatibility with cleaning composition components. So far there is still a challenge in providing lipases which are not only able to survive the harsh environment of the cleaning compositions but at the same time show a wash performance.

The present invention relates to methods for generating preparation of lipases with increased stability which upon contact with an activator may be activated or reactivated thereby regaining its hydrolytic activity which is the basis of providing a wash effect.

The present invention also relates to polynucleotides encoding the variants; nucleic acid constructs, vectors, and host cells comprising the polynucleotides; and methods of producing and use of the variants.

According to the present invention there is provided a method for generating a preparation of a lipase variant of a parent lipase comprising a step of altering one or more nucleotides in a polynucleotide encoding the parent lipase, wherein the alteration provides at least one disulfide bond and a hydrolytic activity of said lipase variant which is reduced as compared with the hydrolytic activity of the parent lipase.

According to the present invention there is provided a method for obtaining a lipase variant of a parent lipase, comprising introducing into a parent lipase an alteration at one or more positions of the parent lipase, wherein the alteration at one or more positions provides at least one disulfide bond and wherein the hydrolytic activity of the lipase variant is reduced as compared to the hydrolytic activity of the parent lipase, when hydrolytic activity is determined according to example 3.

Preferably the lipase variant has a propeptide and a mature part in which the step of altering one or more nucleotides results in the propeptide and/or the mature part containing a cysteine residue.

Conveniently, the step of altering one or more nucleotides results in the propeptide and/or the mature part containing two cysteine residues.

Advantageously, the parent lipase is a zygomycete lipase and/or has at least 50% sequence identity with SEQ ID NO: 2.

Preferably, the parent lipase is a zygomycete lipase having the amino acid sequence of SEQ ID NO: 2; SEQ ID NO: 8; SEQ ID NO: 9; SEQ ID NO: 10; SEQ ID NO: 11; SEQ ID NO: 12; SEQ ID NO: 13; SEQ ID NO: 14; SEQ ID NO: 15; or SEQ ID NO: 16.

Conveniently, the step of altering one or more nucleotides comprises a substitution at one or more positions corresponding to positions −57, −54, −47, −46, −43, −40, −38, −37, −36, −33, −31, −24, 101, 102, 104, 120, 182, 186, 212, 216, 239, 240, 246 and 249 of SEQ ID NO: 2.

Advantageously, the step of altering one or more nucleotides comprises a substitution at one or more positions corresponding to positions −57, −54, −47, −46, −43, −40, −38, −37, −36, −33, −31, −24, and comprises a substitution at one or more positions corresponding to positions 101, 102, 104, 120, 182, 186, 212, 216, 239, 240, 246 and 249 of SEQ ID NO: 2.

Preferably, the step of altering one or more nucleotides comprises a substitution at one or more residues corresponding to positions selected from L-57C/N120C, L-54C/P101C, A-47C/V102C, A-24C/G104C, P-46C/N186C, A-43C/N186C, T-40C/P182C, T-40C/L216C, T-40C/L239C, D-38C/A212C, P-37C/E240C, P-37C/N246C, E-36C/N246C, E-36C/V249C, A-33C/V249C and M-31C/V249C of SEQ ID NO: 2.

Preferably a method for obtaining a lipase variant of a parent lipase, comprising introducing into the parent lipase a substitution at one or more positions corresponding to positions −57, −54, −47, −46, −43, −40, −38, −37, −36, −33, −31, −24, 101, 102, 104, 120, 182, 186, 212, 216, 239, 240, 246 and 249 of SEQ ID NO: 2, wherein the substitution provides at least one disulfide bond and wherein the hydrolytic activity of said lipase variant is reduced as compared with the hydrolytic activity of the parent lipase, when measured according to example 3.

Preferably the alteration is selected from one or more of the following substitutions selected from L-57C/N120C, L-54C/P101C, A-47C/V102C, S-24C/G104C, P-46C/N186C, S-43C/N186C, T-40C/P182C, T-40C/L216C, T-40C/L239C, D-38C/A212C, P-37C/E240C, P-37C/N246C, E-36C/N246C, E-36C/V249C, A-33C/V249C and S-31C/V249C wherein the position corresponds to the positions of SEQ ID NO: 2.

According to the present invention is provided a lipase variant obtained by a method of the invention.

According to the present invention, there is provided a polynucleotide encoding a lipase variant of a parent lipase comprising an alteration at one or more nucleotides, wherein the alteration provides at least one disulfide bond and a hydrolytic activity of said lipase variant which is reduced as compared with the hydrolytic activity of the parent lipase.

According to the present invention, there is provided a polynucleotide obtainable by the method of the invention.

According to the present invention, there is provided a nucleic acid construct comprising the polynucleotide of the invention.

According to the present invention, there is provided an expression vector comprising the polynucleotide of any the invention.

According to the present invention, there is provided a host cell comprising the polynucleotide of the invention.

According to the present invention, there is provided a method for producing a lipase from the polynucleotide of the invention comprising: (a) cultivating the host cell of the invention under conditions suitable for expression of the lipase variant; and (b) recovering the lipase variant.

According to the present invention, there is provided a lipase variant prepared according to the aforementioned method of the invention.

According to the present invention, there is provided a lipase variant of a parent lipase comprising an alteration at one or more nucleotides, wherein the alteration provides at least one disulfide bond and a hydrolytic activity of said lipase variant which is reduced as compared with the hydrolytic activity of the parent lipase Preferably, the lipase variant comprises a substitution at one or more positions corresponding to positions −57, −54, −47, −46, −43, −40, −38, −37, −36, −33, −31, −24, 101, 102, 104, 120, 182, 186, 212, 216, 239, 240, 246 and 249 of SEQ ID NO: 2.

Conveniently, the lipase variant comprises a substitution at one or more positions corresponding to −57, −54, −47, −46, −43, −40, −38, −37, −36, −33, −31 and −24, and comprises a substitution at one or more positions corresponding to positions 101, 102, 104, 120, 182, 186, 212, 216, 239, 240, 246 and 249, of SEQ ID NO: 2.

Advantageously, the lipase variant comprises a substitution at one or more residues corresponding to positions selected from L-57C/N120C, L-54C/P101C, A-47C/V102C, A-24C/G104C, P-46C/N186C, A-43C/N186C, T-40C/P182C, T-40C/L216C, T-40C/L239C, D-38C/A212C, P-37C/E240C, P-37C/N246C, E-36C/N246C, E-36C/V249C, A-33C/V249C and M-31C/V249C of SEQ ID NO: 2.

Preferably, the amino acid sequence of said lipase variant has at least 50% sequence identity with SEQ ID NO: 2; SEQ ID NO: 8; SEQ ID NO: 9; SEQ ID NO: 10; SEQ ID NO: 11; SEQ ID NO: 12; SEQ ID NO: 13; SEQ ID NO: 14; SEQ ID NO: 15; or SEQ ID NO: 16.

Preferably, the amino acid sequence of the lipase variant has at least 50% sequence identity, e.g. at least 60%, at least 70%, at least 80%, at least 85%, at least 90% or at least 95% with SEQ ID NO: 2; SEQ ID NO: 8; SEQ ID NO: 9; SEQ ID NO: 10; SEQ ID NO: 11; SEQ ID NO: 12; SEQ ID NO: 13 SEQ ID NO: 14 SEQ ID NO: 15; or SEQ ID NO: 16.

According to the present invention, there is provided a composition comprising the lipase variant of any the invention.

Preferably, the composition of the invention is formulated as a regular, compact or concentrated liquid; a gel; a paste; a soap bar; a regular or a compacted powder; a granulated solid; a homogenous or a multilayer tablet with two or more layers (same or different phases); a pouch having one or more compartments; a single or a multi-compartment unit dose form; or any combination thereof.

Conveniently, the composition of the invention further comprises an activator.

Advantageously, the activator is a protease and/or a reducing agent.

According to the present invention, there is provided a method of cleaning comprising contacting a surface or an item with a composition of the invention.

According to the present invention, there is provided a method for increasing the hydrolytic activity of a lipase variant of any of the invention, comprising a step of bringing said lipase variant into contact with an activator.

DETAILED DISCLOSURE OF THE INVENTION

Definitions

Lipase: The terms "lipase", "lipase enzyme", "lipolytic enzyme", "lipid esterase", "lipolytic polypeptide", and "lipolytic protein" refers to an enzyme in class EC3.1.1 as defined by Enzyme Nomenclature. It may have lipase activity (triacylglycerol lipase, EC3.1.1.3), cutinase activity (EC3.1.1.74), sterol esterase activity (EC3.1.1.13) and/or wax-ester hydrolase activity (EC3.1.1.50). For purposes of the present invention, lipase activity is determined according to the procedure described in the Examples. In one aspect, the variants of the present invention have at least 20%, e.g., at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100% of the lipase activity of the polypeptide of SEQ ID NO: 2, SEQ ID NO: 6, SEQ ID NO: 8; SEQ ID NO: 9; SEQ ID NO: 10; SEQ ID NO: 11; SEQ ID NO: 12; SEQ ID NO: 13; SEQ ID NO: 14; SEQ ID NO: 15; SEQ ID NO: 16.

Lipase substrate: The term "lipase substrate" may be any substrate that is subject to the activity of a lipase as defined above.

Fabric: The term "fabric" as used herein refers to any suitable fabric, textile and/or linen serving the purpose of the present invention as described.

Wash performance: In the present context the term "wash performance" is used as an enzyme's ability to degrade and/or remove lipid or lipid-containing stains present on a fabric to be cleaned. The wash performance may be quantified by calculating the delta remission index value defined in the Methods section below. The wash performance may be measured on all types of suitable fabrics as described including any fabrics used in laundry, and industrial and institutional cleaning.

Activator: The term "activator" means any agent or substance that can activate or reactivate a lipase of the invention, for example by breaking a disulfide bond and/or degrading the propeptide. Activators include (1) enzymes that degrade the propeptide, such as e.g. enzymes with endopeptidase activity, exopeptidase activity, aminopeptidase activity, carboxypeptidase activity, protease activity, and the like; and (2) reducing agents that break the cysteine bridge (cys-bridge, C—C bridge) such as e.g. tris(2-carboxyethyl)phosphine (TCEP), dithiothreitol (DTT), 2-mercaptoethanol (beta-ME), tris(3-hydroxypropyl)phosphine (THPP) and sulphite (such as sodium sulphite).

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a variant of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Disulfide bond: The terms "disulfide bond", "disulfide link", "disulfide bridge", "cysteine bond", "cysteine link", "cysteine bridge", "S—S bond", "S—S link", "S—S bridge", are intended to have the same meaning, referring to a bond between the thiols of two cysteine amino acid residues.

Expression: The term "expression" includes any step involved in the production of a variant including, but not limited to, transcription, post-transcriptional modification, translation, post-translational modification, and secretion.

Expression vector: The term "expression vector" means a linear or circular DNA molecule that comprises a polynucleotide encoding a variant and is operably linked to control sequences that provide for its expression.

Fragment: The term "fragment" means a polypeptide having one or more (e.g., several) amino acids absent from the amino and/or carboxyl terminus of a mature polypeptide; wherein the fragment has lipase activity. In one aspect, a fragment contains at least 50%, at least 55%, at least 60%, at least 65%, at least 70%, at least 75%, at least 80%, at least 85%, at least 90%, or at least 95% but less than 100% of the number of amino acids 1 to 269 of SEQ ID NO: 3 or the number of amino acids 1 to 269 of SEQ ID NO: 7.

High stringency conditions: The term "high stringency conditions" means for probes of at least 100 nucleotides in length, prehybridization and hybridization at 42° C. in 5×SSPE, 0.3% SDS, 200 microgram/mL sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Improved property: The term "improved property" means a characteristic associated with a variant that is improved compared to the parent. Such improved properties include, but are not limited to: Stability such as e.g. thermostability, thermostability in detergent, stability in detergent, storage stability; Activity such as e.g. increased or reduced (i.e. changed) hydrolytic activity, changed hydrolytic activity in detergent; Ability to be activated; Ability to be reactivated; Substrate specific activity; Stain removal such as e.g. lipid stain removal; and Wash performance.

Isolated: The term "isolated" means a substance in a form or environment which does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 1 to 269 of SEQ ID NO: 2 which is identical with amino acids 1 to 269 of SEQ ID NO: 3. In one aspect, the mature polypeptide is amino acids 1 to 269 of SEQ ID NO: 6 which is identical with amino acids 1 to 269 of SEQ ID NO: 7. It is known in the art that a host cell may produce a mixture of two or more different mature polypeptides (i.e., with a different C-terminal and/or N-terminal amino acid) expressed by the same polynucleotide. Accordingly, in one aspect the mature peptide may start at amino acid 1, 2, 3, 4, or 5 of SEQ ID NO: 3 or SEQ ID NO: 7.

Mature polypeptide coding sequence: The term "mature polypeptide coding sequence" means a polynucleotide that encodes a mature polypeptide having lipase activity. In one aspect, the mature polypeptide coding sequence is nucleotides 295 to 930 of SEQ ID NO: 1. In one aspect, the mature polypeptide coding sequence is nucleotides 67 to 873 of SEQ ID NO: 5.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

Mutant: The term "mutant" means a polynucleotide encoding a variant.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Parent or parent lipase: The term "parent" or "parent lipase" means a lipase to which an alteration is made to produce the enzyme variants of the present invention. The parent may be a naturally occurring (wild-type) polypeptide or a variant or fragment thereof.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of Alignment–
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the –nobrief option) is used as the percent identity and is calculated as follows:

(Identical Deoxyribonucleotides×100)/(Length of
Alignment–Total Number of Gaps in Alignment)

Subsequence: The term "subsequence" means a polynucleotide having one or more (e.g., several) nucleotides absent from the 5' and/or 3' end of a mature polypeptide coding sequence; wherein the subsequence encodes a fragment having lipase activity. In one aspect, a subsequence contains at least 50%, at least 55%, at least 60%, at least 65%, at least 70%, at least 75%, at least 80%, at least 85%, at least 90%, or at least 95% but less than 100% of the number of nucleotides 295 to 930 of SEQ ID NO: 1; or 67 to 873 of SEQ ID NO: 5.

Variant: The term "variant" or "lipase variant" means a polypeptide having lipase activity comprising an alteration, i.e., a substitution, insertion, and/or deletion, at one or more (e.g., several) positions as compared to a parent lipase from which it is derived. A substitution means replacement of the amino acid occupying a position with a different amino acid; a deletion means removal of the amino acid occupying a position; and an insertion means adding an amino acid adjacent to and immediately following the amino acid occupying a position. The variants of the present invention have at least 20%, e.g., at least 40%, at least 50%, at least 60%, at least 70%, at least 80%, at least 90%, at least 95%, or 100% of the lipase activity of the parent lipase. In some aspects the parent lipase is SEQ ID NO: 3; SEQ ID NO: 7; SEQ ID NO: 8; SEQ ID NO: 9; SEQ ID NO: 10; SEQ ID NO: 11; SEQ ID NO: 12; SEQ ID NO: 13 SEQ ID NO: 14 SEQ ID NO: 15; or SEQ ID NO: 16.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

Wild-type lipase: The term "wild-type" lipase means a lipase expressed by a naturally occurring microorganism, such as a bacterium, yeast, or filamentous fungus found in nature.

Conventions for Designation of Variants

For purposes of the present invention, the polypeptide disclosed in SEQ ID NO: 3 or SEQ ID NO: 7 is used to determine the corresponding amino acid residue in another lipase. The polypeptide disclosed in SEQ ID NO 2 may also be used as reference sequence for numbering the corresponding positions in other polypeptides. A negative sign "–" may be used before a position number of an amino acid indicating that changes are made in the propeptide –94 to –1 of SEQ ID NO 2. The amino acid sequence of another lipase is aligned with e.g. SEQ ID NO 2, SEQ ID NO: 3 or SEQ ID NO: 7, and based on the alignment, the amino acid position number corresponding to any amino acid residue in SEQ ID NO 2, SEQ ID NO: 3 or SEQ ID NO: 7 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix.

Identification of the corresponding amino acid residue in another lipase can be determined by an alignment of multiple polypeptide sequences using several computer programs including, but not limited to, MUSCLE (multiple sequence comparison by log-expectation; version 3.5 or later; Edgar, 2004, *Nucleic Acids Research* 32: 1792-1797), MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537:_39-64; Katoh and Toh, 2010, *Bioinformatics* 26:_1899-1900), and EMBOSS EMMA employing ClustalW (1.83 or later; Thompson et al., 1994, *Nucleic Acids Research* 22: 4673-4680), using their respective default parameters.

When the other enzyme has diverged from the polypeptide of SEQ ID NO 2, SEQ ID NO: 3 or SEQ ID NO: 7 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementation of these algorithms can additionally be utilized to query structure databases with a structure of interest in order to discover possible structural homologs (e.g., Holm and Park, 2000, *Bioinformatics* 16: 566-567).

In describing the variants of the present invention, the nomenclature described below is adapted for ease of reference. The accepted IUPAC single letter or three letter amino acid abbreviation is employed.

Substitutions.

For an amino acid substitution, the following nomenclature is used: Original amino acid, position, substituted amino acid. Accordingly, the substitution of threonine at position 226 with alanine is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively.

In the context of the present invention. The amino acids to be altered e.g. substituted are indicated with the amino acids present in SEQ ID NO 2 e.g. A-47C. It is clear to the skilled artisan that the invention is not limited to variants of SEQ ID NO 2 i.e. SEQ ID NO 2 as parent lipase. When other lipases are modified the "starting" amino acid may be different. This may also be indicated with an X e.g. X-47C.

Deletions.

For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions.

For an amino acid insertion, the following nomenclature is used: Original amino acid, position, original amino acid, inserted amino acid. Accordingly, the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---|---|
| 195 | 195 195a 195b |
| G | G-K-A |

Multiple Alterations.

Variants comprising multiple alterations are separated by addition marks ("+"), e.g., "Arg170Tyr+Gly195Glu" or "R170Y+G195E" representing a substitution of arginine and glycine at positions 170 and 195 with tyrosine and glutamic acid, respectively.

Different Alterations.

Where different alterations can be introduced at a position, the different alterations are separated by a comma, e.g., "Arg170Tyr,Glu" represents a substitution of arginine at position 170 with tyrosine or glutamic acid. Thus, "Tyr167Gly,Ala+Arg170Gly,Ala" designates the following variants:
"Tyr167Gly+Arg170Gly", "Tyr167Gly+Arg170Ala", "Tyr167Ala+Arg170Gly", and "Tyr167Ala+Arg170Ala".

Variants

The present invention relates to a lipase variant of a parent lipase, which variant has lipase activity, at least 75% but less than 100% sequence identity to SEQ ID NO: 2 and comprises a substitution at one or more positions corresponding to positions −57, −54, −47, −46, −43, −40, −38, −37, −36, −33, −31, −24, 101, 102, 104, 120, 182, 186, 212, 216, 239, 240, 246 and 249 of SEQ ID NO: 2.

The negative sign "−" before a position number e.g. −57 indicate the changes are made in a position corresponding to a position in the propeptide region e.g. in the propeptide region of SEQ ID NO 2 i.e. −94 to −1 of SEQ ID NO 2. The alterations are not limited to alterations made in SEQ ID NO 2 this sequence is used for numbering as described in "Conventions for Designation of Variants" above.

The present invention relates to a lipase variant of a parent lipase, which variant has lipase activity, at least 75% but less than 100% sequence identity to SEQ ID NO: 2 and comprises a substitution at one or more positions in a region referred to as the propeptide corresponding to positions −57, −54, −47, −46, −43, −40, −38, −37, −36, −33, −31 and −24, and comprises a substitution at one or more positions in a region referred to as the mature protein corresponding to positions 101, 102, 104, 120, 182, 186, 212, 216, 239, 240, 246 and 249, of SEQ ID NO: 2.

The present invention also relates to a variant, wherein the variant comprises substitutions at residues of SEQ ID NO: 2 selected from L-57C/N120C, L-54C/P101C, A-47CN/102C, A-24C/G104C, P-46C/N186C, A-43C/N186C, T-40C/P182C, T-40C/L216C, T-40C/L239C, D-38C/A212C, P-37C/E240C, P-37C/N246C, E-36C/N246C, E-36C/V249C, A-33C/V249C and M-31C/V249C.

In some aspects the invention relates to a variant selected from the group consisting of: (a) a polypeptide having at least 80%, at least 82%, at least 84%, at least 86%, at least 88%, at least 90%, at least 91%, at least 92%, at least 93%, at least 94%, at least 95%, at least 96%, at least 97%, at least 98%, at least 99% but less than 100% sequence identity to the polypeptide of SEQ ID NO: 3; (b) a polypeptide encoded by a polynucleotide that hybridizes under low stringency conditions, medium stringency conditions, medium-high stringency conditions, high stringency conditions, or very high stringency conditions with (i) the polypeptide coding sequence of SEQ ID NO: 1 or (ii) the full-length complement of (i); (c) a polypeptide encoded by a polynucleotide having at least 80%, at least 82%, at least 84%, at least 86%, at least 88%, at least 90%, at least 91%, at least 92%, at least 93%, at least 94%, at least 95%, at least 96%, at least 97%, at least 98%, at least 99% but less than 100% sequence identity to the polypeptide coding sequence of SEQ ID NO: 3; and (d) a fragment of the polypeptide of SEQ ID NO: 3, wherein the fragment has lipase activity.

In some aspects the invention relates to a variant which has sequence identity of at least 80%, at least 82%, at least 84%, at least 86%, at least 88%, at least 90%, at least 91%, at least 92%, at least 93%, at least 94%, at least 95%, at least 96%, at least 97%, at least 98%, at least 99% but less than 100% sequence identity to the amino acid sequence of the parent lipase.

In some aspects the invention relates to a variant which has at least at least 80%, at least 82%, at least 84%, at least 86%, at least 88%, at least 90%, at least 91%, at least 92%, at least 93%, at least 94%, at least 95%, at least 96%, at least 97%, at least 98%, at least 99% but less than 100% sequence identity to SEQ ID NO: 3.

In some aspects the invention relates to a variant which has at least at least 80%, at least 82%, at least 84%, at least 86%, at least 88%, at least 90%, at least 91%, at least 92%, at least 93%, at least 94%, at least 95%, at least 96%, at least 97%, at least 98%, at least 99% but less than 100% sequence identity to SEQ ID NO: 7.

In some aspects the invention relates to a variant wherein the number of substitutions in the variants of the present invention is 1-40, e.g., 1-30, 1-20, 1-10 and 1-5, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 substitutions.

In some aspects the invention relates to a variant comprising or consisting of a substitution of an amino acid with C. In another aspect, the variant comprises or consists of the substitution of an amino acid of SEQ ID NO: 2 with C.

In some aspects the invention relates to a variant comprising or consisting of a substitution of 1 amino acid with C. In another aspect, the variant comprises or consists of the substitution of 1 amino acid of SEQ ID NO: 2 with C.

In some aspects the invention relates to a variant comprising or consisting of a substitution of 2 amino acids with C. In another aspect, the variant comprises or consists of the substitution of 2 amino acids of SEQ ID NO: 2 with C.

In some aspects the invention relates to a variant comprising or consisting of a substitution at a position corresponding to position A-24. In another aspect, the amino acid at a position corresponding to position A-24 is substituted with C. In another aspect, the variant comprises or consists of the substitution A-24C of SEQ ID NO: 2.

In some aspects the invention relates to a variant comprising or consisting of a substitution at a position corresponding to position S-24. In another aspect, the amino acid at a position corresponding to position S-24 is substituted with C. In another aspect, the variant comprises or consists of the substitution S-24C of SEQ ID NO: 2.

In some aspects the invention relates to a variant comprising or consisting of a substitution at a position corresponding to position M-31. In another aspect, the amino acid at a position corresponding to position M-31 is substituted with C. In another aspect, the variant comprises or consists of the substitution M-31C of SEQ ID NO: 2.

In some aspects the invention relates to a variant comprising or consisting of a substitution at a position corresponding to position S-31. In another aspect, the amino acid at a position corresponding to position S-31 is substituted with C. In another aspect, the variant comprises or consists of the substitution S-31C of SEQ ID NO: 2.

In some aspects the invention relates to a variant comprising or consisting of a substitution at a position corresponding to position A-33. In another aspect, the amino acid at a position corresponding to position A-33 is substituted with C. In another aspect, the variant comprises or consists of the substitution A-33C of SEQ ID NO: 2.

In some aspects the invention relates to a variant comprising or consisting of a substitution at a position corresponding to position E-36. In another aspect, the amino acid at a position corresponding to position E-36 is substituted with C. In another aspect, the variant comprises or consists of the substitution E-36C of SEQ ID NO: 2.

In some aspects the invention relates to a variant comprising or consisting of a substitution at a position corresponding to position P-37. In another aspect, the amino acid at a position corresponding to position P-37 is substituted with C. In another aspect, the variant comprises or consists of the substitution P-37C of SEQ ID NO: 2.

In some aspects the invention relates to a variant comprising or consisting of a substitution at a position corresponding to position D-38. In another aspect, the amino acid at a position corresponding to position D-38 is substituted with C. In another aspect, the variant comprises or consists of the substitution D-38C of SEQ ID NO: 2.

In some aspects the invention relates to a variant comprising or consisting of a substitution at a position corresponding to position T-40. In another aspect, the amino acid at a position corresponding to position T-40 is substituted with C. In another aspect, the variant comprises or consists of the substitution T-40C of SEQ ID NO: 2.

In some aspects the invention relates to a variant comprising or consisting of a substitution at a position corresponding to position A-43. In another aspect, the amino acid at a position corresponding to position A-43 is substituted with C. In another aspect, the variant comprises or consists of the substitution A-43C of SEQ ID NO: 2.

In some aspects the invention relates to a variant comprising or consisting of a substitution at a position corresponding to position S-43. In another aspect, the amino acid at a position corresponding to position S-43 is substituted with C. In another aspect, the variant comprises or consists of the substitution S-43C of SEQ ID NO: 2.

In some aspects the invention relates to a variant comprising or consisting of a substitution at a position corresponding to position P-46. In another aspect, the amino acid at a position corresponding to position P-46 is substituted with C. In another aspect, the variant comprises or consists of the substitution P-46C of SEQ ID NO: 2.

In some aspects the invention relates to a variant comprising or consisting of a substitution at a position corresponding to position A-47. In another aspect, the amino acid at a position corresponding to position A-47 is substituted with C. In another aspect, the variant comprises or consists of the substitution A-47C of SEQ ID NO: 2.

In some aspects the invention relates to a variant comprising or consisting of a substitution at a position corresponding to position L-54. In another aspect, the amino acid at a position corresponding to position L-54 is substituted with C. In another aspect, the variant comprises or consists of the substitution L-54C of SEQ ID NO: 2.

In some aspects the invention relates to a variant comprising or consisting of a substitution at a position corresponding to position L-57. In another aspect, the amino acid at a position corresponding to position L-57 is substituted with C. In another aspect, the variant comprises or consists of the substitution L-57C of SEQ ID NO: 2.

In some aspects the invention relates to a variant comprising or consisting of a substitution at a position corresponding to position P101. In another aspect, the amino acid at a position corresponding to position P101 is substituted with C. In another aspect, the variant comprises or consists of the substitution P101C of SEQ ID NO: 2.

In some aspects the invention relates to a variant comprising or consisting of a substitution at a position corresponding to position V102. In another aspect, the amino acid at a position corresponding to position V102 is substituted with C. In another aspect, the variant comprises or consists of the substitution V102C of SEQ ID NO: 2.

In some aspects the invention relates to a variant comprising or consisting of a substitution at a position corresponding to position G104. In another aspect, the amino acid at a position corresponding to position G104 is substituted with C. In another aspect, the variant comprises or consists of the substitution G104C of SEQ ID NO: 2.

In some aspects the invention relates to a variant comprising or consisting of a substitution at a position corresponding to position N120. In another aspect, the amino acid at a position corresponding to position N120 is substituted with C. In another aspect, the variant comprises or consists of the substitution N120C of SEQ ID NO: 2.

In some aspects the invention relates to a variant comprising or consisting of a substitution at a position corresponding to position P182. In another aspect, the amino acid at a position corresponding to position P182 is substituted with C. In another aspect, the variant comprises or consists of the substitution P182C of SEQ ID NO: 2.

In some aspects the invention relates to a variant comprising or consisting of a substitution at a position corresponding to position N186. In another aspect, the amino acid at a position corresponding to position N186 is substituted with C. In another aspect, the variant comprises or consists of the substitution N186C of SEQ ID NO: 2.

In some aspects the invention relates to a variant comprising or consisting of a substitution at a position corresponding to position A212. In another aspect, the amino acid at a position corresponding to position A212 is substituted with C. In another aspect, the variant comprises or consists of the substitution A212C of SEQ ID NO: 2.

In some aspects the invention relates to a variant comprising or consisting of a substitution at a position corresponding to position L216. In another aspect, the amino acid at a position corresponding to position L216 is substituted with C. In another aspect, the variant comprises or consists of the substitution L216C of SEQ ID NO: 2.

In some aspects the invention relates to a variant comprising or consisting of a substitution at a position corresponding to position L239. In another aspect, the amino acid at a position corresponding to position L239 is substituted with C. In another aspect, the variant comprises or consists of the substitution L239C of SEQ ID NO: 2.

In some aspects the invention relates to a variant comprising or consisting of a substitution at a position corresponding to position E240. In another aspect, the amino acid at a position corresponding to position E240 is substituted with C. In another aspect, the variant comprises or consists of the substitution E240C of SEQ ID NO: 2.

In some aspects the invention relates to a variant comprising or consisting of a substitution at a position corresponding to position N246. In another aspect, the amino acid at a position corresponding to position N246 is substituted with C. In another aspect, the variant comprises or consists of the substitution N246C of SEQ ID NO: 2.

In some aspects the invention relates to a variant comprising or consisting of a substitution at a position corresponding to position V249. In another aspect, the amino acid at a position corresponding to position V249 is substituted with C. In another aspect, the variant comprises or consists of the substitution V249C of SEQ ID NO: 2.

In some aspects the invention related to a variant, wherein the variant has one or more (e.g several) improved property relative to the parent measured as an Improvement Factor (IF) that is greater than 1.0, wherein the improved property is selected from the group consisting of: Thermostability; Thermostability in Detergent; Hydrolytic Activity in Detergent; Stability in Detergent. Preferably, the improved property is Hydrolytic Activity in Detergent. The lipase variant of the invention has a lower Hydrolytic Activity as compared to its parent lipase, before activation. The Hydrolytic Activity of the lipase variant of the invention increases when the disulfide bond is broken and/or the propeptide is degraded. The Hydrolytic Activity can be determined using the assay set out in Example 5 or example 3, by measuring the release of 4-methylumbelliferone (4-MU) by stored detergent/protein samples incubated with 1.35% (w/v) Savinase for 15 minutes in 0.2M HEPES buffer, pH 8.5.

In some aspects the invention related to a variant, wherein the Improvement Factor (IF) is greater than 1.0 in at least one of the assays selected from the group consisting of: A Thermostability Assay; B Thermostability in Detergent Assay; C Performance Screening Assay; and D Stability in Detergent Assay as described in PCT/EP2015/061509. In some aspects the invention related to a variant, wherein the Improvement Factor (IF) is greater than 1.0 in at least two, in at least three, or in at least four assays.

In some aspects the invention related to a variant, wherein the Improvement Factor (IF) is at least 1.1; 1.2; 1.3; 1.4; 1.5; 1.6; 1.7; 1.8; 1.9; 2.0; 2.1; 2.3; 2.4; or 2.5.

In some aspects the invention relates to a variant, wherein the variant has lipase activity and comprises a substitution at one or more (e.g. several) of the positions corresponding to position −57, −54, −47, −46, −43, −40, −38, −37, −36, −33, −31, −24, 101, 102, 104, 120, 182, 186, 212, 216, 239, 240, 246 and 249 of SEQ ID NO: 2, or of a polypeptide having at least 75%, at least 80%, at least 85%, at least 90%, at least 91%, at least 92%, at least 93%, at least 94%, at least 95%, at least 96%, at least 97%, at least 98%, at least 99%, or 100% identity to SEQ ID NO: 2 and has improved stability in detergent as compared to the parent i.e. IF>1.0. The improved property may be measured by the Detergent Stability Assay or the Hydrolytic Activity Assay as described in Example 5.

In some aspects the invention relates to a variant, wherein the variant has lipase activity and comprises a substitution at one or more (e.g. several) of the positions corresponding to position −57, −54, −47, −46, −43, −40, −38, −37, −36, −33, −31 and −24 (propeptide), and a substitution at one or more (e.g. several) of the positions corresponding to position 101, 102, 104, 120, 182, 186, 212, 216, 239, 240, 246 and 249 (mature protein), of SEQ ID NO: 2, or of a polypeptide having at least 75%, at least 80%, at least 85%, at least 90%, at least 91%, at least 92%, at least 93%, at least 94%, at least 95%, at least 96%, at least 97%, at least 98%, at least 99%, or 100% identity to SEQ ID NO: 2 and has improved stability in detergent as compared to the parent i.e. IF>1.0. The improved property may be measured by the Detergent Stability Assay or the Hydrolytic Activity Assay as described in Example 5.

The variants may further comprise one or more additional substitutions at one or more (e.g., several) other positions.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

For example, the variants may further comprise a substitution at one or more positions corresponding to: A8T; Y28LC; I41T; C43S; D48E; K50E; Y60AC; D61NKRAVLSTC; R80C; S84C; I86C; N87C; A90C; D91NKRAVLST; F94LTK; S98P; S103R; D113NKRAVLST; S114C; G116V; N120KD; K131F; G156D; N186Y; E201QKRAVLST; I204VATSG; V205IL; L208VATSG; F213VATSG; H217N; D226NKRAVLST; T236A; T241S; D243NKRAVLSTH; V254IATSG; L255VATSG; D256NKRAVLST; L258VATSG; Y260WCGV; L267VATSG of SEQ ID NO: 3.

Essential amino acids in a polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for lipase activity to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309: 59-64. The identity of essential amino acids can also be inferred from an alignment with a related polypeptide.

Parent Lipases

The parent lipase may be a lipase of the *Humicola* family or the Zygomycetes family. The *Humicola* family comprises the lipase from *H. lanuginosa* strain DSM 4109 and lipases having more than 50% homology with said lipase. The lipase from H. *Lanuginosa* (synonym *Thermomyces lanuginosus* lipase, TIL) has the amino acid sequence shown in SEQ ID NO: 6. This family also includes: lipase from *Penicillium camemberlii* (P25234), lipase from *Fusarium oxysporum* (EP130064, WO98/26057), lipase from *F. heterosporum* (R87979), lipase from *A. oryzae* (O85895), lipase from *A. niger* (Y09330), lipase from *A. tubingensis* (Y09331), lipase from *A. tubingensis* (WO98/45453), lipase from *F. solanii* having an isoelectric point of 6.9 and an apparent molecular weight of 30 kDa (WO96/18729). The Zygomycetes family comprises lipases having at least 50% homology with the lipase of *Rhizomucor miehei* (SEQ ID NO: 3). This family also includes the lipases of SEQ ID NO: 9; SEQ ID NO: 10; SEQ ID NO: 11; SEQ ID NO: 12; SEQ ID NO: 13; SEQ ID NO: 14; SEQ ID NO: 15; SEQ ID NO: 16; as well as the lipases from *Absidia reflexa, A. sporophora, A. corymbifera, A. blakesleeana, A. griseola* described in WO96/13578 and WO97/27276.

The parent lipase may be (a) a polypeptide having at least 75% sequence identity to SEQ ID NO: 3; (b) a polypeptide encoded by a polynucleotide that hybridizes under low stringency conditions with (i) the mature polypeptide coding sequence of SEQ ID NO: 1, (ii) the full-length complement of (i) or (ii); (c) a polypeptide encoded by a polynucleotide having at least 75% sequence identity to the mature polypeptide coding sequence of SEQ ID NO: 1, (d) a polypeptide having at least 75% sequence identity to SEQ ID NO: 7; (b) a polypeptide encoded by a polynucleotide that hybridizes under low stringency conditions with (i) the mature polypeptide coding sequence of SEQ ID NO: 5, (ii) the full-length complement of (i) or (ii); or (e) a polypeptide encoded by a polynucleotide having at least 75% sequence identity to the mature polypeptide coding sequence of SEQ ID NO: 5. In an aspect, the parent has a sequence identity to SEQ ID NO: 3 of at least 75%, e.g., at least 80%, at least 85%, at least 90%, at least 91%, at least 92%, at least 93%, at least 94%, at least 95%, at least 96%, at least 97%, at least 98%, at least 99%, or 100%, which have lipase activity. In one aspect, the amino acid sequence of the parent differs by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 from SEQ ID NO: 3.

In an aspect, the parent has a sequence identity to SEQ ID NO: 7 of at least 75%, e.g., at least 80%, at least 85%, at least 90%, at least 91%, at least 92%, at least 93%, at least 94%, at least 95%, at least 96%, at least 97%, at least 98%, at least 99%, or 100%, which have lipase activity. In one aspect, the amino acid sequence of the parent differs by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 from SEQ ID NO: 7.

In an aspect, the parent has a sequence identity to SEQ ID NO: 2 of at least 75%, e.g., at least 80%, at least 85%, at least 90%, at least 91%, at least 92%, at least 93%, at least 94%, at least 95%, at least 96%, at least 97%, at least 98%, at least 99%, or 100%, which have lipase activity. In one aspect, the amino acid sequence of the parent differs by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 from SEQ ID NO: 2.

In an aspect, the parent has a sequence identity to SEQ ID NO: 6 of at least 75%, e.g., at least 80%, at least 85%, at least 90%, at least 91%, at least 92%, at least 93%, at least 94%, at least 95%, at least 96%, at least 97%, at least 98%, at least 99%, or 100%, which have lipase activity. In one aspect, the amino acid sequence of the parent differs by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 from SEQ ID NO: 6.

In an aspect, the parent has a sequence identity to SEQ ID NO: 6 of at least 75%, e.g., at least 80%, at least 85%, at least 90%, at least 91%, at least 92%, at least 93%, at least 94%, at least 95%, at least 96%, at least 97%, at least 98%, at least 99%, or 100%, which have lipase activity. In one aspect, the amino acid sequence of the parent differs by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 from SEQ ID NO: 8.

In an aspect, the parent has a sequence identity to SEQ ID NO: 6 of at least 75%, e.g., at least 80%, at least 85%, at least 90%, at least 91%, at least 92%, at least 93%, at least 94%, at least 95%, at least 96%, at least 97%, at least 98%, at least 99%, or 100%, which have lipase activity. In one aspect, the amino acid sequence of the parent differs by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 from SEQ ID NO: 9.

In an aspect, the parent has a sequence identity to SEQ ID NO: 6 of at least 75%, e.g., at least 80%, at least 85%, at least 90%, at least 91%, at least 92%, at least 93%, at least 94%, at least 95%, at least 96%, at least 97%, at least 98%, at least 99%, or 100%, which have lipase activity. In one aspect, the amino acid sequence of the parent differs by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 from SEQ ID NO: 10.

In an aspect, the parent has a sequence identity to SEQ ID NO: 6 of at least 75%, e.g., at least 80%, at least 85%, at least 90%, at least 91%, at least 92%, at least 93%, at least 94%, at least 95%, at least 96%, at least 97%, at least 98%, at least 99%, or 100%, which have lipase activity. In one aspect, the amino acid sequence of the parent differs by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 from SEQ ID NO: 11.

In an aspect, the parent has a sequence identity to SEQ ID NO: 6 of at least 75%, e.g., at least 80%, at least 85%, at least 90%, at least 91%, at least 92%, at least 93%, at least 94%, at least 95%, at least 96%, at least 97%, at least 98%, at least 99%, or 100%, which have lipase activity. In one aspect, the amino acid sequence of the parent differs by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 from SEQ ID NO: 12.

In an aspect, the parent has a sequence identity to SEQ ID NO: 6 of at least 75%, e.g., at least 80%, at least 85%, at least 90%, at least 91%, at least 92%, at least 93%, at least 94%, at least 95%, at least 96%, at least 97%, at least 98%, at least 99%, or 100%, which have lipase activity. In one aspect, the amino acid sequence of the parent differs by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 from SEQ ID NO: 13.

In an aspect, the parent has a sequence identity to SEQ ID NO: 6 of at least 75%, e.g., at least 80%, at least 85%, at least 90%, at least 91%, at least 92%, at least 93%, at least 94%, at least 95%, at least 96%, at least 97%, at least 98%, at least 99%, or 100%, which have lipase activity. In one aspect, the amino acid sequence of the parent differs by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 from SEQ ID NO: 14.

In an aspect, the parent has a sequence identity to SEQ ID NO: 6 of at least 75%, e.g., at least 80%, at least 85%, at least 90%, at least 91%, at least 92%, at least 93%, at least 94%, at least 95%, at least 96%, at least 97%, at least 98%, at least 99%, or 100%, which have lipase activity. In one aspect, the amino acid sequence of the parent differs by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 from SEQ ID NO: 15.

In an aspect, the parent has a sequence identity to SEQ ID NO: 6 of at least 75%, e.g., at least 80%, at least 85%, at least 90%, at least 91%, at least 92%, at least 93%, at least 94%, at least 95%, at least 96%, at least 97%, at least 98%, at least 99%, or 100%, which have lipase activity. In one aspect, the amino acid sequence of the parent differs by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 from SEQ ID NO: 16.

In another aspect, the parent comprises or consists of the amino acid sequence of SEQ ID NO: 2. In another aspect, the parent comprises or consists of the mature polypeptide of SEQ ID NO: 2. In another aspect, the parent comprises or consists of amino acids 1 to 269 of SEQ ID NO: 2. In another aspect, the parent comprises or consists of SEQ ID NO: 3. In another aspect, the parent comprises or consists of amino acids 1 to 269 of SEQ ID NO: 3.

In another aspect, the parent comprises or consists of the amino acid sequence of SEQ ID NO: 6. In another aspect, the parent comprises or consists of the mature polypeptide of SEQ ID NO: 6. In another aspect, the parent comprises or consists of amino acids 1 to 269 of SEQ ID NO: 6. In another aspect, the parent comprises or consists of SEQ ID NO: 7. In another aspect, the parent comprises or consists of amino acids 1 to 269 of SEQ ID NO: 7.

In another aspect, the parent is a fragment of the polypeptide of SEQ ID NO: 3. In one aspect, a fragment contains at least 50%, at least 55%, at least 60%, at least 65%, at least 70%, at least 75%, at least 80%, at least 85%, at least 90%, or at least 95% but less than 100% of the number of amino acids 1 to 269 of SEQ ID NO: 3.

In another aspect, the parent is a fragment of the polypeptide of SEQ ID NO: 7. In one aspect, a fragment contains at least 50%, at least 55%, at least 60%, at least 65%, at least 70%, at least 75%, at least 80%, at least 85%, at least 90%, or at least 95% but less than 100% of the number of amino acids 1 to 269 of SEQ ID NO: 7.

In another embodiment, the parent is an allelic variant of SEQ ID NO: 3.

In another embodiment, the parent is an allelic variant of SEQ ID NO: 7.

In another aspect, the parent is encoded by a polynucleotide that hybridizes under very low stringency conditions, low stringency conditions, medium stringency conditions, medium-high stringency conditions, high stringency conditions, or very high stringency conditions with (i) the mature polypeptide coding sequence of SEQ ID NO: 1, (ii) the full-length complement of (i) (Sambrook et al., 1989, *Molecular Cloning, A Laboratory Manual*, 2d edition, Cold Spring Harbor, New York).

The polynucleotide of SEQ ID NO: 1 or a subsequence thereof, as well as the polypeptide of SEQ ID NO: 2 or a fragment thereof, the polynucleotide of SEQ ID NO: 5 or a subsequence thereof, as well as the polypeptide of SEQ ID NO: 6 or a fragment thereof may be used to design nucleic acid probes to identify and clone DNA encoding a parent from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

A genomic DNA or cDNA library prepared from such other strains may be screened for DNA that hybridizes with the probes described above and encodes a parent. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1 or a subsequence thereof, or with SEQ ID NO: 5 or a subsequence thereof, the carrier material is used in a Southern blot.

For purposes of the present invention, hybridization indicates that the polynucleotide hybridizes to a labeled nucleic acid probe corresponding to (i) SEQ ID NO: 1; (ii) the mature polypeptide coding sequence of SEQ ID NO: 1; (iii) the full-length complement thereof; or (iv) a subsequence thereof; (v) SEQ ID NO: 5; (vi) the mature polypeptide coding sequence of SEQ ID NO: 5; (vii) the full-length complement thereof; or (viii) a subsequence thereof; under very low to very high stringency conditions. Molecules to which the nucleic acid probe hybridizes under these conditions can be detected using, for example, X-ray film or any other detection means known in the art.

In one aspect, the nucleic acid probe is the mature polypeptide coding sequence of SEQ ID NO: 1. In another aspect, the nucleic acid probe is nucleotides 292 to 1098 of SEQ ID NO: 1. In another aspect, the nucleic acid probe is a polynucleotide that encodes the polypeptide of SEQ ID NO: 2; the mature polypeptide thereof; or a fragment thereof. In another aspect, the nucleic acid probe is SEQ ID NO: 1.

In one aspect, the nucleic acid probe is the mature polypeptide coding sequence of SEQ ID NO: 5. In another aspect, the nucleic acid probe is nucleotides 67 to 873 of SEQ ID NO: 5. In another aspect, the nucleic acid probe is a polynucleotide that encodes the polypeptide of SEQ ID NO: 6; the mature polypeptide thereof; or a fragment thereof. In another aspect, the nucleic acid probe is SEQ ID NO: 5.

In another embodiment, the parent is encoded by a polynucleotide having a sequence identity to the mature polypeptide coding sequence of SEQ ID NO: 1 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

The polypeptide may be a hybrid polypeptide in which a region of one polypeptide is fused at the N-terminus or the C-terminus of a region of another polypeptide.

The parent may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987;

Carter et al., 1989, *Proteins: Structure, Function, and Genetics* 6: 240-248; and Stevens, 2003, *Drug Discovery World* 4: 35-48.

The parent may be obtained from microorganisms of any genus. For purposes of the present invention, the term "obtained from" as used herein in connection with a given source shall mean that the parent encoded by a polynucleotide is produced by the source or by a strain in which the polynucleotide from the source has been inserted. In one aspect, the parent is secreted extracellularly.

The parent may be a filamentous fungal lipase such as an *Acremonium, Agaricus, Alternaria, Aspergillus, Aureobasidium, Botryosphaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella,* or *Xylaria* lipase.

In another aspect, the parent is an *Acremonium cellulolyticus, Aspergillus aculeatus, Aspergillus awamori, Aspergillus foetidus, Aspergillus fumigatus, Aspergillus japonicus, Aspergillus nidulans, Aspergillus niger, Aspergillus oryzae, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa* inter alia *Thermomyces lanuginosus, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia setosa, Thielavia spededonium, Thielavia subthermophila, Thielavia terrestris, Trichoderma harzianum, Trichoderma koningii, Trichoderma longibrachiatum, Trichoderma reesei,* or *Trichoderma viride* lipase.

In another aspect, the parent is a Zygomycetes lipase, e.g., the lipase of *Absidia* sp. e.g. the lipase of SEQ ID NO: 8; *Rhizopus microsporus* var. *chinensis* e.g. the lipase of SEQ ID NO: 9; *Phycomyces nitens* e.g. the lipase of SEQ ID NO: 10; *Mucor circinelloides* e.g. the lipase of SEQ ID NO: 11 or SEQ ID NO: 12; *Actinomucor elegans* e.g. the lipase of SEQ ID NO: 13 or SEQ ID NO: 14; *Mucor wutungkiao* e.g. the lipase of SEQ ID NO: 15; or *Rhizopus oryzae* e.g. the lipase of SEQ ID NO: 16.

In another aspect, the parent is a *Rhizomucor miehei* lipase (RmL), e.g., the lipase of SEQ ID NO: 2 or the mature polypeptide thereof which is identical with SEQ ID NO: 3.

In another aspect, the parent is a *Thermomyces lanuginosus* lipase (TlL), e.g., the lipase of SEQ ID NO: 6 or the mature polypeptide thereof which is identical with SEQ ID NO: 7.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSMZ), Centraalbureau Voor Schimmelcultures (CBS), and Agricultural Research Service Patent Culture Collection, Northern Regional Research Center (NRRL).

The parent may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding a parent may then be obtained by similarly screening a genomic DNA or cDNA library of another microorganism or mixed DNA sample. Once a polynucleotide encoding a parent has been detected with the probe(s), the polynucleotide can be isolated or cloned by utilizing techniques that are known to those of ordinary skill in the art (see, e.g., Sambrook et al., 1989, supra).

Preparation of Variants

The present invention also relates to methods for obtaining a lipase variant and/or a fragment thereof, comprising introducing into a parent lipase a substitution at one or more positions corresponding to positions −57, −54, −47, −46, −43, −40, −38, −37, −36, −33, −31, −24, 101, 102, 104, 120, 182, 186, 212, 216, 239, 240, 246 and 249 of SEQ ID NO: 2, wherein the variant and/or fragment has lipase activity; and recovering the variant and/or fragment.

The present invention also relates to methods for obtaining a lipase variant and/or a fragment thereof, comprising introducing into a parent lipase a substitution at one or more positions corresponding to positions −57, −54, −47, −46, −43, −40, −38, −37, −36, −33, −31, and −24, and comprises a substitution at one or more positions corresponding to positions 101, 102, 104, 120, 182, 186, 212, 216, 239, 240, 246 and 249, of SEQ ID NO: 2.

In some aspects the invention relates to methods for obtaining a lipase variant and/or a fragment thereof, comprising introducing into a parent lipase a substitution at one or more positions corresponding to −24C, −31C, −33C, −36C, −37C, −38C, −40C, −43C, −46C, −47C, −54C and −57C, and comprises a substitution at one or more positions corresponding to positions 101C, 102C, 104C, 120C, 182C, 186C, 212C, 216C, 239C, 240C, 246C and 249C, of SEQ ID NO: 2, wherein the variant and/or fragment has lipase activity; and recovering the variant and/or fragment.

In some aspects the invention relates to methods for obtaining a lipase variant and/or a fragment thereof, comprising introducing into a parent lipase substitutions at residues of SEQ ID NO: 2 selected from L-57C/N120C, L-54C/P101C, A-47C/V102C, A-24C/G104C, P-46C/N186C, A-43C/N186C, T-40C/P182C, T-40C/L216C, T-40C/L239C, D-38C/A212C, P-37C/E240C, P-37C/N246C, E-36C/N246C, E-36C/V249C, A-33C/V249C and M-31C/V249C, wherein the variant and/or fragment has lipase activity; and recovering the variant and/or fragment.

The variants can be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (e.g., several) mutations are introduced at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, *Proc. Natl. Acad. Sci. USA* 76: 4949-4955; and Barton et al., 1990, *Nucleic Acids Res.* 18: 7349-4966.

Site-directed mutagenesis can also be accomplished in vivo by methods known in the art. See, e.g., U.S. Patent Application Publication No. 2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Any site-directed mutagenesis procedure can be used in the present invention. There are many commercial kits available that can be used to prepare variants.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, *Proc. Natl. Acad. Sci. USA* 86: 2152-2156; WO95/17413; or WO95/22625. Other methods that can be used include error-prone PCR, phage display (e.g., Lowman et al., 1991, *Biochemistry* 30: 10832-10837; U.S. Pat. No. 5,223,409; WO92/06204) and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

Polynucleotides

The present invention also relates to polynucleotides encoding a variant of the present invention.

Nucleic Acid Constructs

The present invention also relates to nucleic acid constructs comprising a polynucleotide encoding a variant of the present invention operably linked to one or more control sequences that direct the expression of the coding sequence in a suitable host cell under conditions compatible with the control sequences.

The polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide which is recognized by a host cell for expression of the polynucleotide. The promoter contains transcriptional control sequences that mediate the expression of the variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO96/00787), *Fusarium venenatum* amyloglucosidase (WO00/56900), *Fusarium venenatum* Daria (WO00/56900), *Fusarium venenatum* Quinn (WO00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, Yeast 8: 423-488.

The control sequence may also be a transcription terminator, which is recognized by a host cell to terminate transcription. The terminator sequence is operably linked to the 3'-terminus of the polynucleotide encoding the variant. Any terminator that is functional in the host cell may be used.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO94/25612) and a *Bacillus subtilis* SP82 gene (Hue et al., 1995, Journal of Bacteriology 177: 3465-3471).

The control sequence may also be a leader, a nontranslated region of an mRNA that is important for translation by the host cell. The leader sequence is operably linked to the 5'-terminus of the polynucleotide encoding the variant. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the variant-encoding sequence and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a variant and directs the variant into the cell's secretory pathway. The 5'-end of the coding sequence of the polynucleotide may inherently contain a signal peptide coding sequence naturally linked in translation reading frame with the segment of the coding sequence that encodes the variant. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the variant. However, any signal peptide coding sequence that directs the expressed variant into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, Microbiological Reviews 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a variant. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of the variant and the signal peptide sequence is positioned next to the N-terminus of the propeptide sequence.

It may also be desirable to add regulatory sequences that regulate expression of the variant relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the variant would be operably linked with the regulatory sequence.

Expression Vectors

The present invention also relates to recombinant expression vectors comprising a polynucleotide encoding a variant of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

The vector preferably contains an element(s) that permits integration of the vector into the host cell's genome or autonomous replication of the vector in the cell independent of the genome.

For integration into the host cell genome, the vector may rely on the polynucleotide's sequence encoding the variant or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, Gene 98: 61-67; Cullen et al., 1987, *Nucleic Acids Res.* 15: 9163-9175; WO00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide encoding a variant of the present invention operably linked to one or more control sequences that direct the production of a variant of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the variant and its source.

The host cell may be any cell useful in the recombinant production of a variant, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell, including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, Mol. Gen. Genet. 168: 111-115), competent cell transformation (see, e.g., Young and Spizizen, 1961, J. Bacteriol. 81: 823-829, or Dubnau and Davidoff-Abelson, 1971, J. Mol. Biol. 56: 209-221), electroporation (see, e.g., Shigekawa and Dower, 1988, Biotechniques 6: 742-751), or conjugation (see, e.g., Koehler and Thorne, 1987, J. Bacteriol. 169: 5271-5278). The introduction of DNA into an *E. coli* cell may be effected by protoplast transformation (see, e.g., Hanahan, 1983, J. Mol. Biol. 166: 557-580) or electroporation (see, e.g., Dower et al., 1988, Nucleic Acids Res. 16: 6127-6145). The introduction of DNA into a *Streptomyces* cell may be effected by protoplast transformation, electroporation (see, e.g., Gong et al., 2004, Folia Microbiol. (Praha) 49: 399-405), conjugation (see, e.g., Mazodier et al., 1989, J. Bacteriol. 171: 3583-3585), or transduction (see, e.g., Burke et al., 2001, Proc. Natl. Acad. Sci. USA 98: 6289-6294). The introduction of DNA into a *Pseudomonas* cell may be effected by electroporation (see, e.g., Choi et al., 2006, J. Microbiol. Methods 64: 391-397), or conjugation (see, e.g., Pinedo and Smets, 2005, Appl. Environ. Microbiol. 71: 51-57). The introduction of DNA into a *Streptococcus* cell may be effected by natural competence (see, e.g., Perry and Kuramitsu, 1981, Infect. Immun. 32: 1295-1297), protoplast transformation (see, e.g., Catt and Jollick, 1991, Microbios 68: 189-207), electroporation (see, e.g., Buckley et al., 1999, Appl. Environ. Microbiol. 65: 3800-3804) or conjugation (see, e.g., Clewell, 1981, Microbiol. Rev. 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, Ainsworth and Bisby's Dictionary of The Fungi, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, Soc. App. Bacteriol. Symposium Series No. 9, 1980).

The yeast host cell may be a *Candida, Hansenula, Kluyveromyces, Pichia, Saccharomyces, Schizosaccharomyces*, or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense,*

*Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucormiehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, Gene 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology,* Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a variant, comprising: (a) cultivating a host cell of the present invention under conditions suitable for expression of the variant; and (b) recovering the variant.

The host cells are cultivated in a nutrient medium suitable for production of the variant using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The variant may be detected using methods known in the art that are specific for the variants. These detection methods include, but are not limited to, use of specific antibodies, formation of an enzyme product, or disappearance of an enzyme substrate. For example, an enzyme assay may be used to determine the activity of the variant may be the assay described in the examples below.

The variant may be recovered using methods known in the art. For example, the variant may be recovered from the nutrient medium by conventional procedures including, but not limited to, collection, centrifugation, filtration, extraction, spray-drying, evaporation, or precipitation.

The variant may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, Janson and Ryden, editors, VCH Publishers, New York, 1989) to obtain substantially pure variants.

In an alternative aspect, the variant is not recovered, but rather a host cell of the present invention expressing the variant is used as a source of the variant.

Compositions.

In one aspect the invention relates to a composition comprising a lipase variant of a parent lipase, which variant has lipase activity, at least 75% but less than 100% sequence identity to SEQ ID NO: 2 and comprises a substitution at one or more positions corresponding to positions −57, −54, −47, −46, −43, −40, −38, −37, −36, −33, −31, −24, 101, 102, 104, 120, 182, 186, 212, 216, 239, 240, 246 and 249 of SEQ ID NO: 2.

In one aspect the invention relates to a composition comprising a lipase variant of a parent lipase, which variant has lipase activity, at least 75% but less than 100% sequence identity to SEQ ID NO: 2 and comprises a substitution at one or more positions corresponding to positions −57, −54, −47, −46, −43, −40, −38, −37, −36, −33, −31 and −24 (propeptide), and comprises a substitution at one or more positions corresponding to positions 101, 102, 104, 120, 182, 186, 212, 216, 239, 240, 246 and 249 (mature protein), of SEQ ID NO: 2.

In another aspect the invention relates to a composition comprising a lipase variant of a parent lipase, which variant has lipase activity, at least 75% but less than 100% sequence identity to SEQ ID NO: 2 and comprises a substitution at one or more positions corresponding to −24C, −31C, −33C, −36C, −37C, −38C, −40C, −43C, −46C, −47C, −54C and −57C, and comprises a substitution at one or more positions corresponding to 101C, 102C, 104C, 120C, 182C, 186C, 212C, 216C, 239C, 240C, 246C and 249C, of SEQ ID NO: 2.

Detergents

In some aspects the present invention relates to a composition comprising the lipase prepared according to the method.

In some aspects the present invention relates to a composition formulated as a regular, compact or concentrated liquid; a gel; a paste; a soap bar; a regular or a compacted powder; a granulated solid; a homogenous or a multilayer tablet with two or more layers (same or different phases); a pouch having one or more compartments; a single or a multi-compartment unit dose form; or any combination thereof.

In some aspects the present invention relates to a composition further comprising an activator. In some aspects the activator is a reducing agent and/or a protein degrading agent. In some aspects the reducing agent is tris(2-carboxyethyl)phosphine (TCEP), dithiothreitol (DTT), 2-mercaptoethanol (beta-ME), tris(3-hydroxypropyl)phosphine (THPP), sulphite (such as sodium sulphite), or the like. In some aspects the protein degrading agent is an enzyme with endopeptidase activity, exopeptidase activity, aminopeptidase activity, carboxypeptidase activity, protease activity, and the like.

In some aspects the present invention relates to a composition in which the activity of the lipase variant is increased by bringing said lipase variant into contact with an activator.

The non-limiting list of composition components illustrated hereinafter are suitable for use in the compositions and methods herein may be desirably incorporated in certain embodiments of the invention, e.g. to assist or enhance cleaning performance, for treatment of the substrate to be cleaned, or to modify the aesthetics of the composition as is the case with perfumes, colorants, dyes or the like. The levels of any such components incorporated in any compositions are in addition to any materials previously recited for incorporation. The precise nature of these additional components, and levels of incorporation thereof, will depend on the physical form of the composition and the nature of the cleaning operation for which it is to be used. Although components mentioned below are categorized by general header according to a particular functionality, this is not to be construed as a limitation, as a component may comprise additional functionalities as will be appreciated by the skilled artisan.

Unless otherwise indicated the amounts in percentage is by weight of the composition (wt %). Suitable component materials include, but are not limited to, surfactants, builders, chelating agents, dye transfer inhibiting agents, dispersants, enzymes, and enzyme stabilizers, catalytic materials, bleach activators, hydrogen peroxide, sources of hydrogen peroxide, preformed peracids, polymeric dispersing agents, clay soil removal/anti-redeposition agents, brighteners, suds suppressors, dyes, hueing dyes, perfumes, perfume delivery systems, structure elasticizing agents, fabric softeners, carriers, hydrotropes, processing aids, solvents and/or pigments. In addition to the disclosure below, suitable examples of such other components and levels of use are found in U.S. Pat. Nos. 5,576,282, 6,306,812, and 6,326,348 hereby incorporated by reference.

Thus, in certain embodiments the invention do not contain one or more of the following adjuncts materials: surfactants, soaps, builders, chelating agents, dye transfer inhibiting agents, dispersants, additional enzymes, enzyme stabilizers, catalytic materials, bleach activators, hydrogen peroxide, sources of hydrogen peroxide, preformed peracids, polymeric dispersing agents, clay soil removal/anti-redeposition agents, brighteners, suds suppressors, dyes, perfumes, perfume delivery systems, structure elasticizing agents, fabric softeners, carriers, hydrotropes, processing aids, solvents and/or pigments. However, when one or more components are present, such one or more components may be present as detailed below:

Surfactants—

The compositions according to the present invention may comprise a surfactant or surfactant system wherein the surfactant can be selected from nonionic surfactants, anionic surfactants, cationic surfactants, ampholytic surfactants, zwitterionic surfactants, semipolar nonionic surfactants and mixtures thereof. When present, surfactant is typically present at a level of from 0.1 to 60 wt %, from 0.2 to 40 wt %, from 0.5 to 30 wt %, from 1 to 50 wt %, from 1 to 40 wt %, from 1 to 30 wt %, from 1 to 20 wt %, from 3 to 10 wt %, from 3 to 5 wt %, from 5 to 40 wt %, from 5 to 30 wt %, from 5 to 15 wt %, from 3 to 20 wt %, from 3 to 10 wt %, from 8 to 12 wt %, from 10 to 12 wt % or from 20 to 25 wt %.

Suitable anionic detersive surfactants include sulphate and sulphonate detersive surfactants.

Suitable sulphonate detersive surfactants include alkyl benzene sulphonate, in one aspect, $C_{10-13}$ alkyl benzene sulphonate. Suitable alkyl benzene sulphonate (LAS) may be obtained, by sulphonating commercially available linear alkyl benzene (LAB); suitable LAB includes low 2-phenyl LAB, such as Isochem® or Petrelab®, other suitable LAB include high 2-phenyl LAB, such as Hyblene®. A suitable anionic detersive surfactant is alkyl benzene sulphonate that is obtained by DETAL catalyzed process, although other synthesis routes, such as HF, may also be suitable. In one aspect a magnesium salt of LAS is used.

Suitable sulphate detersive surfactants include alkyl sulphate, in one aspect, $C_{8-18}$ alkyl sulphate, or predominantly $C_{12}$ alkyl sulphate.

Another suitable sulphate detersive surfactant is alkyl alkoxylated sulphate, in one aspect, alkyl ethoxylated sulphate, in one aspect, a $C_{8-18}$ alkyl alkoxylated sulphate, in another aspect, a $C_{8-8}$ alkyl ethoxylated sulphate, typically the alkyl alkoxylated sulphate has an average degree of alkoxylation of from 0.5 to 20, or from 0.5 to 10, typically the alkyl alkoxylated sulphate is a $C_{8-18}$ alkyl ethoxylated sulphate having an average degree of ethoxylation of from 0.5 to 10, from 0.5 to 7, from 0.5 to 5 or from 0.5 to 3.

The alkyl sulphate, alkyl alkoxylated sulphate and alkyl benzene sulphonates may be linear or branched, substituted or un-substituted.

The detersive surfactant may be a mid-chain branched detersive surfactant, in one aspect, a mid-chain branched anionic detersive surfactant, in one aspect, a mid-chain branched alkyl sulphate and/or a mid-chain branched alkyl benzene sulphonate, e.g. a mid-chain branched alkyl sulphate. In one aspect, the mid-chain branches are $C_{1-4}$ alkyl groups, typically methyl and/or ethyl groups.

Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or soap, and combinations thereof.

Suitable non-ionic detersive surfactants are selected from the group consisting of: $C_8$-$C_{18}$ alkyl ethoxylates, such as, NEODOL®; $C_6$-$C_{12}$ alkyl phenol alkoxylates wherein the alkoxylate units may be ethyleneoxy units, propyleneoxy units or a mixture thereof; $C_{12}$-$C_{18}$ alcohol and $C_6$-$C_{12}$ alkyl phenol condensates with ethylene oxide/propylene oxide block polymers such as Pluronic®; $C_{14}$-$C_{22}$ mid-chain branched alcohols; $C_{14}$-$C_{22}$ mid-chain branched alkyl alkoxylates, typically having an average degree of alkoxylation of from 1 to 30; alkylpolysaccharides, in one aspect, alkylpolyglycosides; polyhydroxy fatty acid amides; ether capped poly(oxyalkylated) alcohol surfactants; and mixtures thereof.

Suitable non-ionic detersive surfactants include alkyl polyglucoside and/or an alkyl alkoxylated alcohol.

In one aspect, non-ionic detersive surfactants include alkyl alkoxylated alcohols, in one aspect $C_{8-18}$ alkyl alkoxylated alcohol, e.g. a $C_{8-18}$ alkyl ethoxylated alcohol, the alkyl alkoxylated alcohol may have an average degree of alkoxylation of from 1 to 50, from 1 to 30, from 1 to 20, or from 1 to 10. In one aspect, the alkyl alkoxylated alcohol may be a $C_{8-18}$ alkyl ethoxylated alcohol having an average degree of ethoxylation of from 1 to 10, from 1 to 7, more from 1 to 5 or from 3 to 7. The alkyl alkoxylated alcohol can be linear or branched, and substituted or un-substituted. Suitable nonionic surfactants include Lutensol®.

Non-limiting examples of nonionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA), as well as products available under the trade names SPAN and TWEEN, and combinations thereof.

Suitable cationic detersive surfactants include alkyl pyridinium compounds, alkyl quaternary ammonium compounds, alkyl quaternary phosphonium compounds, alkyl ternary sulphonium compounds, and mixtures thereof.

Suitable cationic detersive surfactants are quaternary ammonium compounds having the general formula: $(R)(R_1)(R_2)(R_3)N^+X^-$, wherein, R is a linear or branched, substituted or unsubstituted $C_{6-18}$ alkyl or alkenyl moiety, $R_1$ and $R_2$ are independently selected from methyl or ethyl moieties, $R_3$ is a hydroxyl, hydroxymethyl or a hydroxyethyl moiety, X is an anion which provides charge neutrality, suitable anions include: halides, e.g. chloride; sulphate; and sulphonate. Suitable cationic detersive surfactants are mono-$C_{6-18}$ alkyl mono-hydroxyethyl di-methyl quaternary ammonium chlorides. Highly suitable cationic detersive surfactants are mono-$C_{8-10}$ alkyl mono-hydroxyethyl di-methyl quaternary ammonium chloride, mono-$C_{10-12}$ alkyl mono-hydroxyethyl di-methyl quaternary ammonium chloride and mono-$C_{10}$ alkyl mono-hydroxyethyl di-methyl quaternary ammonium chloride.

Non-limiting examples of cationic surfactants include alkyldimethylethanolamine quat (ADMEAQ), cetyltrimethylammonium bromide (CTAB), dimethyldistearylammonium chloride (DSDMAC), and alkylbenzyldimethylammonium, alkyl quaternary ammonium compounds, alkoxylated quaternary ammonium (AQA) compounds, ester quats, and combinations thereof.

Suitable amphoteric/zwitterionic surfactants include amine oxides and betaines such as alkyldimethylbetaines, sulfobetaines, or combinations thereof. Amine-neutralized anionic surfactants—Anionic surfactants of the present invention and adjunct anionic cosurfactants, may exist in an acid form, and said acid form may be neutralized to form a surfactant salt which is desirable for use in the present detergent compositions. Typical agents for neutralization include the metal counterion base such as hydroxides, eg, NaOH or KOH. Further preferred agents for neutralizing anionic surfactants of the present invention and adjunct anionic surfactants or cosurfactants in their acid forms include ammonia, amines, or alkanolamines. Alkanolamines are preferred. Suitable non-limiting examples including monoethanolamine, diethanolamine, triethanolamine, and other linear or branched alkanolamines known in the art; e.g., highly preferred alkanolamines include 2-amino-1-propanol, 1-aminopropanol, monoisopropanolamine, or 1-amino-3-propanol. Amine neutralization may be done to a full or partial extent, e.g. part of the anionic surfactant mix may be neutralized with sodium or potassium and part of the anionic surfactant mix may be neutralized with amines or alkanolamines.

Non-limiting examples of semipolar surfactants include amine oxides (AO) such as alkyldimethylamineoxide Surfactant systems comprising mixtures of one or more anionic and in addition one or more nonionic surfactants optionally with an additional surfactant such as a cationic surfactant, may be preferred. Preferred weight ratios of anionic to nonionic surfactant are at least 2:1, or at least 1:1 to 1:10.

Soap—

The compositions herein may contain soap. Without being limited by theory, it may be desirable to include soap as it acts in part as a surfactant and in part as a builder and may be useful for suppression of foam and may furthermore interact favorably with the various cationic compounds of the composition to enhance softness on textile fabrics treaded with the inventive compositions. Any soap known in the art for use in laundry detergents may be utilized. In one embodiment, the compositions contain from 0 wt % to 20 wt %, from 0.5 wt % to 20 wt %, from 4 wt % to 10 wt %, or from 4 wt % to 7 wt % of soap.

Examples of soap useful herein include oleic acid soaps, palmitic acid soaps, palm kernel fatty acid soaps, and mixtures thereof. Typical soaps are in the form of mixtures of fatty acid soaps having different chain lengths and degrees of substitution. One such mixture is topped palm kernel fatty acid.

In one embodiment, the soap is selected from free fatty acid. Suitable fatty acids are saturated and/or unsaturated and can be obtained from natural sources such a plant or animal esters (e.g., palm kernel oil, palm oil, coconut oil, babassu oil, safflower oil, tall oil, castor oil, tallow and fish oils, grease, and mixtures thereof), or synthetically prepared (e.g., via the oxidation of petroleum or by hydrogenation of carbon monoxide via the Fisher Tropsch process).

Examples of suitable saturated fatty acids for use in the compositions of this invention include captic, lauric, myristic, palmitic, stearic, arachidic and behenic acid. Suitable unsaturated fatty acid species include: palmitoleic, oleic, linoleic, linolenic and ricinoleic acid. Examples of preferred fatty acids are saturated Cn fatty acid, saturated $C_{12}$-$C_{14}$ fatty acids, and saturated or unsaturated Cn to $C_{18}$ fatty acids, and mixtures thereof.

When present, the weight ratio of fabric softening cationic cosurfactant to fatty acid is preferably from about 1:3 to about 3:1, more preferably from about 1:1.5 to about 1.5:1, most preferably about 1:1.

Levels of soap and of nonsoap anionic surfactants herein are percentages by weight of the detergent composition, specified on an acid form basis. However, as is commonly understood in the art, anionic surfactants and soaps are in practice neutralized using sodium, potassium or alkanolammonium bases, such as sodium hydroxide or monoethanolamine.

Hydrotropes—

The compositions of the present invention may comprise one or more hydrotropes. A hydrotrope is a compound that solubilises hydrophobic compounds in aqueous solutions (or oppositely, polar substances in a non-polar environment). Typically, hydrotropes have both hydrophilic and a hydrophobic character (so-called amphiphilic properties as known from surfactants); however the molecular structure of hydrotropes generally do not favor spontaneous self-aggregation, see e.g. review by Hodgdon and Kaler (2007), Current Opinion in Colloid & Interface Science 12: 121-128. Hydrotropes do not display a critical concentration above which self-aggregation occurs as found for surfactants and lipids forming miceller, lamellar or other well defined mesophases. Instead, many hydrotropes show a continuous-type aggregation process where the sizes of aggregates grow as concentration increases. However, many hydrotropes alter the phase behavior, stability, and colloidal properties of systems containing substances of polar and non-polar character, including mixtures of water, oil, surfactants, and polymers. Hydrotropes are classically used across industries from pharma, personal care, food, to technical applications. Use of hydrotropes in detergent compositions allow for example more concentrated formulations of surfactants (as in the process of compacting liquid detergents by removing water) without inducing undesired phenomena such as phase separation or high viscosity.

The detergent may contain from 0 to 10 wt %, such as from 0 to 5 wt %, 0.5 to 5 wt %, or from 3% to 5 wt %, of a hydrotrope. Any hydrotrope known in the art for use in detergents may be utilized. Non-limiting examples of hydrotropes include sodium benzenesulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Builders—

The compositions of the present invention may comprise one or more builders, co-builders, builder systems or a mixture thereof. When a builder is used, the cleaning composition will typically comprise from 0 to 65 wt %, at least 1 wt %, from 2 to 60 wt % or from 5 to 10 wt % builder. In a dish wash cleaning composition, the level of builder is typically 40 to 65 wt % or 50 to 65 wt %. The composition may be substantially free of builder; substantially free means "no deliberately added" zeolite and/or phosphate. Typical zeolite builders include zeolite A, zeolite P and zeolite MAP. A typical phosphate builder is sodium tri-polyphosphate.

The builder and/or co-builder may particularly be a chelating agent that forms water-soluble complexes with Ca and Mg. Any builder and/or co-builder known in the art for use in detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), ethanolamines such as 2-aminoethan-1-ol (MEA), iminodiethanol (DEA) and 2,2',2"-nitrilotriethanol (TEA), and carboxymethylinulin (CMI), and combinations thereof.

The cleaning composition may include a co-builder alone, or in combination with a builder, e.g. a zeolite builder. Non-limiting examples of co-builders include homopolymers of polyacrylates or copolymers thereof, such as poly (acrylic acid) (PAA) or copoly(acrylic acid/maleic acid) (PAA/PMA). Further non-limiting examples include citrate, chelators such as aminocarboxylates, aminopolycarboxylates and phosphonates, and alkyl- or alkenylsuccinic acid. Additional specific examples include 2,2',2"-nitrilotriacetic acid (NTA), etheylenediaminetetraacetic acid (EDTA), diethylenetriaminepentaacetic acid (DTPA), iminodisuccinic acid (IDS), ethylenediamine-N,N'-disuccinic acid (EDDS), methylglycinediacetic acid (MGDA), glutamic acid-N,N-diacetic acid (GLDA), 1-hydroxyethane-1,1-diyl-bis(phosphonic acid) (HEDP), ethylenediaminetetrakis(methylene)tetrakis(phosphonic acid) (EDTMPA), diethylenetriaminepentakis(methylene)pentakis(phosphonic acid) (DTPMPA), N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfom-ethyl) aspartic acid (SMAS), N-(2-sulfoethyl) aspartic acid (SEAS), N-(2-sulfomethyl) glutamic acid (SMGL), N-(2-sulfoethyl) glutamic acid (SEGL), N-methyliminodiacetic acid (MIDA), α-alanine-N,N-diacetic acid (α-ALDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N, N-diacetic acid (SLDA), taurine-N, N-diacetic acid (TUDA) and sulfomethyl-N,N-diacetic acid (SMDA), N-(hydroxyethyl)-ethylidenediaminetriacetate (HEDTA), diethanolglycine (DEG), Diethylenetriamine Penta (Methylene Phosphonic acid) (DTPMP), aminotris(methylenephosphonic acid) (ATMP), and combinations and salts thereof. Further exemplary builders and/or co-builders are described in, e.g., WO09/102854, U.S. Pat. No. 5,977,053.

Chelating Agents and Crystal Growth Inhibitors—

The compositions herein may contain a chelating agent and/or a crystal growth inhibitor. Suitable molecules include copper, iron and/or manganese chelating agents and mixtures thereof. Suitable molecules include DTPA (Diethylene triamine pentaacetic acid), HEDP (Hydroxyethane diphosphonic acid), DTPMP (Diethylene triamine penta(methylene phosphonic acid)), 1,2-Dihydroxybenzene-3,5-disulfonic acid disodium salt hydrate, ethylenediamine, diethylene triamine, ethylenediaminedisuccinic acid (EDDS), N-hydroxyethylethylenediaminetri-acetic acid (HEDTA), triethylenetetraaminehexaacetic acid (TTHA), N-hydroxyethyl-iminodiacetic acid (HEIDA), dihydroxyethylglycine (DHEG), ethylenediaminetetrapropionic acid (EDTP), carboxymethyl inulin and 2-Phosphonobutane 1,2,4-tricarboxylic acid (Bayhibit® AM) and derivatives thereof. Typically the composition may comprise from 0.005 to 15 wt % or from 3.0 to 10 wt % chelating agent or crystal growth inhibitor.

Bleach Component—

The bleach component suitable for incorporation in the methods and compositions of the invention comprise one or a mixture of more than one bleach component. Suitable bleach components include bleaching catalysts, photobleaches, bleach activators, hydrogen peroxide, sources of hydrogen peroxide, pre-formed peracids and mixtures thereof. In general, when a bleach component is used, the compositions of the present invention may comprise from 0 to 30 wt %, from 0.00001 to 90 wt %, 0.0001 to 50 wt %, from 0.001 to 25 wt % or from 1 to 20 wt %. Examples of suitable bleach components include:

(1) Pre-formed peracids: Suitable preformed peracids include, but are not limited to, compounds selected from the group consisting of pre-formed peroxyacids or salts thereof, typically either a peroxycarboxylic acid or salt thereof, or a peroxysulphonic acid or salt thereof. The pre-formed peroxyacid or salt thereof is preferably a peroxycarboxylic acid or salt thereof, typically having a chemical structure corresponding to the following chemical formula:

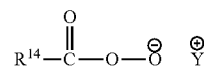

wherein: $R^{14}$ is selected from alkyl, aralkyl, cycloalkyl, aryl or heterocyclic groups; the $R^{14}$ group can be linear or branched, substituted or unsubstituted; and Y is any suitable counter-ion that achieves electric charge neutrality, preferably Y is selected from hydrogen, sodium or potassium. Preferably, $R^{14}$ is a linear or branched, substituted or unsubstituted $C_{6-9}$ alkyl. Preferably, the peroxyacid or salt thereof is selected from peroxyhexanoic acid, peroxyheptanoic acid, peroxyoctanoic acid, peroxynonanoic acid, peroxydecanoic acid, any salt thereof, or any combination thereof. Particularly preferred peroxyacids are phthalimido-peroxy-alkanoic acids, in particular e-phthahlimido peroxy hexanoic acid (PAP). Preferably, the peroxyacid or salt thereof has a melting point in the range of from 30° C. to 60° C.

The pre-formed peroxyacid or salt thereof can also be a peroxysulphonic acid or salt thereof, typically having a chemical structure corresponding to the following chemical formula:

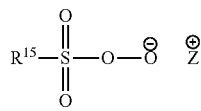

wherein: $R^{15}$ is selected from alkyl, aralkyl, cycloalkyl, aryl or heterocyclic groups; the $R^{15}$ group can be linear or branched, substituted or unsubstituted; and Z is any suitable counter-ion that achieves electric charge neutrality, preferably Z is selected from hydrogen, sodium or potassium. Preferably $R^{15}$ is a linear or branched, substituted or unsubstituted $C_{6-9}$ alkyl. Preferably such bleach components may be present in the compositions of the invention in an amount from 0.01 to 50 wt % or from 0.1 to 20 wt %.

(2) Sources of hydrogen peroxide include e.g., inorganic perhydrate salts, including alkali metal salts such as sodium salts of perborate (usually mono- or tetra-hydrate), percarbonate, persulphate, perphosphate, persilicate salts and mixtures thereof. In one aspect of the invention the inorganic perhydrate salts such as those selected from the group consisting of sodium salts of perborate, percarbonate and mixtures thereof. When employed, inorganic perhydrate salts are typically present in amounts of 0.05 to 40 wt % or 1 to 30 wt % of the overall composition and are typically incorporated into such compositions as a crystalline solid that may be coated. Suitable coatings include: inorganic salts such as alkali metal silicate, carbonate or borate salts or mixtures thereof, or organic materials such as water-soluble or dispersible polymers, waxes, oils or fatty soaps. Preferably such bleach components may be present in the compositions of the invention in an amount of 0.01 to 50 wt % or 0.1 to 20 wt %.

(3) The term bleach activator is meant herein as a compound which reacts with hydrogen peroxide to form a peracid via perhydrolysis. The peracid thus formed constitutes the activated bleach. Suitable bleach activators to be used herein include those belonging to the class of esters, amides, imides or anhydrides. Suitable bleach activators are those having R—(C═O)-L wherein R is an alkyl group, optionally branched, having, when the bleach activator is hydrophobic, from 6 to 14 carbon atoms, or from 8 to 12 carbon atoms and, when the bleach activator is hydrophilic, less than 6 carbon atoms or less than 4 carbon atoms; and L is leaving group. Examples of suitable leaving groups are benzoic acid and derivatives thereof—especially benzene sulphonate. Suitable bleach activators include dodecanoyl oxybenzene sulphonate, decanoyl oxybenzene sulphonate, decanoyl oxybenzoic acid or salts thereof, 3,5,5-trimethyl hexanoyloxybenzene sulphonate, tetraacetyl ethylene diamine (TAED), sodium 4-[(3,5,5-trimethylhexanoyl)oxy] benzene-1-sulfonate (ISONOBS), 4-(dodecanoyloxy)benzene-1-sulfonate (LOBS), 4-(decanoyloxy)benzene-1-sulfonate, 4-(decanoyloxy)benzoate (DOBS or DOBA), 4-(nonanoyloxy)benzene-1-sulfonate (NOBS), and/or those disclosed in WO98/17767. A family of bleach activators is disclosed in EP624154 and particularly preferred in that family is acetyl triethyl citrate (ATC). ATC or a short chain triglyceride like triacetin has the advantage that it is environmentally friendly. Furthermore acetyl triethyl citrate and triacetin have good hydrolytical stability in the product upon storage and are efficient bleach activators. Finally ATC is multifunctional, as the citrate released in the perhydrolysis reaction may function as a builder. Alternatively, the bleaching system may comprise peroxyacids of, for example, the amide, imide, or sulfone type. The bleaching system may also comprise peracids such as 6-(phthalimido)peroxyhexanoic acid (PAP). Suitable bleach activators are also disclosed in WO98/17767. While any suitable bleach activator may be employed, in one aspect of the invention the subject cleaning composition may comprise NOBS, TAED or mixtures thereof. When present, the peracid and/or bleach activator is generally present in the composition in an amount of 0.1 to 60 wt %, 0.5 to 40 wt % or 0.6 to 10 wt % based on the fabric and home care composition. One or more hydrophobic peracids or precursors thereof may be used in combination with one or more hydrophilic peracid or precursor thereof. Preferably such bleach components may be present in the compositions of the invention in an amount of 0.01 to 50 wt %, or 0.1 to 20 wt %.

The amounts of hydrogen peroxide source and peracid or bleach activator may be selected such that the molar ratio of available oxygen (from the peroxide source) to peracid is from 1:1 to 35:1, or even 2:1 to 10:1.

(4) Diacyl peroxides—preferred diacyl peroxide bleaching species include those selected from diacyl peroxides of the general formula: $R^1$—C(O)—OO—(O)C—$R^2$, in which $R^1$ represents a $C_6$-$C_{18}$ alkyl, preferably $C_6$-$C_{12}$ alkyl group containing a linear chain of at least 5 carbon atoms and optionally containing one or more substituents (e.g. —N$^+$(CH$_3$)$_3$, —COOH or —CN) and/or one or more interrupting moieties (e.g. —CONH— or —CH═CH—) interpolated between adjacent carbon atoms of the alkyl radical, and $R^2$ represents an aliphatic group compatible with a peroxide moiety, such that $R^1$ and $R^2$ together contain a total of 8 to 30 carbon atoms. In one preferred aspect $R^1$ and $R^2$ are linear unsubstituted $C_6$-$C_{12}$ alkyl chains. Most preferably $R^1$ and $R^2$ are identical. Diacyl peroxides, in which both $R^1$ and $R^2$ are $C_6$-$C_{12}$ alkyl groups, are particularly preferred. Preferably, at least one of, most preferably only one of, the R groups ($R_1$ or $R_2$), does not contain branching or pendant rings in the alpha position, or preferably neither in the alpha nor beta positions or most preferably in none of the alpha or beta or gamma positions. In one further preferred embodiment the DAP may be asymmetric, such that preferably the hydrolysis of R1 acyl group is rapid to generate peracid, but the hydrolysis of R2 acyl group is slow.

The tetraacyl peroxide bleaching species is preferably selected from tetraacyl peroxides of the general formula: $R^3$—C(O)—OO—C(O)—(CH$_2$)n-C(O)—OO—C(O)—$R^3$, in which $R^3$ represents a $C_1$-$C_9$ alkyl, or $C_3$-07, group and n represents an integer from 2 to 12, or 4 to 10 inclusive.

Preferably, the diacyl and/or tetraacyl peroxide bleaching species is present in an amount sufficient to provide at least 0.5 ppm, at least 10 ppm, or at least 50 ppm by weight of the wash liquor. In a preferred embodiment, the bleaching species is present in an amount sufficient to provide from 0.5 to 300 ppm, from 30 to 150 ppm by weight of the wash liquor. Preferably the bleach component comprises a bleach catalyst (5 and 6).

(5) Preferred are organic (non-metal) bleach catalysts include bleach catalyst capable of accepting an oxygen atom from a peroxyacid and/or salt thereof, and transferring the oxygen atom to an oxidizeable substrate. Suitable bleach catalysts include, but are not limited to: iminium cations and polyions; iminium zwitterions; modified amines; modified amine oxides; N-sulphonyl imines; N-phosphonyl imines; N-acyl imines; thiadiazole dioxides; perfluoroimines; cyclic sugar ketones and mixtures thereof.

Suitable iminium cations and polyions include, but are not limited to, N-methyl-3,4-dihydroisoquinolinium tetrafluoroborate, prepared as described in Tetrahedron (1992), 49(2), 423-38 (e.g. compound 4, p. 433); N-methyl-3,4-dihydroisoquinolinium p-toluene sulphonate, prepared as described in U.S. Pat. No. 5,360,569 (e.g. Column 11, Example 1); and N-octyl-3,4-dihydroisoquinolinium p-toluene sulphonate, prepared as described in U.S. Pat. No. 5,360,568 (e.g. Column 10, Ex. 3).

Suitable iminium zwitterions include, but are not limited to, N-(3-sulfopropyl)-3,4-dihydroisoquinolinium, inner salt, prepared as described in U.S. Pat. No. 5,576,282 (e.g. Column 31, Ex. II); N-[2-(sulphooxy)dodecyl]-3,4-dihydroisoquinolinium, inner salt, prepared as described in U.S. Pat. No. 5,817,614 (e.g. Column 32, Ex. V); 2-[3-[(2-ethylhexyl)oxy]-2-(sulphooxy)propyl]-3,4-dihydroisoquinolinium, inner salt, prepared as described in WO05/047264 (e.g. p. 18, Ex. 8), and 2-[3-[(2-butyloctyl)oxy]-2-(sulphooxy)propyl]-3,4-dihydroisoquinolinium, inner salt.

Suitable modified amine oxygen transfer catalysts include, but are not limited to, 1,2,3,4-tetrahydro-2-methyl-1-isoquinolinol, which can be made according to the procedures described in Tetrahedron Letters (1987), 28(48), 6061-6064. Suitable modified amine oxide oxygen transfer catalysts include, but are not limited to, sodium 1-hydroxy-N-oxy-N-[2-(sulphooxy)decyl]-1,2,3,4-tetrahydroisoquinoline.

Suitable N-sulphonyl imine oxygen transfer catalysts include, but are not limited to, 3-methyl-1,2-benzisothiazole 1,1-dioxide, prepared according to the procedure described in the Journal of Organic Chemistry (1990), 55(4), 1254-61.

Suitable N-phosphonyl imine oxygen transfer catalysts include, but are not limited to, [R-(E)]—N-[(2-chloro-5-nitrophenyl)methylene]-P-phenyl-P-(2,4,6-trimethylphenyl)-phosphinic amide, which can be made according to the procedures described in the Journal of the Chemical Society, Chemical Communications (1994), (22), 2569-70.

Suitable N-acyl imine oxygen transfer catalysts include, but are not limited to, [N(E)]—N-(phenylmethylene)acetamide, which can be made according to the procedures described in Polish Journal of Chemistry (2003), 77(5), 577-590.

Suitable thiadiazole dioxide oxygen transfer catalysts include but are not limited to, 3-methyl-4-phenyl-1,2,5-thiadiazole 1,1-dioxide, which can be made according to the procedures described in U.S. Pat. No. 5,753,599 (Column 9, Ex. 2).

Suitable perfluoroimine oxygen transfer catalysts include, but are not limited to, (Z)-2,2,3,3,4,4,4-heptafluoro-N-(nonafluorobutyl)butanimidoyl fluoride, which can be made according to the procedures described in Tetrahedron Letters (1994), 35(34), 6329-30.

Suitable cyclic sugar ketone oxygen transfer catalysts include, but are not limited to, 1,2:4,5-di-O-isopropylidene-D-erythro-2,3-hexodiuro-2,6-pyranose as prepared in U.S. Pat. No. 6,649,085 (Column 12, Ex. 1).

Preferably, the bleach catalyst comprises an iminium and/or carbonyl functional group and is typically capable of forming an oxaziridinium and/or dioxirane functional group upon acceptance of an oxygen atom, especially upon acceptance of an oxygen atom from a peroxyacid and/or salt thereof. Preferably, the bleach catalyst comprises an oxaziridinium functional group and/or is capable of forming an oxaziridinium functional group upon acceptance of an oxygen atom, especially upon acceptance of an oxygen atom from a peroxyacid and/or salt thereof. Preferably, the bleach catalyst comprises a cyclic iminium functional group, preferably wherein the cyclic moiety has a ring size of from five to eight atoms (including the nitrogen atom), preferably six atoms. Preferably, the bleach catalyst comprises an aryliminium functional group, preferably a bi-cyclic aryliminium functional group, preferably a 3,4-dihydroisoquinolinium functional group. Typically, the imine functional group is a quaternary imine functional group and is typically capable of forming a quaternary oxaziridinium functional group upon acceptance of an oxygen atom, especially upon acceptance of an oxygen atom from a peroxyacid and/or salt thereof. In another aspect, the detergent composition comprises a bleach component having a $\log P_{o/w}$ no greater than 0, no greater than $-0.5$, no greater than $-1.0$, no greater than $-1.5$, no greater than $-2.0$, no greater than $-2.5$, no greater than $-3.0$, or no greater than $-3.5$. The method for determining $\log P_{o/w}$ is described in more detail below.

Typically, the bleach ingredient is capable of generating a bleaching species having a $X_{SO}$ of from 0.01 to 0.30, from 0.05 to 0.25, or from 0.10 to 0.20. The method for determining $X_{SO}$ is described in more detail below. For example, bleaching ingredients having an isoquinolinium structure are capable of generating a bleaching species that has an oxaziridinium structure. In this example, the $X_{SO}$ is that of the oxaziridinium bleaching species.

Preferably, the bleach catalyst has a chemical structure corresponding to the following chemical formula:

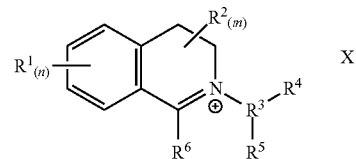

wherein: n and m are independently from 0 to 4, preferably n and m are both 0; each $R^1$ is independently selected from a substituted or unsubstituted radical selected from the group consisting of hydrogen, alkyl, cycloalkyl, aryl, fused aryl, heterocyclic ring, fused heterocyclic ring, nitro, halo, cyano, sulphonato, alkoxy, keto, carboxylic, and carboalkoxy radicals; and any two vicinal $R^1$ substituents may combine to form a fused aryl, fused carbocyclic or fused heterocyclic ring; each $R^2$ is independently selected from a substituted or unsubstituted radical independently selected from the group consisting of hydrogen, hydroxy, alkyl, cycloalkyl, alkaryl, aryl, aralkyl, alkylenes, heterocyclic ring, alkoxys, arylcarbonyl groups, carboxyalkyl groups and amide groups; any $R^2$ may be joined together with any other of $R^2$ to form part of a common ring; any geminal $R^2$ may combine to form a carbonyl; and any two $R^2$ may combine to form a substituted or unsubstituted fused unsaturated moiety; $R^3$ is a $C_1$ to $C_{20}$ substituted or unsubstituted alkyl; $R^4$ is hydrogen or the moiety Qt-A, wherein: Q is a branched or unbranched alkylene, t=0 or 1 and A is an anionic group selected from the group consisting of $OSO_3^-$, $SO_3^-$, $CO_2^-$, $OCO_2^-$, $OPO_3^{2-}$, $OPO_3H^-$ and $OPO_2^-$; $R^5$ is hydrogen or the moiety —CR$^{11}$R$^{12}$—Y-G$_b$-Y$_c$—[(CR$^9$R$^{10}$)$_y$—O]$_k$—R$^8$, wherein: each Y is independently selected from the group consisting of O, S, N—H, or N—R$^8$; and each R$^8$ is independently selected from the group consisting of alkyl, aryl and heteroaryl, said moieties being substituted or unsubstituted, and whether substituted or unsubstituted said moieties having less than 21 carbons; each G is independently selected from the group consisting of CO, SO$_2$, SO, PO and PO$_2$; R$^9$ and R$^{10}$ are independently selected from the group consisting of H and C$_1$-C$_4$ alkyl; R$^{11}$ and R$^{12}$ are independently selected from the group consisting of H and alkyl, or when taken together may join to form a carbonyl; b=0 or 1; c can =0 or 1, but c must =0 if b=0; y is an integer from 1 to 6; k is an integer from 0 to 20; R$^6$ is H, or an alkyl, aryl or heteroaryl moiety; said moieties being substituted or unsubstituted; and X, if present, is a suitable charge balancing counterion, preferably X is present when R$^4$ is hydrogen, suitable X, include but are not limited to: chloride, bromide, sulphate, methosulphate, sulphonate, p-toluenesulphonate, borontetraflouride and phosphate.

In one embodiment of the present invention, the bleach catalyst has a structure corresponding to general formula below:

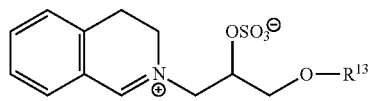

wherein R$^{13}$ is a branched alkyl group containing from three to 24 carbon atoms (including the branching carbon atoms) or a linear alkyl group containing from one to 24 carbon atoms; preferably R$^{13}$ is a branched alkyl group containing from eight to 18 carbon atoms or linear alkyl group containing from eight to eighteen carbon atoms; preferably R$^{13}$ is selected from the group consisting of 2-propylheptyl, 2-butyloctyl, 2-pentylnonyl, 2-hexyldecyl, n-dodecyl, n-tetradecyl, n-hexadecyl, n-octadecyl, iso-nonyl, iso-decyl, iso-tridecyl and iso-pentadecyl; preferably R$^{13}$ is selected from the group consisting of 2-butyloctyl, 2-pentylnonyl, 2-hexyldecyl, iso-tridecyl and iso-pentadecyl.

Preferably the bleach component comprises a source of peracid in addition to bleach catalyst, particularly organic bleach catalyst. The source of peracid may be selected from (a) pre-formed peracid; (b) percarbonate, perborate or persulfate salt (hydrogen peroxide source) preferably in combination with a bleach activator; and (c) perhydrolase enzyme and an ester for forming peracid in situ in the presence of water in a textile or hard surface treatment step. When present, the peracid and/or bleach activator is generally present in the composition in an amount of from 0.1 to 60 wt %, from 0.5 to 40 wt % or from 0.6 to 10 wt % based on the composition. One or more hydrophobic peracids or precursors thereof may be used in combination with one or more hydrophilic peracid or precursor thereof.

The amounts of hydrogen peroxide source and peracid or bleach activator may be selected such that the molar ratio of available oxygen (from the peroxide source) to peracid is from 1:1 to 35:1, or 2:1 to 10:1.

(6) Metal-containing Bleach Catalysts—The bleach component may be provided by a catalytic metal complex. One type of metal-containing bleach catalyst is a catalyst system comprising a transition metal cation of defined bleach catalytic activity, such as copper, iron, titanium, ruthenium, tungsten, molybdenum, or manganese cations, an auxiliary metal cation having little or no bleach catalytic activity, such as zinc or aluminum cations, and a sequestrate having defined stability constants for the catalytic and auxiliary metal cations, particularly ethylenediaminetetraacetic acid, ethylenediaminetetra(methylenephosphonic acid) and water-soluble salts thereof. Such catalysts are disclosed in U.S. Pat. No. 4,430,243. Preferred catalysts are described in WO09/839406, U.S. Pat. No. 6,218,351 and WO00/012667. Particularly preferred are transition metal catalyst or ligands therefore that are cross-bridged polydentate N-donor ligands.

If desired, the compositions herein can be catalyzed by means of a manganese compound. Such compounds and levels of use are well known in the art and include, e.g., the manganese-based catalysts disclosed in U.S. Pat. No. 5,576,282.

Cobalt bleach catalysts useful herein are known, and are described e.g. in U.S. Pat. Nos. 5,597,936; 5,595,967. Such cobalt catalysts are readily prepared by known procedures, such as taught e.g. in U.S. Pat. Nos. 5,597,936 and 5,595,967.

Compositions herein may also suitably include a transition metal complex of ligands such as bispidones (U.S. Pat. No. 7,501,389) and/or macropolycyclic rigid ligands—abbreviated as "MRLs". As a practical matter, and not by way of limitation, the compositions and processes herein can be adjusted to provide on the order of at least one part per hundred million of the active MRL species in the aqueous washing medium, and will typically provide from 0.005 to 25 ppm, from 0.05 to 10 ppm, or from 0.1 to 5 ppm, of the MRL in the wash liquor.

Suitable transition-metals in the instant transition-metal bleach catalyst include e.g. manganese, iron and chromium. Suitable MRLs include 5,12-diethyl-1,5,8,12-tetraazabicyclo[6.6.2]hexadecane. Suitable transition metal MRLs are readily prepared by known procedures, such as taught e.g. in U.S. Pat. No. 6,225,464 and WO00/32601.

(7) Photobleaches—suitable photobleaches include e.g. sulfonated zinc phthalocyanine sulfonated aluminium phthalocyanines, xanthene dyes and mixtures thereof. Preferred bleach components for use in the present compositions of the invention comprise a hydrogen peroxide source, bleach activator and/or organic peroxyacid, optionally generated in situ by the reaction of a hydrogen peroxide source and bleach activator, in combination with a bleach catalyst. Preferred bleach components comprise bleach catalysts, preferably organic bleach catalysts, as described above.

Particularly preferred bleach components are the bleach catalysts in particular the organic bleach catalysts.

Exemplary bleaching systems are also described, e.g. in WO2007/087258, WO2007/087244, WO2007/087259 and WO2007/087242.

Fabric Hueing Agents—

The composition may comprise a fabric hueing agent. Suitable fabric hueing agents include dyes, dye-clay conjugates, and pigments. Suitable dyes include small molecule dyes and polymeric dyes. Suitable small molecule dyes include small molecule dyes selected from the group consisting of dyes falling into the Color Index (C.I.) classifications of Direct Blue, Direct Red, Direct Violet, Acid Blue, Acid Red, Acid Violet, Basic Blue, Basic Violet and Basic Red, or mixtures thereof.

In another aspect, suitable small molecule dyes include small molecule dyes selected from the group consisting of Color Index (Society of Dyers and Colorists, Bradford, UK) numbers Direct Violet 9, Direct Violet 35, Direct Violet 48, Direct Violet 51, Direct Violet 66, Direct Violet 99, Direct Blue 1, Direct Blue 71, Direct Blue 80, Direct Blue 279, Acid Red 17, Acid Red 73, Acid Red 88, Acid Red 150, Acid Violet 15, Acid Violet 17, Acid Violet 24, Acid Violet 43, Acid Red 52, Acid Violet 49, Acid Violet 50, Acid Blue 15, Acid Blue 17, Acid Blue 25, Acid Blue 29, Acid Blue 40, Acid Blue 45, Acid Blue 75, Acid Blue 80, Acid Blue 83, Acid Blue 90 and Acid Blue 113, Acid Black 1, Basic Violet 1, Basic Violet 3, Basic Violet 4, Basic Violet 10, Basic Violet 35, Basic Blue 3, Basic Blue 16, Basic Blue 22, Basic Blue 47, Basic Blue 66, Basic Blue 75, Basic Blue 159 and mixtures thereof. In another aspect, suitable small molecule dyes include small molecule dyes selected from the group consisting of Color Index (Society of Dyers and Colorists, Bradford, UK) numbers Acid Violet 17, Acid Violet 43, Acid Red 52, Acid Red 73, Acid Red 88, Acid Red 150, Acid Blue 25, Acid Blue 29, Acid Blue 45, Acid Blue 113, Acid Black 1, Direct Blue 1, Direct Blue 71, Direct Violet 51 and mixtures thereof. In another aspect, suitable small molecule dyes include small molecule dyes selected from the group consisting of Color Index (Society of Dyers and Colorists, Bradford, UK) numbers Acid Violet 17, Direct Blue 71, Direct Violet 51, Direct Blue 1, Acid Red 88, Acid Red 150, Acid Blue 29, Acid Blue 113 or mixtures thereof.

Suitable polymeric dyes include polymeric dyes selected from the group consisting of polymers containing conjugated chromogens (dye-polymer conjugates) and polymers with chromogens co-polymerized into the backbone of the polymer and mixtures thereof.

In another aspect, suitable polymeric dyes include polymeric dyes selected from the group consisting of fabric-substantive colorants sold under the name of Liquitint® (Milliken), dye-polymer conjugates formed from at least one reactive dye and a polymer selected from the group consisting of polymers comprising a moiety selected from the group consisting of a hydroxyl moiety, a primary amine moiety, a secondary amine moiety, a thiol moiety and mixtures thereof. In still another aspect, suitable polymeric dyes include polymeric dyes selected from the group consisting of Liquitint® Violet CT, carboxymethyl cellulose (CMC) conjugated with a reactive blue, reactive violet or reactive red dye such as CMC conjugated with C.I. Reactive Blue 19, sold by Megazyme, Wicklow, Ireland under the product name AZO-CM-CELLULOSE, product code S-ACMC, alkoxylated triphenyl-methane polymeric colorants, alkoxylated thiophene polymeric colorants, and mixtures thereof.

Preferred hueing dyes include the whitening agents found in WO008/87497. These whitening agents may be characterized by the following structure (I):

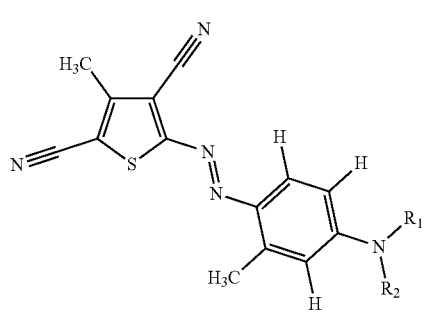

wherein $R_1$ and $R_2$ can independently be selected from:
a) $[(CH_2CR'HO)_x(CH_2CR''HO)_yH]$ wherein R' is selected from the group consisting of H, $CH_3$, $CH_2O(CH_2CH_2O)_zH$, and mixtures thereof; wherein R" is selected from the group consisting of H, $CH_2O(CH_2CH_2O)_zH$, and mixtures thereof; wherein $x+y \leq 5$; wherein $y \geq 1$; and wherein $z=0$ to 5;

b) $R_1$=alkyl, aryl or aryl alkyl and $R_2=[(CH_2CR'HO)_x(CH_2CR''HO)_yH]$
wherein R' is selected from the group consisting of H, $CH_3$, $CH_2O(CH_2CH_2O)_zH$, and mixtures thereof; wherein R" is selected from the group consisting of H, $CH_2O(CH_2CH_2O)_zH$, and mixtures thereof; wherein $x+y \leq 10$; wherein $y \geq 1$; and wherein $z=0$ to 5;

c) $R_1=[CH_2CH_2(OR_3)CH_2OR_4]$ and $R_2=[CH_2CH_2(OR_3)CH_2O R_4]$
wherein $R_3$ is selected from the group consisting of H, $(CH_2CH_2O)_zH$, and mixtures thereof; and wherein $z=0$ to 10;
wherein $R_4$ is selected from the group consisting of ($C_1$-$C_{16}$)alkyl, aryl groups, and mixtures thereof; and d) wherein R1 and R2 can independently be selected from the amino addition product of styrene oxide, glycidyl methyl ether, isobutyl glycidyl ether, isopropylglycidyl ether, t-butyl glycidyl ether, 2-ethylhexylgycidyl ether, and glycidylhexadecyl ether, followed by the addition of from 1 to 10 alkylene oxide units.

A preferred whitening agent of the present invention may be characterized by the following structure (II):

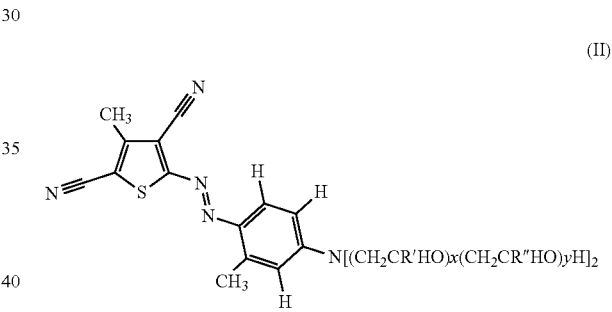

wherein R' is selected from the group consisting of H, $CH_3$, $CH_2O(CH_2CH_2O)_zH$, and mixtures thereof; wherein R" is selected from the group consisting of H, $CH_2O(CH_2CH_2O)_zH$, and mixtures thereof; wherein $x+y \leq 5$; wherein $y \geq 1$; and wherein $z=0$ to 5.

A further preferred whitening agent of the present invention may be characterized by the following structure (III):

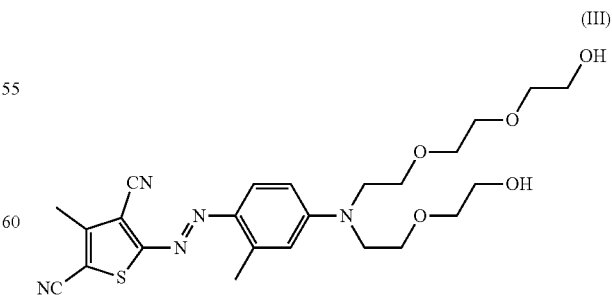

typically comprising a mixture having a total of 5 EO groups. Suitable preferred molecules are those in Structure I having the following pendant groups in "part a" above.

TABLE A

| | R1 | | | | R2 | | | |
|---|---|---|---|---|---|---|---|---|
| | R' | R" | x | y | R' | R" | x | y |
| A | H | H | 3 | 1 | H | H | 0 | 1 |
| B | H | H | 2 | 1 | H | H | 1 | 1 |
| c = b | H | H | 1 | 1 | H | H | 2 | 1 |
| d = a | H | H | 0 | 1 | H | H | 3 | 1 |

Further whitening agents of use include those described in US2008/34511 (Unilever). A preferred agent is "Violet 13".

Suitable dye clay conjugates include dye clay conjugates selected from the group comprising at least one cationic/basic dye and a smectite clay, and mixtures thereof. In another aspect, suitable dye clay conjugates include dye clay conjugates selected from the group consisting of one cationic/basic dye selected from the group consisting of C.I. Basic Yellow 1 through 108, C.I. Basic Orange 1 through 69, C.I. Basic Red 1 through 118, C.I. Basic Violet 1 through 51, C.I. Basic Blue 1 through 164, C.I. Basic Green 1 through 14, C.I. Basic Brown 1 through 23, CI Basic Black 1 through 11, and a clay selected from the group consisting of Montmorillonite clay, Hectorite clay, Saponite clay and mixtures thereof. In still another aspect, suitable dye clay conjugates include dye clay conjugates selected from the group consisting of: Montmorillonite Basic Blue B7 C.I. 42595 conjugate, Montmorillonite Basic Blue B9 C.I. 52015 conjugate, Montmorillonite Basic Violet V3 C.I. 42555 conjugate, Montmorillonite Basic Green G1 C.I. 42040 conjugate, Montmorillonite Basic Red R1 C.I. 45160 conjugate, Montmorillonite C.I. Basic Black 2 conjugate, Hectorite Basic Blue B7 C.I. 42595 conjugate, Hectorite Basic Blue B9 C.I. 52015 conjugate, Hectorite Basic Violet V3 C.I. 42555 conjugate, Hectorite Basic Green G1 C.I. 42040 conjugate, Hectorite Basic Red R1 C.I. 45160 conjugate, Hectorite C.I. Basic Black 2 conjugate, Saponite Basic Blue B7 C.I. 42595 conjugate, Saponite Basic Blue B9 C.I. 52015 conjugate, Saponite Basic Violet V3 C.I. 42555 conjugate, Saponite Basic Green G1 C.I. 42040 conjugate, Saponite Basic Red R1 C.I. 45160 conjugate, Saponite C.I. Basic Black 2 conjugate and mixtures thereof.

Suitable pigments include pigments selected from the group consisting of flavanthrone, indanthrone, chlorinated indanthrone containing from 1 to 4 chlorine atoms, pyranthrone, dichloropyranthrone, monobromodichloropyranthrone, dibromodichloropyranthrone, tetrabromopyranthrone, perylene-3,4,9,10-tetracarboxylic acid diimide, wherein the imide groups may be unsubstituted or substituted by C1-C3-alkyl or a phenyl or heterocyclic radical, and wherein the phenyl and heterocyclic radicals may additionally carry substituents which do not confer solubility in water, anthrapyrimidinecarboxylic acid amides, violanthrone, isoviolanthrone, dioxazine pigments, copper phthalocyanine which may contain up to 2 chlorine atoms per molecule, polychloro-copper phthalocyanine or polybromochloro-copper phthalocyanine containing up to 14 bromine atoms per molecule and mixtures thereof.
In another aspect, suitable pigments include pigments selected from the group consisting of Ultramarine Blue (C.I. Pigment Blue 29), Ultramarine Violet (C.I. Pigment Violet 15) and mixtures thereof.

The aforementioned fabric hueing agents can be used in combination (any mixture of fabric hueing agents can be used). Suitable hueing agents are described in more detail in U.S. Pat. No. 7,208,459. Preferred levels of dye in compositions of the invention are 0.00001 to 0.5 wt %, or 0.0001 to 0.25 wt %. The concentration of dyes preferred in water for the treatment and/or cleaning step is from 1 ppb to 5 ppm, 10 ppb to 5 ppm or 20 ppb to 5 ppm. In preferred compositions, the concentration of surfactant will be from 0.2 to 3 g/l.

Encapsulates—

The composition may comprise an encapsulate. In one aspect, an encapsulate comprising a core, a shell having an inner and outer surface, said shell encapsulating said core.

In one aspect of said encapsulate, said core may comprise a material selected from the group consisting of perfumes; brighteners; dyes; insect repellants; silicones; waxes; flavors; vitamins; fabric softening agents; skin care agents in one aspect, paraffins; enzymes; anti-bacterial agents; bleaches; sensates; and mixtures thereof; and said shell may comprise a material selected from the group consisting of polyethylenes; polyamides; polyvinylalcohols, optionally containing other co-monomers; polystyrenes; polyisoprenes; polycarbonates; polyesters; polyacrylates; aminoplasts, in one aspect said aminoplast may comprise a polyureas, polyurethane, and/or polyureaurethane, in one aspect said polyurea may comprise polyoxymethyleneurea and/or melamine formaldehyde; polyolefins; polysaccharides, in one aspect said polysaccharide may comprise alginate and/or or chitosan; gelatin; shellac; epoxy resins; vinyl polymers; water insoluble inorganics; silicone; and mixtures thereof.

In one aspect of said encapsulate, said core may comprise perfume.

In one aspect of said encapsulate, said shell may comprise melamine formaldehyde and/or cross linked melamine formaldehyde.

In a one aspect, suitable encapsulates may comprise a core material and a shell, said shell at least partially surrounding said core material, is disclosed. 85% or 90% of said encapsulates may have a fracture strength of from 0.2 to 10 MPa, from 0.4 to 5 MPa, from 0.6 to 3.5 MPa, or from 0.7 to 3 MPa; and a benefit agent leakage of from 0 to 30%, from 0 to 20%, or from 0 to 5%.

In one aspect, 85% or 90% of said encapsulates may have a particle size from 1 to 80 microns, from 5 to 60 microns, from 10 to 50 microns, or from 15 to 40 microns.

In one aspect, 85% or 90% of said encapsulates may have a particle wall thickness from 30 to 250 nm, from 80 to 180 nm, or from 100 to 160 nm.

In one aspect, said encapsulates' core material may comprise a material selected from the group consisting of a perfume raw material and/or optionally a material selected from the group consisting of vegetable oil, including neat and/or blended vegetable oils including castor oil, coconut oil, cottonseed oil, grape oil, rapeseed, soybean oil, corn oil, palm oil, linseed oil, safflower oil, olive oil, peanut oil, coconut oil, palm kernel oil, castor oil, lemon oil and mixtures thereof; esters of vegetable oils, esters, including dibutyl adipate, dibutyl phthalate, butyl benzyl adipate, benzyl octyl adipate, tricresyl phosphate, trioctyl phosphate and mixtures thereof; straight or branched chain hydrocarbons, including those straight or branched chain hydrocarbons having a boiling point of greater than about 80° C.; partially hydrogenated terphenyls, dialkyl phthalates, alkyl biphenyls, including monoisopropylbiphenyl, alkylated naphthalene, including dipropylnaphthalene, petroleum spirits, including kerosene, mineral oil and mixtures thereof; aromatic solvents, including benzene, toluene and mixtures thereof; silicone oils; and mixtures thereof.

In one aspect, said encapsulates' wall material may comprise a suitable resin including the reaction product of an aldehyde and an amine, suitable aldehydes include, formaldehyde. Suitable amines include melamine, urea, benzoguanamine, glycoluril, and mixtures thereof. Suitable melamines include methylol melamine, methylated methylol melamine, imino melamine and mixtures thereof. Suitable ureas include dimethylol urea, methylated dimethylol urea, urea-resorcinol, and mixtures thereof.

In one aspect, suitable formaldehyde scavengers may be employed with the encapsulates e.g. in a capsule slurry and/or added to a composition before, during or after the encapsulates are added to such composition. Suitable capsules may be made by the following teaching of US2008/0305982; and/or US2009/0247449.

In a preferred aspect the composition can also comprise a deposition aid, preferably consisting of the group comprising cationic or nonionic polymers. Suitable polymers include cationic starches, cationic hydroxyethylcellulose, polyvinylformaldehyde, locust bean gum, mannans, xyloglucans, tamarind gum, polyethyleneterephthalate and polymers containing dimethylaminoethyl methacrylate, optionally with one or monomers selected from the group comprising acrylic acid and acrylamide.

Perfumes—

In one aspect the composition comprises a perfume that comprises one or more perfume raw materials selected from the group consisting of 1,1'-oxybis-2-propanol; 1,4-cyclohexanedicarboxylic acid, diethyl ester; (ethoxymethoxy)cyclododecane; 1,3-nonanediol, monoacetate; (3-methylbutoxy)acetic acid, 2-propenyl ester; beta-methyl cyclododecaneethanol; 2-methyl-3-[(1,7,7-trimethylbicyclo[2.2.1]hept-2-yl)oxy]-1-propanol; oxacyclohexadecan-2-one; alpha-methyl-benzenemethanol acetate; trans-3-ethoxy-1,1,5-trimethylcyclohexane; 4-(1,1-dimethylethyl)cyclohexanol acetate; dodecahydro-3a,6,6,9a-tetramethylnaphtho[2,1-b]furan; beta-methyl benzenepropanal; beta-methyl-3-(1-methylethyl)benzenepropanal; 4-phenyl-2-butanone; 2-methylbutanoic acid, ethyl ester; benzaldehyde; 2-methylbutanoic acid, 1-methylethyl ester; dihydro-5-pentyl-2(3H)furanone; (2E)-1-(2,6,6-trimethyl-2-cyclohexen-1-yl)-2-buten-1-one; dodecanal; undecanal; 2-ethyl-alpha, alpha-dimethylbenzenepropanal; decanal; alpha, alpha-dimethylbenzeneethanol acetate; 2-(phenylmethylene)octanal; 2-[[3-[4-(1,1-dimethylethyl)phenyl]-2-methylpropylidene]amino]benzoic acid, methyl ester; 1-(2,6,6-trimethyl-3-cyclohexen-1-yl)-2-buten-1-one; 2-pentylcyclopentanone; 3-oxo-2-pentyl cyclopentaneacetic acid, methyl ester; 4-hydroxy-3-methoxybenzaldehyde; 3-ethoxy-4-hydroxybenzaldehyde; 2-heptylcyclopentanone; 1-(4-methylphenyl)ethanone; (3E)-4-(2,6,6-trimethyl-1-cyclohexen-1-yl)-3-buten-2-one; (3E)-4-(2,6,6-trimethyl-2-cyclohexen-1-yl)-3-buten-2-one; benzeneethanol; 2H-1-benzopyran-2-one; 4-methoxybenzaldehyde; 10-undecenal; propanoic acid, phenylmethyl ester; beta-methylbenzenepentanol; 1,1-diethoxy-3,7-dimethyl-2,6-octadiene; alpha, alpha-dimethylbenzeneethanol; (2E)-1-(2,6,6-trimethyl-1-cyclohexen-1-yl)-2-buten-1-one; acetic acid, phenylmethyl ester; cyclohexanepropanoic acid, 2-propenyl ester; hexanoic acid, 2-propenyl ester; 1,2-dimethoxy-4-(2-propenyl)benzene; 1,5-dimethyl-bicyclo[3.2.1]octan-8-one oxime; 4-(4-hydroxy-4-methylpentyl)-3-cyclohexene-1-carboxaldehyde; 3-buten-2-ol; 2-[[[2,4(or 3,5)-dimethyl-3-cyclohexen-1-yl]methylene]amino]benzoic acid, methyl ester; 8-cyclohexadecen-1-one; methyl ionone; 2,6-dimethyl-7-octen-2-ol; 2-methoxy-4-(2-propenyl)phenol; (2E)-3,7-dimethyl-2,6-Octadien-1-ol; 2-hydroxy-Benzoic acid, (3Z)-3-hexenyl ester; 2-tridecenenitrile; 4-(2,2-dimethyl-6-methylenecyclohexyl)-3-methyl-3-buten-2-one; tetrahydro-4-methyl-2-(2-methyl-1-propenyl)-2H-pyran; Acetic acid, (2-methylbutoxy)-, 2-propenyl ester; Benzoic acid, 2-hydroxy-3-methylbutyl ester; 2-Buten-1-one, 1-(2,6,6-trimethyl-1-cyclohexen-1-yl)-, (Z)-; Cyclopentanecarboxylic acid, 2-hexyl-3-oxo-, methyl ester; Benzenepropanal, 4-ethyl-.alpha.,.alpha.-dimethyl-; 3-Cyclohexene-1-carboxaldehyde, 3-(4-hydroxy-4-methylpentyl)-; Ethanone, 1-(2,3,4,7,8,8a-hexahydro-3,6,8,8-tetramethyl-1H-3a,7-methanoazulen-5-yl)-, [3R-(3.alpha.,3a.beta.,7.beta.,8a.alpha.)]-; Undecanal, 2-methyl-2H-Pyran-2-one, 6-butyltetrahydro-; Benzenepropanal, 4-(1,1-dimethylethyl)-.alpha.-methyl-; 2(3H)-Furanone, 5-heptyldihydro-; Benzoic acid, 2-[(7-hydroxy-3,7-dimethyloctylidene)amino]-, methyl; Benzoic acid, 2-hydroxy-, phenylmethyl ester; Naphthalene, 2-methoxy-; 2-Cyclopenten-1-one, 2-hexyl-; 2(3H)-Furanone, 5-hexyldihydro-; Oxiranecarboxylic acid, 3-methyl-3-phenyl-, ethyl ester; 2-Oxabicyclo[2.2.2]octane, 1,3,3-trimethyl-; Benzenepentanol, .gamma.-methyl-; 3-Octanol, 3,7-dimethyl-; 3,7-dimethyl-2,6-octadienenitrile; 3,7-dimethyl-6-octen-1-ol; Terpineol acetate; 2-methyl-6-methylene-7-Octen-2-ol, dihydro derivative; 3a,4,5,6,7,7a-hexahydro-4,7-Methano-1H-inden-6-ol propanoate; 3-methyl-2-buten-1-ol acetate; (Z)-3-Hexen-1-ol acetate; 2-ethyl-4-(2,2,3-trimethyl-3-cyclopenten-1-yl)-2-buten-1-ol; 4-(octahydro-4,7-methano-5H-inden-5-ylidene)-butanal; 3-2,4-dimethyl-cyclohexene-1-carboxaldehyde; 1-(1,2,3,4,5,6,7,8-octahydro-2,3,8,8-tetramethyl-2-naphthalenyl)-ethanone; 2-hydroxy-benzoic acid, methyl ester; 2-hydroxybenzoic acid, hexyl ester; 2-phenoxy-ethanol; 2-hydroxybenzoic acid, pentyl ester; 2,3-heptanedione; 2-hexen-1-ol; 6-Octen-2-ol, 2,6-dimethyl-; damascone (alpha, beta, gamma or delta or mixtures thereof), 4,7-Methano-1H-inden-6-ol, 3a,4,5,6,7,7a-hexahydro-, acetate; 9-Undecenal; 8-Undecenal; Isocyclocitral; Ethanone, 1-(1,2,3,5,6,7,8,8a-octahydro-2,3,8,8-tetramethyl-2-naphthalenyl)-; 3-Cyclohexene-1-carboxaldehyde, 3,5-dimethyl-; 3-Cyclohexene-1-carboxaldehyde, 2,4-dimethyl-; 1,6-Octadien-3-ol, 3,7-dimethyl-; 1,6-Octadien-3-ol, 3,7-dimethyl-,acetate; Lilial (p-t-Bucinal), and Cyclopentanone, 2-[2-(4-methyl-3-cyclohexen-1-yl)propyl]- and 1-methyl-4-(1-methylethenyl)cyclohexene and mixtures thereof.

In one aspect the composition may comprise an encapsulated perfume particle comprising either a water-soluble hydroxylic compound or melamine-formaldehyde or modified polyvinyl alcohol. In one aspect the encapsulate comprises (a) an at least partially water-soluble solid matrix comprising one or more water-soluble hydroxylic compounds, preferably starch; and (b) a perfume oil encapsulated by the solid matrix.

In a further aspect the perfume may be pre-complexed with a polyamine, preferably a polyethylenimine so as to form a Schiff base.

Polymers—

The composition may comprise one or more polymers. Examples are carboxymethylcellulose, poly(vinyl-pyrrolidone), poly (ethylene glycol), poly(vinyl alcohol), poly (vinylpyridine-N-oxide), poly(vinylimidazole), polycarboxylates such as polyacrylates, maleic/acrylic acid copolymers and lauryl methacrylate/acrylic acid co-polymers.

The composition may comprise one or more amphiphilic cleaning polymers such as the compound having the following general structure: bis(($C_2H_5O$)($C_2H_4O$)n)($CH_3$)—$N^+$—$C_xH_{2x}$—$N^+$—($CH_3$)-bis(($C_2H_5O$)($C_2H_4O$)n), wherein n=from 20 to 30, and x=from 3 to 8, or sulphated or sulphonated variants thereof.

The composition may comprise amphiphilic alkoxylated grease cleaning polymers which have balanced hydrophilic and hydrophobic properties such that they remove grease particles from fabrics and surfaces. Specific embodiments of the amphiphilic alkoxylated grease cleaning polymers of the present invention comprise a core structure and a plurality of alkoxylate groups attached to that core structure. These may comprise alkoxylated polyalkylenimines, preferably having an inner polyethylene oxide block and an outer polypropylene oxide block.

Alkoxylated polycarboxylates such as those prepared from polyacrylates are useful herein to provide additional grease removal performance. Such materials are described in WO91/08281 and PCT90/01815. Chemically, these materials comprise polyacrylates having one ethoxy side-chain per every 7-8 acrylate units. The side-chains are of the formula —$(CH_2CH_2O)_m$ $(CH_2)_nCH_3$ wherein m is 2-3 and n is 6-12. The side-chains are ester-linked to the polyacrylate "backbone" to provide a "comb" polymer type structure. The molecular weight can vary, but is typically in the range of 2000 to 50,000. Such alkoxylated polycarboxylates can comprise from 0.05 wt % to 10 wt % of the compositions herein.

The isoprenoid-derived surfactants of the present invention, and their mixtures with other cosurfactants and other adjunct ingredients, are particularly suited to be used with an amphilic graft co-polymer, preferably the amphilic graft co-polymer comprises (i) polyethyelene glycol backbone; and (ii) and at least one pendant moiety selected from polyvinyl acetate, polyvinyl alcohol and mixtures thereof. A preferred amphilic graft co-polymer is Sokalan HP22, supplied from BASF. Suitable polymers include random graft copolymers, preferably a polyvinyl acetate grafted polyethylene oxide copolymer having a polyethylene oxide backbone and multiple polyvinyl acetate side chains. The molecular weight of the polyethylene oxide backbone is preferably 6000 and the weight ratio of the polyethylene oxide to polyvinyl acetate is 40 to 60 and no more than 1 grafting point per 50 ethylene oxide units.

Carboxylate Polymer—

The composition of the present invention may also include one or more carboxylate polymers such as a maleate/acrylate random copolymer or polyacrylate homopolymer. In one aspect, the carboxylate polymer is a polyacrylate homopolymer having a molecular weight of from 4,000 to 9,000 Da, or from 6,000 to 9,000 Da.

Soil Release Polymer—

The composition of the present invention may also include one or more soil release polymers having a structure as defined by one of the following structures (I), (II) or (Ill):

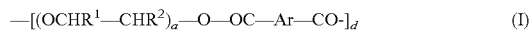  (I)

  (II)

  (III)

wherein:
a, b and c are from 1 to 200;
d, e and f are from 1 to 50;
Ar is a 1,4-substituted phenylene;
sAr is 1,3-substituted phenylene substituted in position 5 with $SO_3Me$;
Me is Li, K, Mg/2, Ca/2, Al/3, ammonium, mono-, di-, tri-, or tetraalkylammonium wherein the alkyl groups are $C_1$-$C_{18}$ alkyl or $C_2$-$C_{10}$ hydroxyalkyl, or mixtures thereof; $R^1$, $R^2$, $R^3$, $R^4$, $R^5$ and $R^6$ are independently selected from H or $C_1$-$C_{18}$ n- or iso-alkyl; and $R^7$ is a linear or branched $C_1$-$C_{18}$ alkyl, or a linear or branched $C_2$-$C_{30}$ alkenyl, or a cycloalkyl group with 5 to 9 carbon atoms, or a $C_8$-$C_{30}$ aryl group, or a $C_6$-$C_{30}$ arylalkyl group.

Suitable soil release polymers are polyester soil release polymers such as Repel-o-tex polymers, including Repel-o-tex, SF-2 and SRP6 supplied by Rhodia. Other suitable soil release polymers include Texcare polymers, including Texcare SRA100, SRA300, SRN100, SRN170, SRN240, SRN300 and SRN325 supplied by Clariant. Other suitable soil release polymers are Marloquest polymers, such as Marloquest SL supplied by Sasol.

Cellulosic Polymer—

The composition of the present invention may also include one or more cellulosic polymers including those selected from alkyl cellulose, alkyl alkoxyalkyl cellulose, carboxyalkyl cellulose, alkyl carboxyalkyl cellulose. In one aspect, the cellulosic polymers are selected from the group comprising carboxymethyl cellulose, methyl cellulose, methyl hydroxyethyl cellulose, methyl carboxymethyl cellulose, and mixtures thereof. In one aspect, the carboxymethyl cellulose has a degree of carboxymethyl substitution from 0.5 to 0.9 and a molecular weight from 100,000 to 300,000 Da.

Enzymes—

The composition may comprise one or more additional enzymes which provide cleaning performance and/or fabric care benefits. Examples of suitable enzymes include, but are not limited to, hemicellulases, peroxidases, proteases, cellulases, xylanases, lipases, phospholipases, esterases, cutinases, pectinases, mannanases, pectate lyases, keratinases, reductases, oxidases, phenoloxidases, lipoxygenases, xanthanase, ligninases, pullulanases, tannases, pentosanases, malanases, β-glucanases, arabinosidases, hyaluronidase, chondroitinase, laccase, chlorophyllases and amylases, or mixtures thereof. A typical combination is an enzyme cocktail that may comprise e.g. a protease and lipase in conjunction with amylase. When present in a composition, the aforementioned additional enzymes may be present at levels from 0.00001 to 2 wt %, from 0.0001 to 1 wt % or from 0.001 to 0.5 wt % enzyme protein by weight of the composition.

In general the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases—

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO89/09259. Especially suitable cellulases are the alkaline or neutral cellulases having colour care benefits. Examples of such cellulases are cellulases described in EP0495257, EP0531372, WO96/11262, WO96/29397, and WO98/08940. Other examples are cellulase variants such as those described in WO94/07998, EP0531315, U.S. Pat. Nos. 5,457,046, 5,686,593, 5,763, 254, WO95/24471, WO98/12307 and WO99/001544.

Other cellulases are endo-beta-1,4-glucanase enzyme having a sequence of at least 97% identity to the amino acid sequence of position 1 to position 773 of SEQ ID NO:2 of WO02/099091 or a family 44 xyloglucanase, which a xyloglucanase enzyme having a sequence of at least 60% identity to positions 40-559 of SEQ ID NO: 2 of WO01/062903.

Commercially available cellulases include Celluzyme™, and Carezyme™ (Novozymes A/S) Carezyme Premium™

(Novozymes A/S), Celluclean™ (Novozymes A/S), Celluclean Classic™ (Novozymes A/S), Cellusoft™ (Novozymes A/S), Whitezyme™ (Novozymes A/S), Clazinase™ and Puradax HA™ (Genencor International Inc.), and KAC-500(B)™ (Kao Corporation).

Proteases—

Suitable proteases include those of bacterial, fungal, plant, viral or animal origin e.g. vegetable or microbial origin. Microbial origin is preferred. Chemically modified or protein engineered mutants are included. It may be an alkaline protease, such as a serine protease or a metalloprotease. A serine protease may for example be of the S1 family, such as trypsin, or the S8 family such as subtilisin. A metalloproteases protease may for example be a thermolysin from e.g. family M4 or other metalloprotease such as those from M5, M7 or M8 families.

The term "subtilases" refers to a sub-group of serine protease according to Siezen et al., Protein Engng. 4 (1991) 719-737 and Siezen et al. Protein Science 6 (1997) 501-523. Serine proteases are a subgroup of proteases characterized by having a serine in the active site, which forms a covalent adduct with the substrate. The subtilases may be divided into 6 sub-divisions, i.e. the Subtilisin family, the Thermitase family, the Proteinase K family, the Lantibiotic peptidase family, the Kexin family and the Pyrolysin family.

Examples of subtilases are those derived from *Bacillus* such as *Bacillus lentus, B. alkalophilus, B. subtilis, B. amyloliquefaciens, Bacillus pumilus* and *Bacillus gibsonii* described in; U.S. Pat. No. 7,262,042 and WO009/021867, and subtilisin *lentus*, subtilisin Novo, subtilisin Carlsberg, *Bacillus licheniformis*, subtilisin BPN', subtilisin 309, subtilisin 147 and subtilisin 168 described in WO89/06279 and protease PD138 described in (WO93/18140). Other useful proteases may be those described in WO92/175177, WO01/016285, WO02/026024 and WO02/016547. Examples of trypsin-like proteases are trypsin (e.g. of porcine or bovine origin) and the *Fusarium* protease described in WO89/06270, WO94/25583 and WO05/040372, and the chymotrypsin proteases derived from Cellumonas described in WO05/052161 and WO05/052146.

A further preferred protease is the alkaline protease from *Bacillus lentus* DSM 5483, as described for example in WO95/23221, and variants thereof which are described in WO92/21760, WO95/23221, EP1921147 and EP1921148.

Examples of metalloproteases are the neutral metalloprotease as described in WO07/044993 (Genencor Int.) such as those derived from *Bacillus amyloliquefaciens*.

Examples of useful proteases are the variants described in: WO92/19729, WO96/034946, WO98/20115, WO98/20116, WO99/011768, WO01/44452, WO03/006602, WO04/03186, WO04/041979, WO07/006305, WO11/036263, WO11/036264, especially the variants with substitutions in one or more of the following positions: 3, 4, 9, 15, 27, 36, 57, 68, 76, 87, 95, 96, 97, 98, 99, 100, 101, 102, 103, 104, 106, 118, 120, 123, 128, 129, 130, 160, 167, 170, 194, 195, 199, 205, 206, 217, 218, 222, 224, 232, 235, 236, 245, 248, 252 and 274 using the BPN' numbering. More preferred the subtilase variants may comprise the mutations: S3T, V41, S9R, A15T, K27R, *36D, V68A, N76D, N87S,R, *97E, A98S, S99G,D,A, S99AD, S101G,M,R S103A, V1041,Y,N, S106A, G118V,R, H120D,N, N123S, S128L, P129Q, S130A, G160D, Y167A, R170S, A194P, G195E, V199M, V2051, L217D, N218D, M222S, A232V, K235L, Q236H, Q245R, N252K, T274A (using BPN' numbering).

Suitable commercially available protease enzymes include those sold under the trade names Alcalase®, Duralase™, Durazym™, Relase®, Relase® Ultra, Savinase®, Savinase® Ultra, Primase®, Polarzyme®, Kannase®, Liquanase®, Liquanase® Ultra, Ovozyme®, Coronase®, Coronase® Ultra, Neutrase®, Everlase® and Esperase® (Novozymes A/S), those sold under the tradename Maxatase®, Maxacal®, Maxapem®, Purafect®, Purafect Prime®, Preferenz™, Purafect MA®, Purafect Ox®, Purafect OxP®, Puramax®, Properase®, Effectenz™ FN2®, FN3®, FN4®, Excellase®, , Opticlean® and Optimase® (Danisco/DuPont), Axapem™ (Gist-Brocases N.V.), BLAP (sequence shown in FIG. 29 of U.S. Pat. No. 5,352,604) and variants hereof (Henkel AG) and KAP (*Bacillus alkalophilus* subtilisin) from Kao.

Lipases and Cutinases—Suitable lipases and cutinases include those of bacterial orfungal origin. Chemically modified or protein engineered mutant enzymes are included. Examples include lipase from *Thermomyces*, e.g. from *T. lanuginosus* (previously named *Humicola lanuginosa*) as described in EP258068 and EP305216, cutinase from *Humicola*, e.g. *H. insolens* (WO96/13580), lipase from strains of *Pseudomonas* (some of these now renamed to *Burkholderia*), e.g. *P. alcaligenes* or *P. pseudoalcaligenes* (EP218272), *P. cepacia* (EP331376), *P.* sp. strain SD705 (WO95/06720 & WO96/27002), *P. wisconsinensis* (WO96/12012), GDSL-type *Streptomyces* lipases (WO10/065455), cutinase from *Magnaporthe grisea* (WO10/107560), cutinase from *Pseudomonas mendocina* (U.S. Pat. No. 5,389,536), lipase from *Thermobifida fusca* (WO11/084412), *Geobacillus stearothermophilus* lipase (WO11/084417), lipase from *Bacillus subtilis* (WO11/084599), and lipase from *Streptomyces griseus* (WO11/150157) and *S. pristinaespiralis* (WO12/137147).

Other examples are lipase variants such as those described in EP407225, WO92/05249, WO94/01541, WO94/25578, WO95/14783, WO95/30744, WO95/35381, WO95/22615, WO96/00292, WO97/04079, WO97/07202, WO00/34450, WO00/60063, WO01/92502, WO07/87508 and WO09/109500.

Preferred commercial lipase products include Lipolase™, Lipex™; Lipex Evity™; Lipolex™ and Lipoclean™ (Novozymes A/S), Lumafast (originally from Genencor) and Lipomax (originally from Gist-Brocades).

Still other examples are lipases sometimes referred to as acyltransferases or perhydrolases, e.g. acyltransferases with homology to *Candida antarctica* lipase A (WO10/111143), acyltransferase from *Mycobacterium smegmatis* (WO05/56782), perhydrolases from the CE 7 family (WO09/67279), and variants of the *M. smegmatis* perhydrolase in particular the S54V variant used in the commercial product Gentle Power Bleach from Huntsman Textile Effects Pte Ltd (WO10/100028).

Amylases—

Suitable amylases which can be used together with the enzyme/variant/blend of enzymes of the invention may be an alpha-amylase or a glucoamylase and may be of bacterial or fungal origin. Chemically modified or protein engineered mutants are included. Amylases include, for example, alpha-amylases obtained from *Bacillus*, e.g., a special strain of *Bacillus licheniformis*, described in more detail in GB1296839.

Suitable amylases include amylases having SEQ ID NO: 2 in WO95/10603 or variants having 90% sequence identity to SEQ ID NO: 3 thereof. Preferred variants are described in WO94/02597, WO94/18314, WO97/43424 and SEQ ID NO: 4 of WO99/019467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444.

Different suitable amylases include amylases having SEQ ID NO: 6 in WO02/010355 or variants thereof having 90% sequence identity to SEQ ID NO: 6. Preferred variants of SEQ ID NO: 6 are those having a deletion in positions 181 and 182 and a substitution in position 193. Other amylases which are suitable are hybrid alpha-amylase comprising residues 1-33 of the alpha-amylase derived from *B. amyloliquefaciens* shown in SEQ ID NO: 6 of WO06/066594 and residues 36-483 of the *B. licheniformis* alpha-amylase shown in SEQ ID NO: 4 of WO06/066594 or variants having 90% sequence identity thereof. Preferred variants of this hybrid alpha-amylase are those having a substitution, a deletion or an insertion in one of more of the following positions: G48, T49, G107, H156, A181, N190, M197, I201, A209 and Q264. Most preferred variants of the hybrid alpha-amylase comprising residues 1-33 of the alpha-amylase derived from *B. amyloliquefaciens* shown in SEQ ID NO: 6 of WO06/066594 and residues 36-483 of SEQ ID NO: 4 are those having the substitutions:
M197T;
H156Y+A181T+N190F+A209V+Q264S; or
G48A+T491+G107A+H156Y+A181T+N190F+I201F+A209V+Q264S.

Further amylases which are suitable are amylases having SEQ ID NO: 6 in WO99/019467 or variants thereof having 90% sequence identity to SEQ ID NO: 6. Preferred variants of SEQ ID NO: 6 are those having a substitution, a deletion or an insertion in one or more of the following positions: R181, G182, H183, G184, N195, I206, E212, E216 and K269. Particularly preferred amylases are those having deletion in positions R181 and G182, or positions H183 and G184.

Additional amylases which can be used are those having SEQ ID NO: 1, SEQ ID NO: 3, SEQ ID NO: 2 or SEQ ID NO: 7 of WO96/023873 or variants thereof having 90% sequence identity to SEQ ID NO: 1, SEQ ID NO: 2, SEQ ID NO: 3 or SEQ ID NO: 7. Preferred variants of SEQ ID NO: 1, SEQ ID NO: 2, SEQ ID NO: 3 or SEQ ID NO: 7 are those having a substitution, a deletion or an insertion in one or more of the following positions: 140, 181, 182, 183, 184, 195, 206, 212, 243, 260, 269, 304 and 476, using SEQ ID 2 of WO96/023873 for numbering. More preferred variants are those having a deletion in two positions selected from 181, 182, 183 and 184, such as 181 and 182, 182 and 183, or positions 183 and 184. Most preferred amylase variants of SEQ ID NO: 1, SEQ ID NO: 2 or SEQ ID NO: 7 are those having a deletion in positions 183 and 184 and a substitution in one or more of positions 140, 195, 206, 243, 260, 304 and 476.

Other amylases which can be used are amylases having SEQ ID NO: 2 of WO08/153815, SEQ ID NO: 10 in WO 01/66712 or variants thereof having 90% sequence identity to SEQ ID NO: 2 of WO08/153815 or 90% sequence identity to SEQ ID NO: 10 in WO01/66712. Preferred variants of SEQ ID NO: 10 in WO01/66712 are those having a substitution, a deletion or an insertion in one of more of the following positions: 176, 177, 178, 179, 190, 201, 207, 211 and 264.

Further suitable amylases are amylases having SEQ ID NO: 2 of WO09/061380 or variants having 90% sequence identity to SEQ ID NO: 2 thereof. Preferred variants of SEQ ID NO: 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred variants of SEQ ID NO: 2 are those having the substitution in one of more of the following positions: Q87E,R, Q98R, S125A, N128C, T1311, T1651, K178L, T182G, M201L, F202Y, N225E,R, N272E,R, S243Q,A,E,D, Y305R, R309A, Q320R, Q359E, K444E and G475K and/or deletion in position R180 and/or S181 or of T182 and/or G183. Most preferred amylase variants of SEQ ID NO: 2 are those having the substitutions:
N128C+K178L+T182G+Y305R+G475K;
N128C+K178L+T182G+F202Y+Y305R+D319T+G475K;
S125A+N128C+K178L+T182G+Y305R+G475K; or
S125A+N128C+T1311+T1651+K178L+T182G+Y305R+G475K wherein the variants are C-terminally truncated and optionally further comprises a substitution at position 243 and/or a deletion at position 180 and/or position 181.

Other suitable amylases are the alpha-amylase having SEQ ID NO: 12 in WO01/66712 or a variant having at least 90% sequence identity to SEQ ID NO: 12. Preferred amylase variants are those having a substitution, a deletion or an insertion in one of more of the following positions of SEQ ID NO: 12 in WO01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Particular preferred amylases include variants having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions.

Other examples are amylase variants such as those described in WO2011/098531, WO2013/001078 and WO2013/001087.

Commercially available amylases are Duramyl™, Termamyl™, Fungamyl™, Stainzyme™, Stainzyme Plus™, Natalase™, Liquozyme X and BAN™ (from Novozymes A/S), and Rapidase™, Purastar™/Effectenz™, Powerase and Preferenz S100 (from Genencor International Inc./DuPont).

Peroxidases/Oxidases—

Suitable peroxidases according to the invention is a peroxidase enzyme comprised by the enzyme classification EC 1.11.1.7, as set out by the Nomenclature Committee of the International Union of *Biochemistry* and Molecular Biology (IUBMB), or any fragment derived therefrom, exhibiting peroxidase activity.

Suitable peroxidases include those of plant, bacterial or fungal origin. Chemically modified or protein engineered mutants are included. Examples of useful peroxidases include peroxidases from *Coprinopsis*, e.g., from *C. cinerea* (EP179486), and variants thereof as those described in WO93/24618, WO95/10602, and WO98/15257.

A peroxidase also includes a haloperoxidase enzyme, such as chloroperoxidase, bromoperoxidase and compounds exhibiting chloroperoxidase or bromoperoxidase activity. Haloperoxidases are classified according to their specificity for halide ions. Chloroperoxidases (E.C. 1.11.1.10) catalyze formation of hypochlorite from chloride ions.

In an embodiment, the haloperoxidase of the invention is a chloroperoxidase. Preferably, the haloperoxidase is a vanadium haloperoxidase, i.e., a vanadate-containing haloperoxidase. In a preferred method of the present invention the vanadate-containing haloperoxidase is combined with a source of chloride ion.

Haloperoxidases have been isolated from many different fungi, in particular from the fungus group dematiaceous hyphomycetes, such as Caldariomyces, e.g., *C. fumago, Alternaria, Curvularia*, e.g., *C. verruculosa* and *C. inaequalis, Drechslera, Ulocladium* and *Botrytis*.

Haloperoxidases have also been isolated from bacteria such as *Pseudomonas*, e.g., *P. pyrrocinia* and *Streptomyces*, e.g., *S. aureofaciens*.

In an preferred embodiment, the haloperoxidase is derivable from *Curvularia* sp., in particular *Curvularia verruculosa* or *Curvularia inaequalis*, such as *C. inaequalis* CBS 102.42 as described in WO95/27046; or *C. verruculosa* CBS 147.63 or *C. verruculosa* CBS 444.70 as described in WO97/04102; or from *Drechslera hartlebii* as described in WO01/79459, *Dendryphiella salina* as described in WO01/79458, *Phaeotrichoconis crotalarie* as described in WO01/79461, or *Geniculosporium* sp. as described in WO01/79460.

An oxidase according to the invention include, in particular, any laccase enzyme comprised by the enzyme classification EC 1.10.3.2, or any fragment derived therefrom exhibiting laccase activity, or a compound exhibiting a similar activity, such as a catechol oxidase (EC 1.10.3.1), an o-aminophenol oxidase (EC 1.10.3.4), or a bilirubin oxidase (EC 1.3.3.5).

Preferred laccase enzymes are enzymes of microbial origin. The enzymes may be derived from plants, bacteria or fungi (including filamentous fungi and yeasts).

Suitable examples from fungi include a laccase derivable from a strain of *Aspergillus, Neurospora*, e.g., *N. crassa, Podospora, Botrytis, Collybia, Fomes, Lentinus, Pleurotus, Trametes*, e.g., *T. villosa* and *T. versicolor, Rhizoctonia*, e.g., *R. solani, Coprinopsis*, e.g., *C. cinerea, C. comatus, C. friesii*, and *C. plicatilis, Psathyrella*, e.g., *P. condelleana, Panaeolus*, e.g., *P. papilionaceus, Myceliophthora*, e.g., *M. thermophila, Schytalidium*, e.g., *S. thermophilum, Polyporus*, e.g., *P. pinsitus, Phlebia*, e.g., *P. radiata* (WO92/01046), or *Coriolus*, e.g., *C. hirsutus* (JP2238885).

Suitable examples from bacteria include a laccase derivable from a strain of *Bacillus*.

A laccase derived from *Coprinopsis* or *Myceliophthora* is preferred; in particular a laccase derived from *Coprinopsis cinerea*, as disclosed in WO97/08325; or from *Myceliophthora thermophila*, as disclosed in WO95/33836.

Other preferred enzymes include pectate lyases sold under the tradenames Pectawash®, Pectaway®, Xpect® and mannanases sold under the tradenames Mannaway® (Novozymes), and Purabrite® (Danisco/Dupont).

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, for example, as a granulate, liquid, slurry, etc. Preferred detergent additive formulations are granulates, in particular non-dusting granulates, liquids, in particular stabilized liquids, or slurries.

Non-dusting granulates may be produced, e.g. as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP238216.

Dye Transfer Inhibiting Agents—

The compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a composition, the dye transfer inhibiting agents may be present at levels from 0.0001 to 10 wt %, from 0.01 to 5 wt % or from 0.1 to 3 wt %.

Brighteners—

The compositions of the present invention can also contain additional components that may tint articles being cleaned, such as fluorescent brighteners.

The composition may comprise C.I. fluorescent brightener 260 in alpha-crystalline form having the following structure:

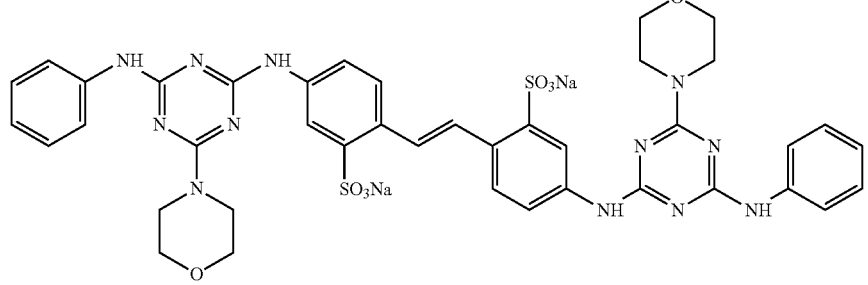

In one aspect, the brightener is a cold water soluble brightener, such as the C.I. fluorescent brightener 260 in alpha-crystalline form. In one aspect the brightener is predominantly in alpha-crystalline form, which means that typically at least 50 wt %, at least 75 wt %, at least 90 wt %, at least 99 wt %, or even substantially all, of the C.I. fluorescent brightener 260 is in alpha-crystalline form.

The brightener is typically in micronized particulate form, having a weight average primary particle size of from 3 to 30 micrometers, from 3 micrometers to 20 micrometers, or from 3 to 10 micrometers.

The composition may comprise C.I. fluorescent brightener 260 in beta-crystalline form, and the weight ratio of: (i) C.I. fluorescent brightener 260 in alpha-crystalline form, to (ii) C.I. fluorescent brightener 260 in beta-crystalline form may be at least 0.1, or at least 0.6. BE680847 relates to a process for making C.I fluorescent brightener 260 in alpha-crystalline form.

Commercial optical brighteners which may be useful in the present invention can be classified into subgroups, which include, but are not necessarily limited to, derivatives of stilbene, pyrazoline, coumarin, carboxylic acid, methinecyanines, dibenzothiophene-5,5-dioxide, azoles, 5- and 6-membered-ring heterocycles, and other miscellaneous agents. Examples of such brighteners are disclosed in "The Production and Application of Fluorescent Brightening Agents", M. Zahradnik, Published by John Wiley & Sons, New York (1982). Specific nonlimiting examples of optical brighteners which are useful in the present compositions are those identified in U.S. Pat. Nos. 4,790,856 and 3,646,015.

A further suitable brightener has the structure below:

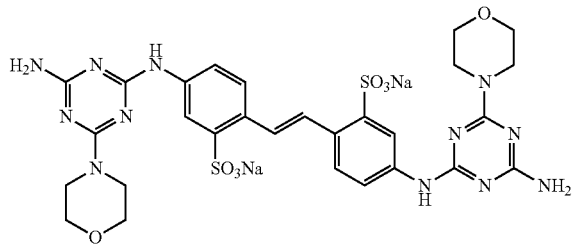

Suitable fluorescent brightener levels include lower levels of from 0.01 wt %, from 0.05 wt %, from 0.1 wt % or from 0.2 wt % to upper levels of 0.5 wt % or 0.75 wt %.

In one aspect the brightener may be loaded onto a clay to form a particle. Silicate salts—The compositions of the present invention can also contain silicate salts, such as sodium or potassium silicate. The composition may comprise of from 0 wt % to less than 10 wt % silicate salt, to 9 wt %, or to 8 wt %, or to 7 wt %, or to 6 wt %, or to 5 wt %, or to 4 wt %, or to 3 wt %, or even to 2 wt %, and from above 0 wt %, or from 0.5 wt %, or from 1 wt % silicate salt. A suitable silicate salt is sodium silicate.

Dispersants—

The compositions of the present invention can also contain dispersants. Suitable water-soluble organic materials include the homo- or co-polymeric acids or their salts, in which the polycarboxylic acid comprises at least two carboxyl radicals separated from each other by not more than two carbon atoms.

Enzyme Stabilizers—

Enzymes for use in compositions can be stabilized by various techniques. The enzymes employed herein can be stabilized by the presence of water-soluble sources of calcium and/or magnesium ions. Examples of conventional stabilizing agents are, e.g. a polyol such as propylene glycol or glycerol, a sugar or sugar alcohol, lactic acid, boric acid, or a boric acid derivative, e.g. an aromatic borate ester, or a phenyl boronic acid derivative such as 4-formylphenyl boronic acid, and the composition may be formulated as described in, for example, WO92/19709 and WO92/19708

In case of aqueous compositions comprising protease, a reversible protease inhibitor, such as a boron compound including borate, 4-formyl phenylboronic acid, phenylboronic acid and derivatives thereof, or compounds such as calcium formate, sodium formate and 1,2-propane diol can be added to further improve stability.

Solvents—

Suitable solvents include water and other solvents such as lipophilic fluids. Examples of suitable lipophilic fluids include siloxanes, other silicones, hydrocarbons, glycol ethers, glycerine derivatives such as glycerine ethers, perfluorinated amines, perfluorinated and hydrofluoroether solvents, low-volatility nonfluorinated organic solvents, diol solvents, other environmentally-friendly solvents and mixtures thereof.

Structurant/Thickeners—

Structured liquids can either be internally structured, whereby the structure is formed by primary ingredients (e.g. surfactant material) and/or externally structured by providing a three dimensional matrix structure using secondary ingredients (e.g. polymers, clay and/or silicate material). The composition may comprise a structurant, from 0.01 to 5 wt %, or from 0.1 to 2.0 wt %. The structurant is typically selected from the group consisting of diglycerides and triglycerides, ethylene glycol distearate, microcrystalline cellulose, cellulose-based materials, microfiber cellulose, hydrophobically modified alkali-swellable emulsions such as Polygel W30 (3VSigma), biopolymers, xanthan gum, gellan gum, and mixtures thereof. A suitable structurant includes hydrogenated castor oil, and non-ethoxylated derivatives thereof. A suitable structurant is disclosed in U.S. Pat. No. 6,855,680. Such structurants have a thread-like structuring system having a range of aspect ratios. Other suitable structurants and the processes for making them are described in WO10/034736.

Conditioning Agents—

The composition of the present invention may include a high melting point fatty compound. The high melting point fatty compound useful herein has a melting point of 25° C. or higher, and is selected from the group consisting of fatty alcohols, fatty acids, fatty alcohol derivatives, fatty acid derivatives, and mixtures thereof. Such compounds of low melting point are not intended to be included in this section. Non-limiting examples of the high melting point compounds are found in International Cosmetic Ingredient Dictionary, Fifth Edition, 1993, and CTFA Cosmetic Ingredient Handbook, Second Edition, 1992.

The high melting point fatty compound is included in the composition at a level of from 0.1 to 40 wt %, from 1 to 30 wt %, from 1.5 to 16 wt %, from 1.5 to 8 wt % in view of providing improved conditioning benefits such as slippery feel during the application to wet hair, softness and moisturized feel on dry hair.

The compositions of the present invention may contain a cationic polymer. Concentrations of the cationic polymer in the composition typically range from 0.05 to 3 wt %, from 0.075 to 2.0 wt %, or from 0.1 to 1.0 wt %. Suitable cationic polymers will have cationic charge densities of at least 0.5 meq/gm, at least 0.9 meq/gm, at least 1.2 meq/gm, at least 1.5 meq/gm, or less than 7 meq/gm, and less than 5 meq/gm, at the pH of intended use of the composition, which pH will generally range from pH3 to pH9, or between pH4 and pH8. Herein, "cationic charge density" of a polymer refers to the ratio of the number of positive charges on the polymer to the molecular weight of the polymer. The average molecular weight of such suitable cationic polymers will generally be between 10,000 and 10 million, between 50,000 and 5 million, or between 100,000 and 3 million.

Suitable cationic polymers for use in the compositions of the present invention contain cationic nitrogen-containing moieties such as quaternary ammonium or cationic protonated amino moieties. Any anionic counterions can be used in association with the cationic polymers so long as the polymers remain soluble in water, in the composition, or in a coacervate phase of the composition, and so long as the counterions are physically and chemically compatible with the essential components of the composition or do not otherwise unduly impair composition performance, stability or aesthetics. Nonlimiting examples of such counterions include halides (e.g., chloride, fluoride, bromide, iodide), sulfate and methylsulfate.

Nonlimiting examples of such polymers are described in the CTFA Cosmetic Ingredient Dictionary, 3rd edition, edited by Estrin, Crosley, and Haynes, (The Cosmetic, Toiletry, and Fragrance Association, Inc., Washington, D.C. (1982)).

Other suitable cationic polymers for use in the composition include polysaccharide polymers, cationic guar gum derivatives, quaternary nitrogen-containing cellulose ethers, synthetic polymers, copolymers of etherified cellulose, guar and starch. When used, the cationic polymers herein are either soluble in the composition or are soluble in a complex coacervate phase in the composition formed by the cationic polymer and the anionic, amphoteric and/or zwitterionic surfactant component described hereinbefore. Complex coacervates of the cationic polymer can also be formed with other charged materials in the composition. Suitable cationic polymers are described in U.S. Pat. Nos. 3,962,418; 3,958,581; and US2007/0207109.

The composition of the present invention may include a nonionic polymer as a conditioning agent. Polyalkylene glycols having a molecular weight of more than 1000 are useful herein.

Useful are those having the following general formula:

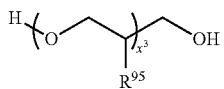

wherein $R^{95}$ is selected from the group consisting of H, methyl, and mixtures thereof. Conditioning agents, and in particular silicones, may be included in the composition. The conditioning agents useful in the compositions of the present invention typically comprise a water insoluble, water dispersible, non-volatile, liquid that forms emulsified, liquid particles. Suitable conditioning agents for use in the composition are those conditioning agents characterized generally as silicones (e.g., silicone oils, cationic silicones, silicone gums, high refractive silicones, and silicone resins), organic conditioning oils (e.g., hydrocarbon oils, polyolefins, and fatty esters) or combinations thereof, or those conditioning agents which otherwise form liquid, dispersed particles in the aqueous surfactant matrix herein. Such conditioning agents should be physically and chemically compatible with the essential components of the composition, and should not otherwise unduly impair composition stability, aesthetics or performance.

The concentration of the conditioning agent in the composition should be sufficient to provide the desired conditioning benefits. Such concentration can vary with the conditioning agent, the conditioning performance desired, the average size of the conditioning agent particles, the type and concentration of other components, and other like factors.

The concentration of the silicone conditioning agent typically ranges from 0.01 to 10 wt %. Non-limiting examples of suitable silicone conditioning agents, and optional suspending agents for the silicone, are described in U.S. Reissue Pat. No. 34,584; U.S. Pat. Nos. 5,104,646; 5,106,609; 4,152,416; 2,826,551; 3,964,500; 4,364,837; 6,607,717; 6,482,969; 5,807,956; 5,981,681; 6,207,782; 7,465,439; 7,041,767; 7,217,777; US2007/0286837A1; US2005/0048549A1; US2007/0041929A1; GB849433; DE10036533, which are all incorporated herein by reference; Chemistry and Technology of Silicones, New York: Academic Press (1968); General Electric Silicone Rubber Product Data Sheets SE 30, SE 33, SE 54 and SE 76; Silicon Compounds, Petrarch Systems, Inc. (1984); and in Encyclopedia of Polymer Science and Engineering, vol. 15, 2d ed., pp 204-308, John Wiley & Sons, Inc. (1989).

The compositions of the present invention may also comprise from 0.05 to 3 wt % of a at least one organic conditioning oil as the conditioning agent, either alone or in combination with other conditioning agents, such as the silicones (described herein). Suitable conditioning oils include hydrocarbon oils, polyolefins, and fatty esters. Also suitable for use in the compositions herein are the conditioning agents described in U.S. Pat. Nos. 5,674,478 and 5,750,122 or in U.S. Pat. Nos. 4,529,586; 4,507,280; 4,663,158; 4,197,865; 4,217,914; 4,381,919; and 4,422,853.

Hygiene and Malodour—

The compositions of the present invention may also comprise one or more of zinc ricinoleate, thymol, quaternary ammonium salts such as Bardac®, polyethylenimines (such as Lupasol® from BASF) and zinc complexes thereof, silver and silver compounds, especially those designed to slowly release $Ag^+$ or nano-silver dispersions.

Probiotics—

The compositions may comprise probiotics such as those described in WO009/043709.

Suds Boosters—

If high sudsing is desired, suds boosters such as the $C_{10}$-$C_{16}$ alkanolamides or $C_{10}$-$C_{14}$ alkyl sulphates can be incorporated into the compositions, typically at 1 to 10 wt % levels. The $C_{10}$-$C_{14}$ monoethanol and diethanol amides illustrate a typical class of such suds boosters. Use of such suds boosters with high sudsing adjunct surfactants such as the amine oxides, betaines and sultaines noted above is also advantageous. If desired, water-soluble magnesium and/or calcium salts such as $MgCl_2$, $MgSO_4$, $CaCl_2$, $CaSO_4$ and the like, can be added at levels of, typically, 0.1 to 2 wt %, to provide additional suds and to enhance grease removal performance.

Suds Suppressors—

Compounds for reducing or suppressing the formation of suds can be incorporated into the compositions of the present invention. Suds suppression can be of particular importance in the so-called "high concentration cleaning process" as described in U.S. Pat. Nos. 4,489,455 and 4,489,574, and in front-loading-style washing machines. A wide variety of materials may be used as suds suppressors, and suds suppressors are well known to those skilled in the art. See e.g. Kirk Othmer Encyclopedia of Chemical Technology, Third Edition, Volume 7, p. 430-447 (John Wiley & Sons, Inc., 1979). Examples of suds supressors include monocarboxylic fatty acid and soluble salts therein, high molecular weight hydrocarbons such as paraffin, fatty acid esters (e.g., fatty acid triglycerides), fatty acid esters of monovalent alcohols, aliphatic $C_{18}$-$C_{40}$ ketones (e.g., stearone), N-alkylated amino triazines, waxy hydrocarbons preferably having a melting point below about 100° C., silicone suds suppressors, and secondary alcohols. Suds supressors are described in U.S. Pat. Nos. 2,954,347; 4,265,779; 4,265,779; 3,455,839; 3,933,672; 4,652,392; 4,978,471; 4,983,316; 5,288,431; 4,639,489; 4,749,740; 4,798,679; 4,075,118; EP89307851.9; EP150872; and DOS 2,124,526.

For any detergent compositions to be used in automatic laundry washing machines, suds should not form to the extent that they overflow the washing machine. Suds suppressors, when utilized, are preferably present in a "suds suppressing amount. By "suds suppressing amount" is meant that the formulator of the composition can select an amount of this suds controlling agent that will sufficiently control the suds to result in a low-sudsing laundry detergent for use in automatic laundry washing machines.

The compositions herein will generally comprise from 0 to 10 wt % of suds suppressor. When utilized as suds suppressors, monocarboxylic fatty acids, and salts therein, will be present typically in amounts up to 5 wt %. Preferably, from 0.5 to 3 wt % of fatty monocarboxylate suds suppressor is utilized. Silicone suds suppressors are typically utilized in amounts up to 2.0 wt %, although higher amounts may be used. Monostearyl phosphate suds suppressors are generally utilized in amounts ranging from 0.1 to 2 wt %. Hydrocarbon suds suppressors are typically utilized in amounts ranging from 0.01 to 5.0 wt %, although higher levels can be used. The alcohol suds suppressors are typically used at 0.2 to 3 wt %.

The compositions herein may have a cleaning activity over a broad range of pH. In certain embodiments the compositions have cleaning activity from pH4 to pH 11.5. In other embodiments, the compositions are active from pH6 to pH11, from pH7 to pH 11, from pH8 to pH11, from pH9 to pH11, or from pH10 to pH11.5.

The compositions herein may have cleaning activity over a wide range of temperatures, e.g., from 10° C. or lower to 90° C. Preferably the temperature will be below 50° C. or 40° C. or even 30° C. In certain embodiments, the optimum temperature range for the compositions is from 10° C. to 20° C., from 15° C. to 25° C., from 15° C. to 30° C., from 20° C. to 30° C., from 25° C. to 35° C., from 30° C. to 40° C., from 35° C. to 45° C., or from 40° C. to 50° C.

Form of the Composition

The detergent compositions described herein are advantageously employed for example, in laundry applications for private households as well as in industrial and institutional cleaning. The compositions of the invention are in particular solid or liquid cleaning and/or treatment compositions. In one aspect the invention relates to a composition, wherein the form of the composition is selected from the group consisting of a regular, compact or concentrated liquid; a gel; a paste; a soap bar; a regular or a compacted powder; a granulated solid; a homogenous or a multilayer tablet with two or more layers (same or different phases); a pouch having one or more compartments; a single or a multi-compartment unit dose form; or any combination thereof.

The form of the composition may separate the components physically from each other in compartments such as e.g. water dissolvable pouches or in different layers of tablets. Thereby negative storage interaction between components can be avoided. Different dissolution profiles of each of the compartments can also give rise to delayed dissolution of selected components in the wash solution.

Pouches can be configured as single or multicompartments. It can be of any form, shape and material which is suitable for hold the composition, e.g. without allowing the release of the composition to release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivates thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxypropyl methyl cellulose (HPMC). Preferably the level of polymer in the film for example PVA is at least about 60%. Preferred average molecular weight will typically be about 20,000 to about 150,000. Films can also be of blended compositions comprising hydrolytically degradable and water soluble polymer blends such as polylactide and polyvinyl alcohol (known under the Trade reference M8630 as sold by Mono-Sol LLC, Indiana, USA) plus plasticisers like glycerol, ethylene glycerol, propylene glycol, sorbitol and mixtures thereof. The pouches can comprise a solid laundry cleaning composition or part components and/or a liquid cleaning composition or part components separated by the water soluble film. The compartment for liquid components can be different in composition than compartments containing solids (US2009/0011970 A1).

Lipase Particles

The lipase variants comprised in the water-soluble film of the invention may be present as lipase particles. The lipase particles may even contain one or more Additional Enzymes, as described below.

Lipase particles are any form of lipase variant in a solid particulate form. That can be as lipase crystals, lipase precipitate, spray or freeze-dried lipase or any form of granulated lipase, either as a powder or a suspension in liquid. Typically the particle size, measured as equivalent spherical diameter (volume based average particle size), of the lipase particles is below 2 mm, preferably below 1 mm, below 0.5 mm, below 0.25 mm, or below 0.1 mm; and above 0.05 μm, preferably above 0.1 μm, above 0.5 μm, above 1 μm, above 5 μm or above 10 μm.

In a preferred embodiment, the particle size of the lipase particles is from 0.5 μm to 100 μm.

The lipase particles contain at least 1% w/w lipase protein, preferably at least 5% w/w lipase protein, at least 10% w/w lipase protein, at least 20% w/w lipase protein, at least 30% w/w lipase protein, at least 40% w/w lipase protein, at least 50% w/w lipase protein, at least 60% w/w lipase protein, at least 70% w/w lipase protein, at least 80% w/w lipase protein, or at least 90% w/w lipase protein.

In a preferred embodiment, the lipase particles are lipase crystals, or the lipase protein is on a crystalline form.

Enzyme crystallization may be carried out in a number of ways, as known in the art (e.g., as described in WO91/09943 or WO94/22903).

The lipase may be formulated in the lipase particle as known in the art for solid enzyme formulations, such as formulations for reducing dust, improving stability and/or modifying release rate of the enzyme. The lipase particle may also be formulated in a matrix or coated with agents suppressing dissolution of the enzyme particle in the PVOH/film solution used for preparing the water-soluble film.

The lipase molecules on the surface of the lipase particles may also be cross-linked, like CLECs (Cross-Linked Enzyme Crystals) or CLEA (Cross-Linked Enzyme Aggregate).

Water-Soluble Film

Water-soluble films, optional ingredients for use therein, and methods of making the same are well known in the art. In one class of embodiments, the water-soluble film includes PVOH. PVOH is a synthetic resin generally prepared by the alcoholysis, usually termed hydrolysis or saponification, of polyvinyl acetate. Fully hydrolyzed PVOH, wherein virtually all the acetate groups have been converted to alcohol groups, is a strongly hydrogen-bonded, highly crystalline polymer which dissolves only in hot water—greater than about 140° F. (60° C.). If a sufficient number of acetate groups are allowed to remain after the hydrolysis of polyvinyl acetate, the PVOH polymer then being known as partially hydrolyzed, it is more weakly hydrogen-bonded and less crystalline and is soluble in cold water—less than about 50° F. (10° C.). An intermediate cold/hot water-soluble film can include, for example, intermediate partially-hydrolyzed PVOH (e.g., with degrees of hydrolysis of about 94% to about 98%), and is readily soluble only in warm water—e.g., rapid dissolution at temperatures of about 40° C. and greater. Both fully and partially hydrolyzed PVOH types are commonly referred to as PVOH homopolymers although the partially hydrolyzed type is technically a vinyl alcohol-vinyl acetate copolymer.

The degree of hydrolysis of the PVOH included in the water-soluble films of the present disclosure can be about 75% to about 99%. As the degree of hydrolysis is reduced, a film made from the resin will have reduced mechanical strength but faster solubility at temperatures below about 20° C. As the degree of hydrolysis increases, a film made from the resin will tend to be mechanically stronger and the thermoformability will tend to decrease. The degree of hydrolysis of the PVOH can be chosen such that the water-solubility of the resin is temperature dependent, and thus the solubility of a film made from the resin, compatibilizing agent, and additional ingredients is also influenced. In one class of embodiments the film is cold water-soluble. A cold water-soluble film, soluble in water at a temperature of less than 10° C., can include PVOH with a degree of hydrolysis in a range of about 75% to about 90%, or in a range of about 80% to about 90%, or in a range of about 85% to about 90%. In another class of embodiments the film is hot water-soluble. A hot water-soluble film, soluble in water at a temperature of at least about 60° C., can include PVOH with a degree of hydrolysis of at least about 98%.

Other film-forming resins for use in addition to or in an alternative to PVOH can include, but are not limited to, modified polyvinyl alcohols, polyacrylates, water-soluble acrylate copolymers, polyacrylates, polyacryamides, polyvinyl pyrrolidone, pullulan, water-soluble natural polymers including, but not limited to, guar gum, xanthan gum, carrageenan, and starch, water-soluble polymer derivatives including, but not limited to, ethoxylated starch and hydroxypropylated starch, poly(sodium acrylamido-2-methylpropane sulfonate), polymonomethylmaleate, copolymers thereof, and combinations of any of the foregoing. In one class of embodiments, the film-forming resin is a terpolymer consisting of vinyl alcohol, vinyl acetate, and sodium acrylamido-2-methylpropanesulfonate. Unexpectedly, water-soluble films based on a vinyl alcohol, vinyl acetate, and sodium acrylamido-2-methylpropanesulfonate terpolymer have demonstrated a high percent recovery of enzyme.

The water-soluble resin can be included in the water-soluble film in any suitable amount, for example an amount in a range of about 35 wt % to about 90 wt %. The preferred weight ratio of the amount of the water-soluble resin as compared to the combined amount of all enzymes, enzyme stabilizers, and secondary additives can be any suitable ratio, for example a ratio in a range of about 0.5 to about 5, or about 1 to 3, or about 1 to 2.

Water-soluble resins for use in the films described herein (including, but not limited to PVOH resins) can be characterized by any suitable viscosity for the desired film properties, optionally a viscosity in a range of about 5.0 to about 30.0 cP, or about 10.0 cP to about 25 cP. The viscosity of a PVOH resin is determined by measuring a freshly made solution using a Brookfield LV type viscometer with UL adapter as described in British Standard EN ISO 15023-2: 2006 Annex E Brookfield Test method. It is international practice to state the viscosity of 4% aqueous polyvinyl alcohol solutions at 20° C. All PVOH viscosities specified herein in cP should be understood to refer to the viscosity of 4% aqueous polyvinyl alcohol solution at 20° C., unless specified otherwise.

It is well known in the art that the viscosity of a PVOH resin is correlated with the weight average molecular weight ($\overline{M}w$) of the same PVOH resin, and often the viscosity is used as a proxy for $\overline{M}w$. Thus, the weight average molecular weight of the water-soluble resin optionally can be in a range of about 35,000 to about 190,000, or about 80,000 to about 160,000. The molecular weight of the resin need only be sufficient to enable it to be molded by suitable techniques to form a thin plastic film.

The water-soluble films according to the present disclosure may include other optional additive ingredients including, but not limited to, plasticizers, surfactants, defoamers, film formers, antiblocking agents, internal release agents, anti-yellowing agents and other functional ingredients, for example in amounts suitable for their intended purpose.

Water is recognized as a very efficient plasticizer for PVOH and other polymers; however, the volatility of water makes its utility limited since polymer films need to have at least some resistance (robustness) to a variety of ambient conditions including low and high relative humidity. Glycerin is much less volatile than water and has been well established as an effective plasticizer for PVOH and other polymers. Glycerin or other such liquid plasticizers by themselves can cause surface "sweating" and greasiness if the level used in the film formulation is too high. This can lead to problems in a film such as unacceptable feel to the hand of the consumer and even blocking of the film on the roll or in stacks of sheets if the sweating is not mitigated in some manner, such as powdering of the surface. This could be characterized as over plasticization. However, if too little plasticizer is added to the film the film may lack sufficient ductility and flexibility for many end uses, for example to be converted into a final use format such as pouches.

Plasticizers for use in water-soluble films of the present disclosure include, but are not limited to, sorbitol, glycerol, diglycerol, propylene glycol, ethylene glycol, diethyleneglycol, triethylene glycol, tetraethyleneglycol, polyethylene glycols up to MW 400, 2 methyl 1,3 propane diol, lactic acid, monoacetin, triacetin, triethyl citrate, 1,3-butanediol, trimethylolpropane (TMP), polyether triol, and combinations thereof. Polyols, as described above, are generally useful as plasticizers. As less plasticizer is used, the film can become more brittle, whereas as more plasticizer is used the film can lose tensile strength. Plasticizers can be included in the water-soluble films in an amount in a range of e.g. about 25 phr to about 50 phr, or from about 30 phr to about 45 phr, or from about 32 phr to about 42 phr.

Surfactants for use in water-soluble films are well known in the art. Optionally, surfactants are included to aid in the dispersion of the resin solution upon casting. Suitable surfactants for water-soluble films of the present disclosure include, but are not limited to, dialkyl sulfosuccinates, lactylated fatty acid esters of glycerol and propylene glycol, lactylic esters of fatty acids, sodium alkyl sulfates, polysorbate 20, polysorbate 60, polysorbate 65, polysorbate 80, alkyl polyethylene glycol ethers, lecithin, acetylated fatty acid esters of glycerol and propylene glycol, sodium lauryl sulfate, acetylated esters of fatty acids, myristyl dimethylamine oxide, trimethyl tallow alkyl ammonium chloride, quaternary ammonium compounds, salts thereof and combinations of any of the forgoing. Thus, surfactants can be included in the water-soluble films in an amount of less than about 2 phr, for example less than about 1 phr, or less than about 0.5 phr, for example.

One type of secondary component contemplated for use is a defoamer. Defoamers can aid in coalescing of foam bubbles. Suitable defoamers for use in water-soluble films according to the present disclosure include, but are not limited to, hydrophobic silicas, for example silicon dioxide or fumed silica in fine particle sizes, including Foam Blast® defoamers available from Emerald Performance Materials, including Foam Blast® 327, Foam Blast® UVD, Foam Blast® 163, Foam Blast® 269, Foam Blast® 338, Foam Blast® 290, Foam Blast® 332, Foam Blast® 349, Foam Blast® 550 and Foam Blast® 339, which are proprietary, non-mineral oil defoamers. In embodiments, defoamers can be used in an amount of 0.5 phr, or less, for example, 0.05 phr, 0.04 phr, 0.03 phr, 0.02 phr, or 0.01 phr. Preferably, significant amounts of silicon dioxide will be avoided, in order to avoid stress whitening.

Processes for making water-soluble articles, including films, include casting, blow-molding, extrusion and blown extrusion, as known in the art. One contemplated class of embodiments is characterized by the water-soluble film described herein being formed by casting, for example, by admixing the ingredients described herein with water to create an aqueous mixture, for example a solution with optionally dispersed solids, applying the mixture to a surface, and drying off water to create a film. Similarly, other compositions can be formed by drying the mixture while it is confined in a desired shape.

In one contemplated class of embodiments, the water-soluble film is formed by casting a water-soluble mixture wherein the water-soluble mixture is prepared according to the steps of:
(a) providing a mixture of water-soluble resin, water, and any optional additives excluding plasticizers;
(b) boiling the mixture for 30 minutes;
(c) degassing the mixture in an oven at a temperature of at least 40° C.; optionally in a range of 40° C. to 70° C., e.g., about 65° C.;
(d) adding one or more enzymes, plasticizer, and additional water to the mixture at a temperature of 65° C. or less; and
(e) stirring the mixture without vortex until the mixture appears substantially uniform in color and consistency; optionally for a time period in a range of 30 minutes to 90 minutes, optionally at least 1 hour; and
(f) casting the mixture promptly after the time period of stirring (e.g., within 4 hours, or 2 hours, or 1 hour).

If the enzyme is added to the mixture too early, e.g., with the secondary additives or resin, the activity of the enzyme may decrease. Without intending to be bound by any particular theory, it is believed that boiling of the mixture with the enzyme leads to the enzyme denaturing and storing in solution for extended periods of time also leads to a reduction in enzyme activity.

In one class of embodiments, high enzyme activity is maintained in the water-soluble films according to the present disclosure by drying the films quickly under moderate to mild conditions. As used herein, drying quickly refers to a drying time of less than 24 hours, optionally less than 12 hours, optionally less than 8 hours, optionally less than 2 hours, optionally less than 1 hour, optionally less than 45 minutes, optionally less than 30 minutes, optionally less than 20 minutes, optionally less than 10 minutes, for example in a range of about 6 minutes to about 10 minutes, or 8 minutes. As used herein, moderate to mild conditions refer to drying temperatures of less than 170° F. (77° C.), optionally in a range of about 150° F. to about 170° F. (about 66° C. to about 77° C.), e.g., 165° F. (74° C.). As the drying temperature increases, the enzymes tend to denature faster, whereas as the drying temperature decreases, the drying time increases, thus exposing the enzymes to solution for an extended period of time.

The film is useful for creating a packet to contain a composition, for example laundry or dishwashing compositions, thereby forming a pouch. The film described herein can also be used to make a packet with two or more compartments made of the same film or in combination with films of other polymeric materials. Additional films can, for example, be obtained by casting, blow-molding, extrusion or blown extrusion of the same or a different polymeric material, as known in the art. In one type of embodiment, the polymers, copolymers or derivatives thereof suitable for use as the additional film are selected from polyvinyl alcohols, polyvinyl pyrrolidone, polyalkylene oxides, polyacrylic acid, cellulose, cellulose ethers, cellulose esters, cellulose amides, polyvinyl acetates, polycarboxylic acids and salts, polyaminoacids or peptides, polyamides, polyacrylamide, copolymers of maleic/acrylic acids, polysaccharides including starch and gelatin, natural gums such as xanthan, and carrageenans. For example, polymers can be selected from polyacrylates and water-soluble acrylate copolymers, methylcellulose, carboxymethylcellulose sodium, dextrin, ethylcellulose, hydroxyethyl cellulose, hydroxypropyl methylcellulose, maltodextrin, polymethacrylates, and combinations thereof, or selected from polyvinyl alcohols, polyvinyl alcohol copolymers and hydroxypropyl methyl cellulose (HPMC), and combinations thereof.

The pouches and/or packets of the present disclosure comprise at least one sealed compartment. Thus the pouches may comprise a single compartment or multiple compartments. The pouches may have regions with and without enzymes. In embodiments including multiple compartments, each compartment may contain identical and/or different compositions. In turn, the compositions may take any suitable form including, but not limited to liquid, solid and combinations thereof (e.g., a solid suspended in a liquid). In some embodiments, the pouches comprises a first, second and third compartment, each of which respectively contains a different first, second and third composition. In some embodiments, the compositions may be visually distinct as described in EP 2258820.

The compartments of multi-compartment pouches and/or packets may be of the same or different size(s) and/or volume(s). The compartments of the present multi-compartment pouches can be separate or conjoined in any suitable manner. In some embodiments, the second and/or third and/or subsequent compartments are superimposed on the first compartment. In one embodiment, the third compartment may be superimposed on the second compartment, which is in turn superimposed on the first compartment in a sandwich configuration. Alternatively the second and third compartments may be superimposed on the first compartment. However it is also equally envisaged that the first, second and optionally third and subsequent compartments may be attached to one another in a side by side relationship. The compartments may be packed in a string, each compartment being individually separable by a perforation line. Hence each compartment may be individually torn-off from the remainder of the string by the end-user.

In some embodiments, multi-compartment pouches and/or packets include three compartments consisting of a large first compartment and two smaller compartments. The second and third smaller compartments are superimposed on the first larger compartment. The size and geometry of the compartments are chosen such that this arrangement is achievable. The geometry of the compartments may be the same or different. In some embodiments the second and optionally third compartment each has a different geometry and shape as compared to the first compartment. In these embodiments, the second and optionally third compartments are arranged in a design on the first compartment. The design may be decorative, educative, or illustrative, for example to illustrate a concept or instruction, and/or used to indicate origin of the product. In some embodiments, the first compartment is the largest compartment having two large faces sealed around the perimeter, and the second compartment is smaller covering less than about 75%, or less than about 50% of the surface area of one face of the first compartment. In embodiments in which there is a third compartment, the aforementioned structure may be the same but the second and third compartments cover less than about 60%, or less than about 50%, or less than about 45% of the surface area of one face of the first compartment.

The pouches and/or packets of the present disclosure may comprise one or more different films. For example, in single compartment embodiments, the packet may be made from one wall that is folded onto itself and sealed at the edges, or alternatively, two walls that are sealed together at the edges. In multiple compartment embodiments, the packet may be made from one or more films such that any given packet compartment may comprise walls made from a single film or multiple films having differing compositions. In one embodiment, a multi-compartment pouch comprises at least three walls: an outer upper wall; an outer lower wall; and a partitioning wall. The outer upper wall and the outer lower wall are generally opposing and form the exterior of the pouch. The partitioning wall is interior to the pouch and is secured to the generally opposing outer walls along a seal line. The partitioning wall separates the interior of the multi-compartment pouch into at least a first compartment and a second compartment. In one class of embodiments, the partitioning wall may be the only enzyme containing film thereby minimizing the exposure of the consumer to the enzymes.

Pouches and packets may be made using any suitable equipment and method. For example, single compartment pouches may be made using vertical form filling, horizontal form filling, or rotary drum filling techniques commonly known in the art. Such processes may be either continuous or intermittent. The film may be dampened, and/or heated to increase the malleability thereof. The method may also involve the use of a vacuum to draw the film into a suitable mold. The vacuum drawing the film into the mold can be applied for about 0.2 to about 5 seconds, or about 0.3 to about 3, or about 0.5 to about 1.5 seconds, once the film is on the horizontal portion of the surface. This vacuum can be such that it provides an under-pressure in a range of 10 mbar to 1000 mbar, or in a range of 100 mbar to 600 mbar, for example.

The molds, in which packets may be made, can have any shape, length, width and depth, depending on the required dimensions of the pouches. The molds may also vary in size and shape from one to another, if desirable. For example, the volume of the final pouches may be about 5 ml to about 300 ml, or about 10 to 150 ml, or about 20 to about 100 ml, and that the mold sizes are adjusted accordingly.

In one embodiment, the packet includes a first and a second sealed compartment. The second compartment is in a generally superposed relationship with the first sealed compartment such that the second sealed compartment and the first sealed compartment share a partitioning wall interior to the pouch.

In one embodiment, the packet including a first and a second compartment further includes a third sealed compartment. The third sealed compartment is in a generally superposed relationship with the first sealed compartment such that the third sealed compartment and the first sealed compartment share a partitioning wall interior to the pouch.

In various embodiments, the first composition and the second composition are selected from one of the following combinations: liquid, liquid; liquid, powder; powder, powder; and powder, liquid.

In various embodiments, the first, second and third compositions are selected from one of the following combinations: solid, liquid, liquid and liquid, liquid, liquid.

In one embodiment, the single compartment or plurality of sealed compartments contains a composition. The plurality of compartments may each contain the same or a different composition. The composition is selected from a liquid, solid or combination thereof.

Heat can be applied to the film in the process commonly known as thermoforming. The heat may be applied using any suitable means. For example, the film may be heated directly by passing it under a heating element or through hot air, prior to feeding it onto a surface or once on a surface. Alternatively, it may be heated indirectly, for example by heating the surface or applying a hot item onto the film. The film can be heated using an infrared light. The film may be heated to a temperature of at least 50° C., for example about 50 to about 150C, about 50 to about 120C, about 60 to about 130C, about 70 to about 120C, or about 60 to about 90° C.

Alternatively, the film can be wetted by any suitable means, for example directly by spraying a wetting agent (including water, a solution of the film composition, a plasticizer for the film composition, or any combination of the foregoing) onto the film, prior to feeding it onto the surface or once on the surface, or indirectly by wetting the surface or by applying a wet item onto the film.

Once a film has been heated and/or wetted, it may be drawn into an appropriate mold, preferably using a vacuum. The film can be thermoformed with a draw ratio of at least about 1.5, for example, and optionally up to a draw ratio of 2, for example. The filling of the molded film can be accomplished by utilizing any suitable means. In some embodiments, the most preferred method will depend on the product form and required speed of filling. In some embodiments, the molded film is filled by in-line filling techniques. The filled, open packets are then closed forming the pouches, using a second film, by any suitable method. This may be accomplished while in horizontal position and in continuous, constant motion. The closing may be accomplished by continuously feeding a second film, preferably water-soluble film, over and onto the open packets and then preferably sealing the first and second film together, typically in the area between the molds and thus between the packets.

Any suitable method of sealing the packet and/or the individual compartments thereof may be utilized. Non-limiting examples of such means include heat sealing, solvent welding, solvent or wet sealing, and combinations thereof. The water-soluble packet and/or the individual compartments thereof can be heat sealed at a temperature of at least 200° F. (93° C.), for example in a range of about 220° F. (about 105° C.) to about 290° F. (about 145° C.), or about 230° F. (about 110° C.) to about 280° F. (about 140° C.). Typically, only the area which is to form the seal is treated with heat or solvent. The heat or solvent can be applied by any method, typically on the closing material, and typically only on the areas which are to form the seal. If solvent or wet sealing or welding is used, it may be preferred that heat is also applied. Preferred wet or solvent sealing/welding methods include selectively applying solvent onto the area between the molds, or on the closing material, by for example, spraying or printing this onto these areas, and then applying pressure onto these areas, to form the seal. Sealing rolls and belts as described above (optionally also providing heat) can be used, for example.

The formed pouches may then be cut by a cutting device. Cutting can be accomplished using any known method. It may be preferred that the cutting is also done in continuous manner, and preferably with constant speed and preferably while in horizontal position. The cutting device can, for example, be a sharp item, or a hot item, or a laser, whereby in the latter cases, the hot item or laser 'burns' through the film/sealing area.

The different compartments of a multi-compartment pouches may be made together in a side-by-side style wherein the resulting, cojoined pouches may or may not be separated by cutting. Alternatively, the compartments can be made separately.

In some embodiments, pouches may be made according to a process including the steps of:
a) forming a first compartment (as described above);
b) forming a recess within some or all of the closed compartment formed in step (a), to generate a second molded compartment superposed above the first compartment;
c) filling and closing the second compartments by means of a third film;
d) sealing the first, second and third films; and
e) cutting the films to produce a multi-compartment pouch.

The recess formed in step (b) may be achieved by applying a vacuum to the compartment prepared in step (a).

In some embodiments, second, and/or third compartment(s) can be made in a separate step and then combined with the first compartment as described in EP 2088187 or WO 2009/152031.

In other embodiments, pouches may be made according to a process including the steps of:
a) forming a first compartment, optionally using heat and/or vacuum, using a first film on a first forming machine;
b) filling the first compartment with a first composition;
c) on a second forming machine, deforming a second film, optionally using heat and vacuum, to make a second and optionally third molded compartment;
d) filling the second and optionally third compartments;
e) sealing the second and optionally third compartment using a third film;
f) placing the sealed second and optionally third compartments onto the first compartment;
g) sealing the first, second and optionally third compartments; and
h) cutting the films to produce a multi-compartment pouch.

The first and second forming machines may be selected based on their suitability to perform the above process. In some embodiments, the first forming machine is preferably a horizontal forming machine, and the second forming machine is preferably a rotary drum forming machine, preferably located above the first forming machine.

It should be understood that by the use of appropriate feed stations, it may be possible to manufacture multi-compartment pouches incorporating a number of different or distinctive compositions and/or different or distinctive liquid, gel or paste compositions.

Processes of Making the Compositions

The compositions of the present invention can be formulated into any suitable form and prepared by any process chosen by the formulator, non-limiting examples of which are described in Applicants' examples and in U.S. Pat. No. 4,990,280; US20030087791A1; US20030087790A1; US20050003983A1; US20040048764A1; U.S. Pat. Nos. 4,762,636; 6,291,412; US20050227891A1; EP1070115A2; U.S. Pat. Nos. 5,879,584; 5,691,297; 5,574,005; 5,569,645; 5,565,422; 5,516,448; 5,489,392; 5,486,303 all of which are incorporated herein by reference. The compositions of the invention or prepared according to the invention comprise cleaning and/or treatment composition including, but not limited to, compositions for treating fabrics, hard surfaces and any other surfaces in the area of fabric and home care, including: air care including air fresheners and scent delivery systems, car care, dishwashing, fabric conditioning (including softening and/or freshening), laundry detergency, laundry and rinse additive and/or care, hard surface cleaning and/or treatment including floor and toilet bowl cleaners, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use: car or carpet shampoos, bathroom cleaners including toilet bowl cleaners; as well as cleaning auxiliaries such as bleach additives and "stain-stick" or pre-treat types, substrate-laden compositions such as dryer added sheets. Preferred are compositions and methods for cleaning and/or treating textiles and/or hard surfaces, most preferably textiles. The compositions are preferably compositions used in a pretreatment step or main wash step of a washing process, most preferably for use in textile washing step.

As used herein, the term "fabric and/or hard surface cleaning and/or treatment composition" is a subset of cleaning and treatment compositions that includes, unless otherwise indicated, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, car or carpet shampoos, bathroom cleaners including toilet bowl cleaners; fabric conditioning compositions including softening and/or freshening that may be in liquid, solid and/or dryer sheet form; as well as cleaning auxiliaries such as bleach additives and "stain-stick" or pre-treat types, substrate-laden compositions such as dryer added sheets. All of such compositions which are applicable may be in standard, concentrated or even highly concentrated form even to the extent that such compositions may in certain aspect be non-aqueous.

Method of Use

The present invention includes a method for cleaning any surface including treating a textile or a hard surface or other surfaces in the field of fabric and/or home care. In one aspect of the invention, the method comprises the step of contacting the surface to be treated in a pre-treatment step or main wash step of a washing process, most preferably for use in a textile washing step or alternatively for use in dishwashing including both manual as well as automated/mechanical dishwashing. In one embodiment of the invention the lipase variant and other components are added sequentially into the method for cleaning and/or treating the surface. Alternatively, the lipase variant and other components are added simultaneously.

As used herein, washing includes but is not limited to, scrubbing, and mechanical agitation. Washing may be conducted with a foam composition as described in WO08/101958 and/or by applying alternating pressure (pressure/vaccum) as an addition or as an alternative to scrubbing and mechanical agitation. Drying of such surfaces or fabrics may be accomplished by any one of the common means employed either in domestic or industrial settings. The cleaning compositions of the present invention are ideally suited for use in laundry as well as dishwashing applications. Accordingly, the present invention includes a method for cleaning an object including but not limiting to fabric, tableware, cutlery and kitchenware. The method comprises the steps of contacting the object to be cleaned with a said cleaning composition comprising at least one embodiment of Applicants' cleaning composition, cleaning additive or mixture thereof. The fabric may comprise most any fabric capable of being laundered in normal consumer or institutional use conditions. The solution may have a pH from 8 to 10.5. The compositions may be employed at concentrations from 500 to 15.000 ppm in solution. The water temperatures typically range from 5° C. to 90° C. The water to fabric ratio is typically from 1:1 to 30:1.

In one aspect the invention relates to a method of using the polypeptide with at least 75% identity to SEQ ID NO: 3 for producing a composition. In one aspect the invention relates to use of the composition for cleaning an object.

In one aspect the invention relates to a method of producing a composition comprising adding the variant. In one aspect the invention relates to a method of producing the composition, comprising adding a polypeptide with at least 75% identity to SEQ ID NO: 3, and a surfactant. In one aspect the invention relates to a method for cleaning a surface, comprising contacting a lipid stain present on the surface to be cleaned with the cleaning composition. In one aspect the invention relates to a method for hydrolyzing a lipid present in a soil and/or a stain on a surface, comprising contacting the soil and/or the stain with the cleaning composition. In one aspect the invention relates to a method of hydrolyzing a lipase substrate comprising contacting said substrate with the variant.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The invention relates to lipase variants that have been modified to contain a disulfide bond or bridge that results in a lower hydrolytic activity of the lipase as compared to the parent lipase. The lipase variant can be activated or reactivated by breaking the disulfide bond and or degrading a peptide attached to the disulfide bond, thus allowing the activated lipase variant to function more effectively. The disulfide bond could be introduced so that a propeptide portion of the lipase variant is linked to the mature part of the lipase variant. The presence of the link and the propeptide portion results in a lower hydrolytic activity of the lipase variant as compared to the parent lipase, see e.g. example 3. This can allow the lipase variant to retain its activity during processing, formulation, transport and storage etc, especially while the lipase variant is in a potentially harsh environment of a detergent composition. The lipase variant can be activated by breaking the disulfide bond, or degrading or removing the propeptide portion, thus allowing the lipase variant to act more effectively on substrates. This effectively retains the activity of the lipase variant ready for when it is needed, reducing or preventing loss of activity which might otherwise occur with the parent lipase during storage etc. This aspect of the invention is applicable to lipases that comprises a propetide or a region corresponding to a propeptide without being limiting such as e.g. Zygomycetes lipases, and in particular to *Rhizomucor miehei* lipase. Examples of useful zygomycetes lipases are those which are derived from or have the sequences of SEQ ID No: 2; SEQ ID No: 8; SEQ ID No: 9; SEQ ID No: 10; SEQ ID No: 11; SEQ ID No: 12; SEQ ID No: 13; SEQ ID No: 14; SEQ ID No: 15; or SEQ ID No: 16.

The invention also relates to the use of a disulfide bond within the mature part of the lipase to achieve the same effect. Some lipases a domain called a lid (or flap), covering the active site in the enzyme's inactive state. Upon activation, the lid changes conformation and moves to expose the active site, which enables substrate access and onset of catalysis. The lipase variant can be modified to contain a disulfide link which affects the ability of the lid to move to expose the active site. In particular, a disulphide bond can be introduced which inhibits the ability of the lid to open. The presence of the link results in a lower hydrolytic activity of the lipase variant as compared to the parent lipase. This can allow the lipase variant to retain its activity during processing, formulation, transport and storage etc, especially while the lipase variant is in a potentially harsh environment of a detergent composition. Upon cleavage of the bond, for example by the introduction of a reducing agent and/or surfactant, the lid can open more easily, and the hydrolytic activity of the lipase variant increases. This effectively retains the activity of the lipase variant ready for when it is needed, reducing or preventing loss of activity which might otherwise occur with the parent lipase during storage etc. This aspect of the invention is applicable to lipases that comprises a lid or a region corresponding to a lid without being limiting such as e.g. *Humicola* lipases, and in particular to *Thermomyces lanuginosus* lipase. Examples of useful *Humicola* lipases are those which are derived from or has the sequence of SEQ ID No: 6.

One enzyme for use in the invention is *Rhizomucor miehei* lipase. The wild type lipase can be used in the formulation of detergent compositions for use in, amongst other things, washing textiles. The environment within a detergent composition can be quite harsh, and can lead to inactivation of components, particularly enzymes including lipases. So, although a lipase may be added to a detergent composition, depending upon the ambient conditions and length of time, the overall activity of the enzyme when the detergent composition is used may be less than the desired level. The present invention addresses this problem by providing the lipase in an inactive, protected form to retain activity of the enzyme ready for when it is needed. In one aspect this can be achieved by providing a lipase variant having a breakable link between the propeptide and the mature peptide components of the enzyme. In other words, the invention relates to the stabilisation and inhibition of a lipase through a bridge stabilised complex between the propeptide and the mature lipase part of the zymogen. This can be achieved by the introduction of an S—S bridge (disulfide bond) into the structure of the propeptide-enzyme-complex. This can be achieved by creating mutations to introduce cysteine in place of the naturally-occurring amino-acid residue. The S—S bridge can stabilise the inhibited complex beyond the stabilisation obtained with covalent bonds to the pro-peptide in the N-terminus of the lipase.

A controlled activation can be obtained by breaking the S—S link and/or by degrading the propeptide portion, for example by the addition of an activator. As defined above, an activator can comprise an enzyme such as a protease, and/or a reducing agent. Preferably, the activator comprises a surfactant and a reducing agent (preferably sulphite). The activation or reactivation of the lipase can be achieved at the moment when the lipase is required to be active. So, for example, a detergent composition may be provided comprising a lipase variant of the invention in the linked, protected, and inactive form. The detergent composition may be mixed with an activating agent, for example in the form of a protease and/or reducing agent, which will then break the S—S link and/or degrade the propeptide portion, releasing the active, mature form of the lipase ready for use. As we will discuss below, this activation of the protected enzyme can be performed in a number of ways.

We will now discuss the invention through some examples.

Variants according the invention have been prepared and tested, showing that the invention can protect the enzyme before use, and then produce an active enzyme when required. RPPI0018 and RPPI0019 are RmL-variants with two different introduced S—S bridges between the propeptide and material protein parts of the lipase. For both the variants, tests have been performed to show that they have little or no wash performance in a controlled test when added as such. Activity assays have been performed, without and with a 15 minute pre-treatment with protease, which showed a transformation from 0 activity to total activation of these variants through incubation with a protease (Savinase). A partial activation of the variants was obtained with similar incubation with reducing agents TCEP and with 2% sulphite. A significant stabilisation during storage in a detergent composition without a protease was observed in tests, example 3. Deferential scanning calorimetry was carried out which showed an 18° C. to 20° C. stabilisation of these variants when compared to wild type RmL. A max Tm of 78° C. to 80° C. and above was measured which reduced only to around 75° C. to 77° C. when incubated with 1 mM LAS.

The following list of lipase variants for use in the invention, with reference to the numbering system for RmL as shown in SEQ ID NO: 2 include the following: L-57C/N120C; L-54C/P101C; A-47C/V102C; A-24C/G104C; P-46C/N186C; A-43C/N186C; T-40C/P182C; T-40C/L216C; T-40C/L239C; D-38C/A212C; P-37C/E240C; P-37C/N246C; E-36C/N246C; E-36C/V249C; A-33C/V249C; M-31C/V249C. Preferred variants include P-46C/N186C (RPPI0019), T-40C/P182C (RPPI0018), L-54C/P101C, A-24C/G104C, and D-38C/A212C.

In use, the protected lipase variants can be packaged in a number of different ways. They could, for example, be provided in packaging that separates the protected enzyme from an activation agent. A user could manipulate the package to cause mixing of the activation agent and the protected enzyme when the enzyme is needed. This could, for example, in the form of a multi-chamber package, with one chamber containing the lipase variant and another chamber containing one or more activation agents. The two chambers are separate initially, but can be caused to be in communication with each other, to allow mixing of the activation agent with the protected enzyme. This may be achieved in the form of a multi chamber package, where externally applied force causes a barrier between the two chambers to break or otherwise be removed, allowing the activation agent to contact the protected enzyme and thus break apart the S—S bridge. This then provides the activated enzyme ready for use.

Another way of achieving the activation of the enzyme is to provide separate compositions, with one composition comprises the protected enzyme, and another composition comprising one or more activators. The two compositions may then be admixed in order to activate the enzyme ready for use. In a preferred embodiment, the compositions are in liquid form.

Preferred activators include protein degrading enzymes such as proteases e.g. Savinase (Novozymes). Preferred activators also include reducing agents such as tris(2-carboxyethyl)phosphine (TCEP) and sodium sulphite.

The invention is further defined in the following paragraphs:

Paragraph 1. A method for generating a preparation of a lipase variant of a parent lipase comprising a step of altering one or more nucleotides in a polynucleotide encoding the parent lipase, wherein the alteration provides at least one disulfide bond and a hydrolytic activity of said lipase variant which is reduced as compared with the hydrolytic activity of the parent lipase.

Paragraph 2. The method according to the previous paragraph wherein the lipase variant has a propeptide and a mature part in which the step of altering one or more nucleotides results in the propeptide and/or the mature part containing a cysteine residue.

Paragraph 3. The method according to the previous paragraph wherein the step of altering one or more nucleotides results in the propeptide and/or the mature part containing two cysteine residues.

Paragraph 4. The method according to paragraph 1 wherein the parent lipase is a zygomycete lipase and/or has at least 50% sequence identity with SEQ ID NO: 2.

Paragraph 5. The method according to any previous paragraphs wherein the parent lipase is a zygomycete lipase having the amino acid sequence of SEQ ID NO: 2; SEQ ID NO: 8; SEQ ID NO: 9; SEQ ID NO: 10; SEQ ID NO: 11; SEQ ID NO: 12; SEQ ID NO: 13; SEQ ID NO: 14; SEQ ID NO: 15; or SEQ ID NO: 16.

Paragraph 6. The method according to any previous paragraphs wherein the step of altering one or more nucleotides comprises a substitution at one or more positions corresponding to positions −57, −54, −47, −46, −43, −40, −38, −37, −36, −33, −31, −24, 101, 102, 104, 120, 182, 186, 212, 216, 239, 240, 246 and 249 of SEQ ID NO: 2.

Paragraph 7. The method according to any previous paragraphs wherein the step of altering one or more nucleotides comprises a substitution at one or more positions corresponding to positions −57, −54, −47, −46, −43, −40, −38, −37, −36, −33, −31, −24, and comprises a substitution at one or more positions corresponding to positions 101, 102, 104, 120, 182, 186, 212, 216, 239, 240, 246 and 249 of SEQ ID NO: 2.

Paragraph 8. The method according to any previous paragraphs wherein the step of altering one or more nucleotides comprises a substitution at one or more residues corresponding to positions selected from L-57C/N120C, L-54C/P101C, A-47C/V102C, A-24C/G104C, P-46C/N186C, A-43C/N186C, T-40C/P182C, T-40C/L216C, T-40C/L239C, D-38C/A212C, P-37C/E240C, P-37C/N246C, E-36C/N246C, E-36C/V249C, A-33C/V249C and M-31C/V249C of SEQ ID NO: 2.

Paragraph 9. A polynucleotide encoding a lipase variant of a parent lipase comprising an alteration at one or more nucleotides, wherein the alteration provides at least one disulfide bond and a hydrolytic activity of said lipase variant which is reduced as compared with the hydrolytic activity of the parent lipase.

Paragraph 10. A polynucleotide obtainable by the method of any of paragraphs 1 to 8.

Paragraph 11. A nucleic acid construct comprising the polynucleotide of any of paragraphs 9-10.

Paragraph 12. An expression vector comprising the polynucleotide of any of paragraphs 9-10.

Paragraph 13. A host cell comprising the polynucleotide of any of paragraphs 9-10.

Paragraph 14. A method for producing a lipase from the polynucleotide of any of paragraphs 9-10 comprising: (a) cultivating the host cell of paragraph 13 under conditions suitable for expression of the lipase variant; and (b) recovering the lipase variant.

Paragraph 15. A lipase variant prepared according to the method of paragraph 14.

Paragraph 16. A lipase variant of a parent lipase comprising an alteration at one or more nucleotides, wherein the alteration provides at least one disulfide bond and a hydrolytic activity of said lipase variant which is reduced as compared with the hydrolytic activity of the parent lipase Paragraph 17. The lipase variant according to any of paragraphs 15-16 comprising a substitution at one or more positions corresponding to positions −57, −54, −47, −46, −43, −40, −38, −37, −36, −33, −31, −24, 101, 102, 104, 120, 182, 186, 212, 216, 239, 240, 246 and 249 of SEQ ID NO: 2.

Paragraph 18. The lipase variant according to any of paragraphs 15-16 comprising a substitution at one or more positions corresponding to −57, −54, −47, −46, −43, −40, −38, −37, −36, −33, −31 and −24, and comprises a substitution at one or more positions corresponding to positions 101, 102, 104, 120, 182, 186, 212, 216, 239, 240, 246 and 249, of SEQ ID NO: 2.

Paragraph 19. The lipase variant according to any of paragraphs 15-16 comprising a substitution at one or more residues corresponding to positions selected from L-57C/N120C, L-54C/P101C, A-47C/V102C, A-24C/G104C, P-46C/N186C, A-43C/N186C, T-40C/P182C, T-40C/L216C, T-40C/L239C, D-38C/A212C, P-37C/E240C, P-37C/N246C, E-36C/N246C, E-36C/V249C, A-33C/V249C and M-31C/V249C of SEQ ID NO: 2.

Paragraph 20. The lipase variant according to any of paragraphs 15-19 wherein the amino acid sequence of said lipase variant has at least 50% sequence identity with SEQ ID NO: 2; SEQ ID NO: 8; SEQ ID NO: 9; SEQ ID NO: 10; SEQ ID NO: 11; SEQ ID NO: 12; SEQ ID NO: 13 SEQ ID NO: 14 SEQ ID NO: 15; or SEQ ID NO: 16.

Paragraph 21. A composition comprising the lipase variant of any of paragraphs 15-20.

Paragraph 22. The composition of paragraph 21 formulated as a regular, compact or concentrated liquid; a gel; a paste; a soap bar; a regular or a compacted powder; a granulated solid; a homogenous or a multilayer tablet with two or more layers (same or different phases); a pouch having one or more compartments; a single or a multi-compartment unit dose form; or any combination thereof.

Paragraph 23. The composition of any of paragraphs 21-22 further comprising an activator.

Paragraph 24. The composition of paragraph 23 wherein the activator is a protease and/or a reducing agent.

Paragraph 25. A method of cleaning comprising contacting a surface or an item with a composition according to any of paragraphs 21-24.

Paragraph 26. A method for increasing the hydrolytic activity of a lipase variant of any of paragraphs 15-20, comprising a step of bringing said lipase variant into contact with an activator.

EXAMPLES

The following examples include variants of *Rhizomucor miehei* lipase (RmL) and *Thermomyces lanuginosus* lipase (TIL). Two such preferred RmL variants are referred to as RPPI0018 (P182C T-40C) and RPPI0019 (N186C P-46C).

SEQ ID No: 1 sets forth the nucleotide sequence of the RmL including the sequence encoding the prepropeptide (underlined) cleaved off:

atg gtt ctc aag cag cgt gca aac tac cta gga ttt ctg att gta ttc ttc acg gcc ttc ctg gtg gaa gcg gta ccc atc aag aga caa tcg aat tcc acg gtc gac agt ctg ccg cct ctc atc ccc tcg aga acc tcg gca cct tca tca tca cca agc aca acc gac cct gaa gct cca gcc atg agt cgc aat gga ccg ctg ccc tcg gat gta gag act aaa tat ggc atg gct ttg aat gct act tcc tat ccg gat tct gtg gtc caa gca atg agc att gat ggt ggt atc cgc gct gcg acc tcg caa gaa atc aat gaa ttg act tat tac act aca cta tct gcc aac tcg tac tgc cgc act gtc att cct gga gct acc tgg gac tgt atc cac tgt gat gca acg gag gat ctc aag att atc aag act tgg agc acg ctc atc tat gat aca aat gca atg gtt gca cgt ggt gac agc gaa aaa act atc tat atc gtt ttc cga ggt tcg agc tct atc cgc aac tgg att gct gat ctc acc ttt gtg cca gtt tca -continued

```
tat cct ccg gtc agt ggt aca aaa gta cac aag gga ttc ctg gac agt tac ggg gaa gtt caa aac gag ctt gtt gct act gtt ctt gat caa ttc aag caa tat cca agc tac aag gtt gct gtt aca ggt cac tca ctc ggt ggt gct act gcg ttg ctt tgc gcc ctg gat ctc tat caa cga gaa gaa gga ctc tca tcc agc aac ttg ttc ctt tac act caa ggt caa cca cgg gta ggc gac cct gcc ttt gcc aac tac gtt gtt agc acc ggc att cct tac agg cgc acg tca aat gaa cga gat atc gtt cct cat ctt cca cct gct gct ttt ggt ttt ctc cac gct ggc gag gag tat tgg att act gac aat agc cca gag act gtt cag gtc tgc aca agc gat ctg gaa acc tct gat tgc tct aac agc att gtt ccc ttc aca agt gtt ctt gac cat ctc tcg tac ttt ggt atc aac aca ggc ctc tgt act
```

SEQ ID No: 2 sets forth the amino acid sequence of the RmL including the preprosequence (underlined) cleaved off:

MVLKQRANYL GFLIVFFTAF LVEAVPIKRQ SNSTVDSLPP
LIPSRTSAPS SSPSTTDPEA PAMSRNGPLP SDVETKYGMA
LNATSYPDSV VQAMSIDGGI RAATSQEINE LTYYTTLSAN
SYCRTVIPGA TWDCIHCDAT EDLKIIKTWS TLIYDTNAMV
ARGDSEKTIY IVFRGSSSIR NWIADLTFVP VSYPPVSGTK
VHKGFLDSYG EVQNELVATV LDQFKQYPSY KVAVTGHSLG
GATALLCALD LYQREEGLSS SNLFLYTQGQ PRVGDPAFAN
YVVSTGIPYR RTVNERDIVP HLPPAAFGFL HAGEEYWITD
NSPETVQVCT SDLETSDCSN SIVPFTSVLD HLSYFGINTG LCT

SEQ ID No: 3 sets forth the amino acid sequence of the RmL mature protein:

SIDGGIRAAT SQEINELTYY TTLSANSYCR TVIPGATWDC
IHCDATEDLK IIKTWSTLIY DTNAMVARGD SEKTIYIVFR
GSSSIRNWIA DLTFVPVSYP PVSGTKVHKG FLDSYGEVQN
ELVATVLDQF KQYPSYKVAV TGHSLGGATA LLCALDLYQR
EEGLSSSNLF LYTQGQPRVG DPAFANYVVS TGIPYRRTVN
ERDIVPHLPP AAFGFLHAGE EYWITDNSPE TVQVCTSDLE
TSDCSNSIVP FTSVLDHLSY FGINTGLCT

SEQ ID No: 4 sets forth the amino acid sequence of the propeptide of RmL:

VPIKRQSNST VDSLPPLIPS RTSAPSSSPS TTDPEAPAMS
RNGPLPSDVE TKYGMALNAT SYPDSVVQAM

SEQ ID No: 5 sets forth the nucleotide sequence of the TIL including the sequence encoding the prepropeptide (underlined) cleaved off:

```
atg agg agc tcc ctt gtg ctg ttc ttt gtc tct gcg tgg acg gcc ttg gcc agt cct att cgt cga gag gtc tcg cag gat ctg ttt aac cag ttc aat ctc ttt gca cag tat tct gca gcc gca tac tgc gga aaa aac aat gat gcc cca gct ggt aca aac att acg tgc acg gga aat gcc tgc ccc gag gta gag aag gcg gat gca acg ttt ctc tac tcg ttt gaa gac tct gga gtg ggc gat gtc acc ggc ttc ctt gct ctc gac aac acg aac aaa ttg atc gtc ctc tct ttc cgt ggc tct cgt tcc ata gag aac tgg atc ggg aat ctt aac ttc gac ttg aaa gaa ata aat gac att tgc tcc ggc tgc agg gga cat gac ggc ttc act tcg tcc tgg agg tct gta gcc gat acg tta agg cag aag gtg gag gat gct gtg agg gag cat ccc gac tat cgc gtg gtg ttt acc gga cat agc ttg ggt ggt gca ttg gca act gtt gcc gga gca gac ctg cgt gga aat ggg tat gat atc gac gtg ttt tca tat ggc gcc ccc cga gtc gga aac agg gct ttt gca gaa ttc ctg acc gta cag acc ggc gga aca ctc tac cgc att acc cac acc aat gat att gtc cct aga ctc ccg ccg cgc gaa ttc ggt tac agc cat tct agc cca gag tac tgg atc aaa tct gga acc ctt gtc ccc gtc acc cga aac gat atc gtg aag ata gaa ggc atc gat gcc acc ggc ggc aat aac cag cct aac att ccg gat atc cct gcg cac cta tgg tac ttc ggg tta att ggg aca tgt ctt tag
```

SEQ ID No: 6 sets forth the amino acid sequence of the TIL including the preprosequence (underlined) cleaved off:

MRSSLVLFFV SAWTALASPI RREVSQDLFN QFNLFAQYSA
AAYCGKNNDA PAGTNITCTG NACPEVEKAD ATFLYSFEDS
GVGDVTGFLA LDNTNKLIVL SFRGSRSIEN WIGNLNFDLK
EINDICSGCR GHDGFTSSWR SVADTLRQKV EDAVREHPDY
RVVFTGHSLG GALATVAGAD LRGNGYDIDV FSYGAPRVGN
RAFAEFLTVQ TGGTLYRITH TNDIVPRLPP REFGYSHSSP
EYWIKSGTLV PVTRNDIVKI EGIDATGGNN QPNIPDIPAH
LWYFGLIGTC L

SEQ ID No: 7 sets forth the amino acid sequence of the TIL mature protein:

```
EVSQDLFNQF NLFAQYSAAA YCGKNNDAPA GTNITCTGNA

CPEVEKADAT FLYSFEDSGV GDVTGFLALD NTNKLIVLSF

RGSRSIENWI GNLNFDLKEI NDICSGCRGH DGFTSSWRSV

ADTLRQKVED AVREHPDYRV VFTGHSLGGA LATVAGADLR

GNGYDIDVFS YGAPRVGNRA FAEFLTVQTG GTLYRITHTN

DIVPRLPPRE FGYSHSSPEY WIKSGTLVPV TRNDIVKIEG

IDATGGNNQP NIPDIPAHLW YFGLIGTCL
```

Description of Construction of RPPI0018 and RPPI0019

The variants of *Rhizomucor miehei* lipase (RmL), RPPI0018 (T-40C P182C) and RPPI0019 (P-46C N186C) were designed with mutations in the pro-peptide region as well as in the mature peptide to study the interaction between the pro-peptide and the mature peptide.

A PCR-based site-directed mutagenesis was carried out to generate these variants with two overlapping primers for each mutation, the forward primer having the desired mutation, in a single PCR reaction. The PCR product was then treated with DpnI restriction enzyme for 6 hours in a PCR machine at 37° C. DpnI digested the methylated or the parental template DNA whereas the newly formed mutated DNA strands that were non-methylated remained intact. The PCR product was then used to transform competent *Escherichia coli* cells. Plasmid DNAs was isolated from single isolated transformants and sent for sequence analysis, which confirmed the presence of the desired mutation.

The sequence confirmed plasmid DNA was transformed in *A. oryzae* ToC1512 by protoplast mode of transformation. The transformants were screened for protein expression in small scale by inoculation of spores in 2 mL expression media (M400) in 96-well culture plates and grown stationary for 4 days at 34° C., after which protein expression was analyzed on SDS-PAGE. The expressing colony was then streaked on COVE-N-agar slants from which shake-flask fermentation was carried out in M400 media in 1 L baffled shake-flasks for 4 days at 34° C., 180 rpm. Protein expression was analyzed on SDS-PAGE. Once expression was confirmed, the fermentation broth was given for protein purification.

Purification of RPPI18 and RPPI19

Prior to purification on Butyl Toyopearl column clarified culture supernatant was made from the *Aspergillus oryzae* broth by vacuum filtration using a combination of Seitz filter (prod. No. K250, PALL India corporation) and WHATMAN glass filter GF/F grade (prod. No. 1825-25, Whatman-GE Healthcare) in a Buchner funnel (prod. No. PW90, J Brand) followed by a sterile filtration using Supor®-200 0.2u filter (prod. No. 60301, PALL corporation) on a vacuum filtration unit (prod. No. 50060, TARSONS).

Butyl Toyopearl column was pre-equilibrated with wash buffer 25 mM HEPES, pH 7.0+1.5 M $(NH_4)_2SO_4$ buffer. To the clarified culture supernatant required quantity of solid $(NH_4)_2SO_4$ was added to make it 1.5M concentration. Precipitates thus formed were removed by filtration (0.45 u). Sample was then applied on a Butyl Toyopearl column (10×200 mm, bed volume 10 mL) at a linear flow rate of 152 cm/hr. The unbound or weakly bound protein was removed by washing the column with wash buffer until OD at 280 nm reaches below 0.1 Absorbance units. The elution of lipase was conducted with 25 mM HEPES, pH 7.0+0.4 M $(NH_4)_2SO_4$.

Pooled Elution fraction from Butyl Toyopearl column was applied on Superdex-75 column (25×450 mm, bed volume 180 mL) pre-equilibrated with 25 mM HEPES, pH 7.0 at linear flow rate of 25 cm/hr. The elution of the protein was done with the same buffer. Purified protein fractions were collected and pooled.

Example 1: Thermostability

The thermostability of RmL Wildtype as well as the RmL variants RPPI0018 and RPPI0019 were determined by Differential Scanning Calorimetry (DSC) using a VP-Capillary Differential Scanning Calorimeter (MicroCal Inc., Piscataway, N.J., USA). The thermal denaturation temperature, Td (° C.), was taken as the top of denaturation peak (major endothermic peak) in thermograms (Cp vs. T) obtained after heating enzyme solutions in buffer (50 mM HEPES; pH8.0; 0.2 mM $CaCl_2$) at a constant programmed heating rate of 200K/hr. Similar experiments were run with either 1 mM LAS (anioninc surfactant) or 0.05 mg/mL Relase (thermostable protease, Novozymes A/S) added to the buffer. Sample- and reference-solutions (approx. 0.2 mL) were loaded into the calorimeter (reference: buffer without enzyme) from storage conditions at 10° C. and thermally pre-equilibrated for approx. 20 minutes at 20° C. prior to DSC scan from 20° C. to 100° C.

The denaturation temperatures (Tm) measured for RmL Wildtype was 59° C. and the Tm for the lipase variants: RPPI0018 and RPPI0019 were 80° C. and 76° C. respectively. The RmL variants have improved stability in comparison with RmL wildtype when tested at corresponding conditions (80° C. and 76° C. vs 59° C.). Furthermore, it was observed when tested by adding detergent composition ingredients such as 1 mM LAS or 0.05 mg/mL Relase that the Tm of the variants were higher than Tm of the RmL wildtype obtained without any detergent composition ingredients added (59OC).

Example 2: Automatic Mechanical Stress Assay (AMSA)

Washing experiments were performed using Automatic Mechanical Stress Assay (AMSA) in order to assess the wash performance in laundry. The AMSA plate has a number of slots for test solutions and a lid firmly squeezing the laundry sample, the textile to be washed against all the slot openings. During the washing time, the plate, test solutions, textile and lid were vigorously shaken to bring the test solution in contact with the textile and apply mechanical stress in a regular, periodic oscillating manner. For further description see WO02/42740 especially the paragraph "Special method embodiments" at page 23-24. The laundry experiments were conducted in Model Detergent B, pH 8 as specified below:

| | |
|---|---|
| Concentration of Detergents/buffers: | 3.3 g/L Detergent 60% surfactant, 50 mM glycine buffer pH 8 |
| Test solution volume: | 160 uL |
| Wash time: | 20 minutes |
| Temperature: | 25° C. |
| Water hardness: | 15° dH |
| Lipase dosage: | 0 ppm or 0.35 ppm |
| Test material: | Cream turmeric stain according to WO06/125437 |

| Ingredient | Amount (wt %) |
| --- | --- |
| NaOH, pellets (>99%) | 1.05 |
| Linear alkylbenzenesulfonic acid (LAS) (97%) | 7.20 |
| Sodium laureth sulfate (SLES) (28%) | 10.58 |
| Soy fatty acid (>90%) | 2.75 |
| Coco fatty acid (>99%) | 2.75 |
| AEO; alcohol ethoxylate with 8 mol EO; Lutensol TO 8 (~100%) | 6.60 |
| Triethanol amine (100%) | 3.33 |
| Na-citrate, dihydrate (100%) | 2.00 |
| DTMPA; diethylenetriaminepentakis(methylene) pentakis(phosphonic acid), heptasodium salt (Dequest 2066 C) (~42% as Na7 salt) | 0.48 |
| MPG (>98%) | 6.00 |
| EtOH, propan-2-ol (90/10%) | 3.00 |
| Glycerol (>99.5) | 1.71 |
| Sodium formate (>95%) | 1.00 |
| PCA (40% as sodium salt) | 0.46 |
| Water up to | 100 |

Final adjustments to the specified pH were done with NaOH or citric acid. Water hardness was adjusted to 15° dH by addition of $CaCl_2$ and $MgCl_2$ ($Ca^{2+}:Mg^{2+}=4:1$) to the test system.

After washing, the textiles were flushed in tap water and excess water was removed from the textiles using filter paper and immediately thereafter the textiles were dried at 100° C. for 10 min.

The wash performance was measured as the color change of the washed soiled textile. The soil was cream mixed with turmeric. Turmeric contains the colorant curcumin, which function as a pH indicator by having pH dependent color change. Lipase activity leads to release of free fatty acids from the cream acylglycerides and this leads to pH decrease and thereby color change of the curcumin pH indicator. Lipase wash performance can therefore be expressed as the extent of color change of light reflected-emitted from the washed soiled textile when illuminated with white light.

Color measurements were made with a professional flat-bed scanner (EPSON EXPRESSION 10000XL, Atea A/S, Lautrupvang 6, 2750 Ballerup, Denmark), which was used to capture an image of the washed soiled textile. To extract a value for the light intensity from the scanned images, 24-bit pixel values from the image were converted into values for red, green and blue (RGB).

Color change due to lipase activity was measured as the increase in the reflection-emitting of green light (G) relative to the sum of reflected-emitted blue (B) and Red® (R) light. The wash performance (RP(Wash)) of a lipase relative to a reference lipase (SEQ ID NO 3) was calculated as: RP(Wash)=(G/(B+R)(tested lipase)−G/(B+R)(no enzyme))/(G/(B+R)(lipase ref.)−G/(B+R)(no enzyme)).

TABLE 1

Wash performance

| Enzyme | RP (wash) |
| --- | --- |
| RmL wt - mature protein | 1.00 |
| RPPI0018 | −0.08 |
| RPPI0019 | 0.00 |

Example 3: The Activation of the RPPI-Variants

Performance i.e. hydrolytic activity was determined at an enzyme concentration of 0.03 mg/mL by measuring the release of 4-methylumbelliferone (4-MU) by purified protein samples, diluted in 0.2M HEPES, pH 8.5 and incubated respectively:

(1) with and without protease: 0.68% (v/v) Savinase® in 50% (w/w) Detergent B at RT for 15 minutes.

(2) with and without reducing agent: 5 uM TRIS(2-carboxyethyl)phosphine (TCEP) at RT for 15 minutes in 0.2M HEPES buffer, pH 8.5.

(3) with and without reducing agent: 2.0% (w/v) sodium sulphite $NaSO_2$ (Sigma-Aldrich 207845) at RT for 15 minutes in 0.2M HEPES buffer, pH 8.5.

(4) with and without reducing agent: 5 uM TRIS(2-carboxyethyl)phosphine (TCEP) in 50% (w/w) Detergent B at RT for 15 minutes in 0.2M HEPES buffer, pH 8.5.

(5) with and without reducing agent: 2.0% (w/v) sodium sulphite $NaSO_2$ (Sigma-Aldrich 207845) in 50% (w/w) Detergent B at RT for 15 minutes in 0.2 M HEPES buffer, pH 8.5.

Cellulose (Avicel) was coated with a mixture of triglyceride and 4-methylumbelliferyl oleate (4-MU oleate) in an initial substrate preparation step. In the assay, the coated cellulose fibers were suspended in a buffer, a detergent solution, and a lipase solution. The lipase activity monitored in the cellulose suspension by measuring the fluorescence of released 4-methylumbelliferone (4-MU) at Ex: 365 nm and Em: 445 nm as a function of time.

Chemicals:

4-methylumbelliferyl oleate (oleic acid 4-methylumbelliferyl ester, Sigma Aldrich 75164); n-Hexane (Sigma-Aldrich 15671); Olive oil (Sigma-Aldrich 0-1514); Cellulose cotton linters, Avicel H-101 (Sigma-Aldrich 11365); HEPES (4-(2-Hydroxyethyl)piperazine-1-ethanesulfonic acid, N-(2-Hydroxyethyl)piperazine-N'-(2-ethanesulfonic acid, Sigma-Aldrich H33759); Calcium chloride dehydrate; Triton™ X-100 (4-(1,1,3,3-Tetramethylbutyl)phenyl-polyethylene glycol, t-Octylphenoxypolyethoxyethanol, Polyethylene glycol tert-octylphenyl etherSigma-Aldrich T9284); 4 mol/L NaOH (Fluka 35274); Model Detergent B; TRIS(2-carboxyethyl)phosphine (TCEP); $NaSO_2$ (Sigma-Aldrich 207845).

HEPES buffer for incubation was based on following stock solution: 1 M HEPES, 5 mM $CaCl_2$, 50 ppm Triton X-100. Adjusted to pH 8.5 with 4 M NaOH.

Coated cellulose fibers were prepared by pipetting 668 uL 4-MU-oleate stock solution (4 mg/mL 4-Methylumbelliferyl oleate in hexane) and 3.03 mL olive oil stock solution into 100 mL hexane in a round bottomed flask for rotational evaporator, and mixed properly before 10 g cellulose fibers was added. The flask was mounted on a rotational evaporator, and hexane was removed by evaporation at reduced pressure and constant mixing (by rotation) to ensure uniformly coating of the substrate on the cellulose. After complete removal of hexane, the coated cellulose fibers were transferred to a brown flask and the material was stored protected from light at −20° C. until use.

The assay was conducted by transferring 180 uL of Substrate suspension to each well in a black micro-well microtiter plate (e.g. Nunclon surface, 96 well black plates with black bottom, NUNC 137101). It is important to keep a constant, thorough mixing of the Substrate suspension when pipetting to ensure that the same amount of coated cellulose fibers are transferred to each well of the microtiter plate.

The assay was started with addition of 20 uL of incubation solution. The enzyme incubation solution should be added immediately after addition of the Detergent working solution (1.835 g Model B Detergent; 100 ml 1 M HEPES buffer, Water hardness was adjusted to 15° dH by addition of $CaCl_2$ and $MgCl_2$ ($Ca^{2+}$:$Mg^{2+}$=4:1) to the test system and finally adjusted to 500 mL with Milli Q water).

The enzyme activity was followed by measuring the fluorescence (kinetic mode) every 30 seconds at Ex: 365 nm and Em: 445 nm from 1 to 6 minutes after enzyme addition. The plate was mixed by shaking for 5 seconds before first measurement but not between the following measurements. The assay was run at room temperature, i.e. approximately at 20° C. The activity was calculated as the slope of a plot of fluorescence versus time (units: RFU/sec, where RFU is the Relative Fluorescence Signal Unit) using the 1-6 minute time window after enzyme addition.

TABLE 2

Effect of protease on lipase activity

| | Incubated with | Average slope (RFU/sec) +/− StE |
|---|---|---|
| RmL WT mature protein | — | 125 +/− 6 |
| RmL WT mature protein | 1.35% Savinase + Model B | 137 +/− 4 |
| RmL WT mature protein + noncovalently bound propeptide | — | 33 +/− 1 |
| RmL WT mature protein + noncovalently bound propeptide | 1.35% Savinase + Model B | 143 +/− 1 |
| RPPI-0018 | — | 0.76 +/− 0.1 |
| RPPI-0018 | 1.35% Savinase + Model B | 186 +/− 14 |
| RPPI-0019 | — | 1.8 +/− 0.1 |
| RPPI-0019 | 1.35% Savinase + Model B | 177 +/− 14 |

TABLE 3

Effect of TCEP on lipase activity

| | Incubated with | Average slope (RFU/sec) +/− StE |
|---|---|---|
| RmL WT mature protein | — | 105 +/− 3 |
| RmL WT mature protein | 5 μM TCEP | 103 +/− 3 |
| RmL WT mature protein + noncovalently bound propeptide | — | 25 +/− 0.5 |
| RmL WT mature protein + noncovalently bound propeptide | 5 μM TCEP | 22 +/− 0.4 |
| RPPI-0018 | — | 0.68 +/− 0.04 |
| RPPI-0018 | 5 μM TCEP | 83 +/− 2 |
| RPPI-0019 | — | 1.4 +/− 0.06 |
| RPPI-0019 | 5 μM TCEP | 54 +/− 2 |

TABLE 4

Effect of $NaSO_2$ on lipase activity Lipase activity

| | Incubated with | Average slope (RFU/sec) +/− StE |
|---|---|---|
| RmL WT mature protein | — | 111 +/− 3 |
| RmL WT mature protein | 2% $NaSO_2$ | 109 +/− 2 |
| RmL WT mature protein + noncovalently bound propeptide | — | 28 +/− 0.5 |
| RmL WT mature protein + noncovalently bound propeptide | 2% $NaSO_2$ | 28 +/− 0.8 |
| RPPI-0018 | — | 0.7 +/− 0.05 |
| RPPI-0018 | 2% $NaSO_2$ | 3 +/− 0.1 |
| RPPI-0019 | — | 1 +/− 0.03 |
| RPPI-0019 | 2% $NaSO_2$ | 3 +/− 0.1 |

TABLE 5

Effect of TCEP/Model Detergent B on lipase activity

| | Incubated with | Average slope (RFU/sec) +/− StE |
|---|---|---|
| RmL WT mature protein | — | 101 +/− 1 |
| RmL WT mature protein | 5 uM TCEP + Model B | 100 +/− 4 |
| RmL WT mature protein + noncovalently bound propeptide | — | 24 +/− 0.3 |
| RmL WT mature protein + noncovalently bound propeptide | 5 uM TCEP + Model B | 66 +/− 2 |
| RPPI-0018 | — | 1.0 +/− 0.02 |
| RPPI-0018 | 5 uM TCEP + Model B | 172 +/− 0.9 |
| RPPI-0019 | — | 1.3 +/− 0.06 |
| RPPI-0019 | 5 uM TCEP + Model B | 140 +/− 0.7 |

TABLE 6

Effect of $NaSO_2$/Model Detergent B on lipase activity

| | Incubated with | Average slope (RFU/sec) +/− StE |
|---|---|---|
| RmL WT mature protein | — | 101 +/− 1 |
| RmL WT mature protein | 2% $NaSO_2$ + Model B | 99 +/− 3 |
| RmL WT mature protein + noncovalently bound propeptide | — | 24 +/− 0.3 |
| RmL WT mature protein + noncovalently bound propeptide | 2% $NaSO_2$ + Model B | 66 +/− 2 |
| RPPI-0018 | — | 1.0 +/− 0.02 |
| RPPI-0018 | 2% $NaSO_2$ + Model B | 61 +/− 0.6 |
| RPPI-0019 | — | 1.3 +/− 0.06 |
| RPPI-0019 | 2% $NaSO_2$ + Model B | 74 +/− 0.8 |

Example 4: Detergent Stability of the RPPI-Variants

Detergent stability was tested by accelerated storage stability test over time. 10 g Model B detergent in closed glass vial with respectively % Model B detergent and 0.76 ug/mL protein sample were incubated at 30° C. for 3 months and residual activity measurements were performed at regular time intervals. For each protein a parallel sample was stored at −18° C. and defrosted before parallel measurements as reference sample.

| Ingredient of Model Detergent B | Amount (wt %) |
|---|---|
| NaOH, pellets (>99%) | 1.05 |
| Linear alkylbenzenesulfonic acid (LAS) (97%) | 7.20 |
| Sodium laureth sulfate (SLES) (28%) | 10.58 |
| Soy fatty acid (>90%) | 2.75 |
| Coco fatty acid (>99%) | 2.75 |
| AEO; alcohol ethoxylate with 8 mol EO; Lutensol TO 8 (~100%) | 6.60 |
| Triethanol amine (100%) | 3.33 |
| Na-citrate, dihydrate (100%) | 2.00 |
| DTMPA; diethylenetriaminepentakis(methylene) pentakis(phosphonic acid), heptasodium salt (Dequest 2066 C) (~42% as Na7 salt) | 0.48 |

-continued

| Ingredient of Model Detergent B | Amount (wt %) |
|---|---|
| MPG (>98%) | 6.00 |
| EtOH, propan-2-ol (90/10%) | 3.00 |
| Glycerol (>99.5) | 1.71 |
| Sodium formate (>95%) | 1.00 |
| PCA (40% as sodium salt) | 0.46 |
| Water up to | 100 |

Performance i.e. hydrolytic activity was determined by measuring the release of 4-methylumbelliferone (4-MU) by stored detergent/protein samples incubated with 1.35% (w/v) Savinase for 15 minutes in 0.2M HEPES buffer, pH 8.5. Cellulose (Avicel) was coated with a mixture of triglyceride and 4-methylumbelliferyl oleate (4-MU oleate) in an initial substrate preparation step. In the assay, the coated cellulose fibers were suspended in a buffer, a detergent solution, and a lipase solution. The lipase activity monitored in the cellulose suspension by measuring the fluorescence of released 4-methylumbelliferone (4-MU) at Ex: 365 nm and Em: 445 nm as a function of time.

Chemicals:

4-methylumbelliferyl oleate (oleic acid 4-methylumbelliferyl ester, Sigma Aldrich 75164); n-Hexane (Sigma-Aldrich 15671); Olive oil (Sigma-Aldrich 0-1514); Cellulose cotton linters, Avicel H-101 (Sigma-Aldrich 11365); HEPES (4-(2-Hydroxyethyl)piperazine-1-ethanesulfonic acid, N-(2-Hydroxyethyl)piperazine-N'-(2-ethanesulfonic acid, Sigma-Aldrich H33759); Calcium chloride dehydrate; Triton™ X-100 (4-(1,1,3,3-Tetramethylbutyl)phenyl-polyethylene glycol, t-Octylphenoxypolyethoxyethanol, Polyethylene glycol tert-octylphenyl etherSigma-Aldrich T9284); 4 mol/L NaOH (Fluka 35274); Model Detergent B.

HEPES buffer for incubation was based on following stock solution: 1M HEPES, 5 mM $CaCl_2$, 50 ppm Triton X-100. Adjusted to pH 8.5 with 4M NaOH.

Coated cellulose fibers were prepared by pipetting 668 uL 4-MU-oleate stock solution (4 mg/mL 4-Methylumbelliferyl oleate in hexane) and 3.03 mL olive oil stock solution into 100 mL hexane in a round bottomed flask for rotational evaporator, and mixed properly before 10 g cellulose fibers was added. The flask was mounted on a rotational evaporator, and hexane was removed by evaporation at reduced pressure and constant mixing (by rotation) to ensure uniformly coating of the substrate on the cellulose. After complete removal of hexane, the coated cellulose fibers were transferred to a brown flask and the material was stored protected from light at −20° C. until use.

The assay was conducted by transferring 180 uL of Substrate suspension to each well in a black micro-well microtiter plate (e.g. Nunclon surface, 96 well black plates with black bottom, NUNC 137101). It is important to keep a constant, thorough mixing of the Substrate suspension when pipetting to ensure that the same amount of coated cellulose fibers are transferred to each well of the microtiter plate.

The assay was started with addition of 20 uL of incubation solution. The enzyme incubation solution should be added immediately after addition of the Detergent working solution (1.835 g Model Detergent B; 100 mL 1M HEPES buffer, Water hardness was adjusted to 15° dH by addition of $CaCl_2$ and $MgCl_2$ ($Ca^{2+}$:$Mg^{2+}$=4:1) to the test system and finally adjusted to 500 mL with Milli Q water). For the blank, 20 uL Lipase incubation buffer was added.

The enzyme activity was followed by measuring the fluorescence (kinetic mode) every 30 seconds at Ex: 365 nm and Em: 445 nm from 1 to 6 minutes after enzyme addition. The plate was mixed by shaking for 5 seconds before first measurement but not between the following measurements. The assay was run at room temperature, i.e. approximately at 20° C.

The activity was calculated as the slope of a plot of fluorescence versus time (units: RFU/sec, where RFU is the Relative Fluorescence Signal Unit) using the 1-6 minute time window after enzyme addition. Residual activity was calculated by reference to a parallel measured sample stored at the same intervals at −18° C. and defrosted before measurements.

Half life were calculated based on the residual activities (RA) at time "t" via the following formula:

$$t_{1/2} = t * \ln(2)/\ln(RA_o/Ra_t)$$

TABLE 7

Half life of Lipase

| Lipase | Time (days) |
|---|---|
| Lipex | 38 |
| RmL wt | 3 |
| RPPI-0018 | 55 |
| RPPI-0019 | 79 |

Example 5: TLL-Variant

Lipases (EC 3.1.1.3) represent a class of carboxyl ester hydrolases that are able to act on water-insoluble substrates. In order to create an intrinsic switch controlling both enzymatic activity and binding in Thermomyces lanuginosus lipase (TIL) two cysteine residues were engineered into the protein backbone at sites 255 and 86. Investigation of the structural characteristics associated with lipase activation suggests that the variant is locked in a pre-activated state. Control of enzymatic activity and binding was demonstrated on substrate emulsions and natural lipid layers of olive oil and lard with and without reducing agent. The locked lipase displayed very low enzymatic activity (~10%) compared to wild-type. Upon release of the lipase lock, enzymatic activity was fully restored towards substrate emulsions and pNP-esters embedded in lipid layers of olive oil and lard. Furthermore, only 10% binding was observed for the locked lipase to natural lipid substrates, but upon adding reducing agent, binding was restored. This was supported by QCM-D measurements that revealed a seven-fold increase in binding rate for the un-locked lipase.

Triacylglycerol hydrolases (lipases) commonly contain several disulfide bonds to enable high thermal and kinetic stability in oxidative environments making them attractive industrial biocatalysts. The enzyme from Thermomyces lanuginosus (TIL) hydrolyzes triglycerides at the water-lipid interface and the wild-type contains three disulfide bonds, C22-C268, C14-C107, C36-C41. The activity of TIL and related lipases is low on water soluble, monomeric substrates in homogenous aqueous solution. However, as the substrate reaches its critical micelle concentration the lipase is presented to a surface enabling a many-fold increase in hydrolytic activity. This phenomenon is referred to as "interfacial activation" and besides an aggregation of the substrate it involves a structural change in the enzyme itself. More specifically, the structural change represents a rearrangement of an α-helical domain called the lid (or flap), covering the active site in the enzyme's inactive state. Upon activation, the lid changes conformation in a rigid body hinge-type movement, exposing the active site triad His258, Asp201 and Ser146, which enables substrate access and onset of catalysis. The lid is highly amphipathic, containing a distinctive distribution of hydrophobic and hydrophilic residues. In the closed state, hydrophilic residues are exposed at the surface of the protein making favorable interactions with the polar solvent. As the lipase encounters a lipid interface the lid opens and the hydrophobic residues in the lid become exposed and serve as "lipid anchors" positioning the enzyme correctly for catalysis upon substrate binding. Overall, the event of lid-opening results in the exposure of a combined ~750 Å$^2$ hydrophobic surface area a transition which becomes energetically feasible at the water-lipid interface.

A variant (TIL_locked) was designed to contain an intrinsic activity-switch by locking the lid in a closed conformation through the incorporation of two cysteine residues into the protein backbone enabling the formation of a disulfide bond. Successful formation of the intrinsic switch was confirmed in the crystal structure of the variant, which revealed a closed and somewhat strained lid conformation. To assess the impact of this strained conformation on protein stability, a thermal melt assay was used to show that thermo-stability of TIL_locked is decreased compared to wild-type. Although the lid is closed, investigation of structural characteristics around the lid-region suggests that TIL_locked rests in a pre-activated state. The forced closed structure of the variant appears to cause structural instability in the protein backbone as indicated by its increased temperature factors.

The impact of the disulfide bond on enzymatic activity was assessed on short, medium and long-chain ester substrates emulsified in non-ionic surfactant or embedded in lipid layers of rendered porcine fat and olive oil. Furthermore, the lid's role in interfacial binding to natural substrates and hydrophobic surfaces was investigated using a micro-titer plate set-up and QCM-D analysis, respectively.

Materials.

Unless otherwise stated, all reagents and biochemical supplies were purchased from Sigma Aldrich and affiliates.

Engineering and Nomenclature of Lipase Variants.

An intrinsic activity switch was designed into TIL by making single site mutations I86C and I255C enabling disulfide bond formation locking the lipase lid in its closed state. This variant is referred to as TIL_locked. In addition, single cysteine variant controls, C86 (TIL_C86) and C255 (TIL_C255) were made.

Variant Construction, Transformation and Screening.

The variants were created by single site mutagenesis. DNA was sequenced across the whole gene and transformed into *Aspergillus oryzae* strain and fermented according to previous methods. Protoplasts were stored at −80° C. and thawed when needed. Expression was verified by running SDS-page analysis SimplyBlue Safestain (Life Technologies, catalog no. LC6065). Variant screening was carried out for successfully transformed *Aspergillus oryzae* strains using a standard pNP-valerate activity assay.

Protein Purification.

Fermentation broths were sterile filtered using filter units (Nalgene) with appropriate filters (CAT No.: 1820-090, WHATMAN). NaCl was added to filtered supernatant to a final concentration of 1M. The protein purifications were carried out using an ÄKTA Prime (Amersham Biosciences) according to a previous protocol. Variants were purified to a high degree with no observable contaminations verified by SDS-page using Simply Blue Safestain (Life Technologies, catalog no., LC6065). All samples were buffer-exchanged and concentrated in 50 mM MOPS pH 7.5 using centrifugal filter units (Ultracel-IOK, Millipore). Purification of the control C86 variant failed, which was ascribed to low expression yields and high degree of binding to the column during purification.

Thermal Stability.

SYPRO Orange™ (SO) (CAT # S5692, 5000× stock concentrate) was diluted 250× in 50 mM MOPS, pH 7.5. Protein samples were diluted to 0.1 mg/ml. 15 µL of SO and protein solution was added to a final volume of 30 µL to a white 96 well MTP (Eurogentec RT-PL96-AFW), reaching a final protein concentration of 0.1 mg/ml (3 µM). The plate was sealed with an optical PCR seal (Eurogentec RT-OPSL 100). Melting curves for each variant were determined (StepOnePlus Real Time PCR System, Applied Biosystems) running a temperature gradient from 25° C. to 96° C. at a scan-rate of 76° C. pr/hr with an initial 15 minute reaction time at 25° C.

pNP-Ester Emulsion Assay.

The activity towards short and medium chain pNP-ester substrates, pNP-butyrate and pNP-decanoate, respectively, was determined in Substrate buffer (50 mM Tris; 10 mM CaCl$_2$; 0.4% Triton X-100 (CMC is 0.015% (v/v) (20))). Tris(2-Carboxyethyl)phosphine (TCEP) was added as reducing agent in the concentration range of 0 to 10 mM. 10 uL enzyme solution was mixed with 1 L substrate buffer. The increase in absorbance at 405 nm due to released pNP-moeity was measured over 5 minutes and specific activity was determined from steepest slope. The final lipase concentration was 2 ug/mL.

Lipase Activity Assay.

Lipase activity was determined according to a previous protocol. Two sets of substrate-coated 96 well micro-titer assay plates were made 1) olive oil+pNP-decanoate and 2) rendered porcine fat (lard)+pNP-palmitate, respectively (in a 1:1 molar ratio). 190 uL buffer (100 mM Tris pH 7, 8 or 9; 2 mM CaCl$_2$; with or without 5 mM TCEP) was added to 10 uL protein sample (50 ug/mL) in non-binding plates (Corning) to minimize unspecific adsorption of lipase to the well surface. Plates were subsequently incubated for 10 minutes at room temperature. Using a multi-pipette (Rainin), 150 uL was transferred to the assay plate and the increase in absorbance at 405 nm due to released pNP-moiety was measured over 10 minutes and the activity was determined from steepest slope.

Binding to Natural, Triglyceride Substrates.

Differences in binding to lipid layers of natural substrates e.g. olive oil and lard were investigated in a set-up similar to the lipase assay described above, but without pNP-substrate. Samples were diluted to 50 g/mL in 25 mM MOPS pH 7.5. 190 µL buffer (100 mM Tris pH 8+2 mM CaCl$_2$) with and without 1 mM TCEP were added to 10 µL sample in a non-binding micro-titer plate (Corning). After incubation for 10 minutes at room temperature, 150 µL of the sample volume was added to a micro-titer plate coated with 100 nmol olive oil or lard. Binding of lipase to the olive or lard lipid surfaces was determined by the residual activity measured in the supernatant over time (between 2-40 minutes). 20 µL supernatant was assayed in a 100 µL 50 mM Tris pH 75+0.4% Triton X-100+10 mM CaCl$_2$ reaction buffer calculating activity from the initial rate of pNP-butyrate hydrolysis at 405 nm.

Intact Molecular Weight Analysis.

This was determined for variant TIL_locked by LC-ESI-MS analysis using a MAXIS II electrospray mass spectrometer (Bruker Daltonik GmbH, Bremen, Del.). All samples were diluted to ~0.5 mg/mL in milliQ water. The intact molecular weights were determined for untreated samples and samples treated with 1 mM TCEP. Samples were incubated for 30 minutes before being applied to an Aeris Widepore C4 column (Phenomenex), washed and eluted running an acetonitrile linear gradient and introduced to the electrospray source with a flow of 300 mL/min by an Ultimate 3000 LC system (Dionex). Data analysis was performed with DataAnalysis version 4.2 (Bruker Daltonik GmbH, Bremen, Del.).

Steady State Fluorescence Spectroscopy.

Intrinsic tryptophan fluorescence emission spectra were recorded on a fluorescence spectrometer at room temperature (PerkinElmer, LS50B) in a quartz cuvette (Hellma QS 105.250). Emission was detected between 310-650 nm with excitation at 295 nm. Excitation and emission slit-widths were 4 nm and 12 nm, respectively. The scan-rate was 50 nm/min and an average of two consecutive measurements were taken. Emission spectra were measured in two different buffers e.g. A) 25 mM MOPS pH 7.5 and B) 25 mM MOPS pH 7.5+0.4% (v/v) Triton X-100+1 mM TCEP. Note, the Triton X-100 used (Cas. No. 93422) is a reduced form, suitable for fluorescence measurements with approximately the same CMC as the oxidized Triton X-100 (0.25 mM vs. 0.22 mM, respectively (21)). Changes in fluorescence emission intensity over time were measured by conducting emission scans every 4 minutes for 30 minutes. Final scans were taken after 60 minutes.

QCM-D Analysis of Lipase Binding.

Lipase binding experiments were carried out on a E4 quartz crystal microbalance with dissipation instrument (QCM-D (Q-Sense, Sweden)) with temperature control and a peristaltic pump ensuring controlled flow rate. Binding was carried out on standard hydrophobic surfaces, created as alkanethiol ($(HS(CH_2)_{15}CH_3)$) surface assembled monolayer (SAM) on the Au sensor crystals. The buffer used for these experiments was a 50 mM HEPES (pH 7.5), 100 mM NaCl, 1 mM $CaCl_2$ made with MilliQ water subsequently filtered (0.22 µm) and degassed. In this study we monitored lipase binding at 5 µM recording frequency and dissipation changes for 5 harmonics (overtones n=3, 5, 7, 9 & 11). For all samples, the values of ΔF for all overtones were similar and with small dissipation values, thus, the adsorbed protein mass can be calculated according to the Sauerbrey equation, converting ΔF into mass in $ng/cm^2$. Temperature was maintained at 22° C. and raw data were analyzed with Q-tools software and fitted for kinetics with single exponential decay function using Igor Pro (Wavemetrics Inc.).

Crystallization and Data Collection.

The protein was EndoH treated prior to crystallization using a deglycosylation kit from New England BioLabs (catalogue number P0702L). The protein to EndoH ratio was 10:1, and was incubated at 37° C. overnight in the presence of G5 reaction buffer (50 mM sodium citrate pH 5.5). Initial crystallization screening was carried out using sitting-drop vapor-diffusion with drops set up using a Mosquito Crystal liquid handling robot (TTP LabTech, UK) with 150 nl protein solution plus 150 nl reservoir solution in 96-well format plates (MRC 2-well crystallization microplate, Swissci, Switzerland) equilibrated against 54 µl reservoir solution. Crystallization trays were placed in a Rigaku Minstrel HT-UV imaging system for storage and inspection. Experiments were carried out at two temperatures, 4° C. and 20° C., with a number of commercial screens. The best diffraction quality crystals were obtained at 20° C. in JCSG AI (50% PEG400, 0.2M lithium sulfate, 0.1M Na-acetate pH 4.5). Data to 1.8 Å were collected at the Diamond Light Source beamline 104.

Structure Solution and Refinement.

All computations were carried out using programs from the CCP4 suite unless otherwise stated. The data were processed with XDS. The space group was P43212; a=b=90.48 Å; c=160.46 Å. The structure was solved by MOLREP with the structure of wild-type *T. lanuginosus* lipase (PDB entry; 1DT3) as a search model. The structure was refined using REFMAC, iterated by manual model building/correction in COOT and validated using MOL-PROBITY.

The activity towards pNP-decanoate and pNP-palmitate embedded in a lipid layer of olive oil and lard, respectively, was determined as previously described. In the absence of reducing agent, activity of TIL_locked was very low (2 umol/min/mg and 0.5 µmol/min/mg). Upon adding TCEP to the buffer, enzymatic activity of TIL_locked increased nearly 10-fold indicating full recovery of enzymatic activity compared to wild-type and the single cysteine variant, TIL_C255. Importantly, these results clearly demonstrate the key role of the lid in governing enzymatic activity and interfacial activation as supported by previous studies.

Time Dependent Un-Locking of Locked TIL Observed Using Intrinsic Tryptophan Fluorescence.

As shown previously, Trp89 in the lid of TIL is responsible for more than 60% of the protein's total fluorescence emission. Accordingly, we measured the steady state fluorescence emission spectra of TIL and TIL_locked to investigate the microenvironment of around Trp89. In buffer alone (no surfactant or reducing agent) the Trp fluorescence emission spectrum for TIL_locked was slightly blue-shifted with an emission maximum at 336 nm compared to 339 nm for wild-type. In addition, the fluorescence intensity was quenched (~30%). Thiol groups and disulfide bonds act as strong quenchers of tryptophan and tyrosine fluorescence in proteins. The strong degree of quenching is believed to be from the successfully formed disulfide bond. In order to investigate lid-opening (activation) of TIL_locked the fluorescence emission spectra was measured over time in the buffer used in the activity assay containing (FIG. 3). As the detergent concentration in this buffer was several fold higher than the CMC (~0.015% v/v) the emission spectrum of wild-type likely represented the Trp environment of an open lid conformation in accordance with previous studies.

A substantial increase in fluorescence intensity was observed agreeing well with previous studies showing that the quantum yield of Trp in TIL increases in micellar solutions. The degree of intrinsic Trp quenching (~30%) was unchanged in this buffer indicating that the disulfide bond was unaffected by the presence of detergent micelles. In order to measure lid-opening over time for TIL_locked, a reducing agent was added and emission spectra were taken over the course of 60 minutes. The fluorescence emission spectrum underwent a red-shift and an increase in fluorescence intensity over time reaching the same fluorescence intensity as wild-type after 60 minutes of incubation at room temperature.

The binding of TIL and TIL_locked to lipid surfaces of olive oil and lard was investigated by measuring the residual activity in the supernatant as a function of time at pH 8 in the absence of reducing agent. For TIL the fraction of bound molecules reached ~50% after 40 minutes on both olive oil and lard with and without TCEP in the buffer solution. For untreated TIL_locked the bound fraction was very low on olive oil and lard (~10%) after 40 minutes of incubation.

However, as TCEP was added to the buffer, TIL_locked displayed binding profiles similar to wild-type on both lipid substrates with ~50% bound fraction after 40 minutes.

TABLE 8

Specific activity towards pNP-decanoate by TIL and the TIL variant TIL_locked in the presence of various concentrations of TCEP.

| TCEP (mM) | TIL Specific activity (umol/min/mg) | TIL stdev | TIL_locked specific activity (umol/min/mg) | TIL_locked stdev |
|---|---|---|---|---|
| 0.00 | 206.31 | 19.43 | 7.28 | 1.06 |
| 0.16 | 221.03 | 9.33 | 16.26 | 2.65 |
| 0.31 | 216.23 | 6.43 | 33.08 | 10.44 |
| 0.63 | 177.78 | 9.52 | 49.42 | 1.60 |
| 1.25 | 197.23 | 12.36 | 67.67 | 0.18 |
| 2.50 | 204.97 | 12.58 | 105.49 | 6.30 |
| 5.00 | 196.84 | 13.91 | 134.89 | 2.16 |
| 10.00 | 151.92 | 16.19 | 176.18 | 21.96 |

TABLE 9

Specific activity towards pNP-butyrate by TIL and the TIL variant TIL_locked in the presence of various concentrations of TCEP.

| TCEP (mM) | TIL Specific activity (umol/min/mg) | TIL stdev | TIL_locked Specific activity (umol/min/mg) | TIL_locked stdev |
|---|---|---|---|---|
| 0.00 | 90.05 | 5.42 | 9.03 | 0.77 |
| 0.16 | 76.18 | 0.63 | 15.21 | 1.10 |
| 0.31 | 77.54 | 2.45 | 22.31 | 0.86 |
| 0.63 | 85.83 | 4.76 | 35.24 | 1.38 |
| 1.25 | 63.71 | 3.25 | 39.12 | 3.35 |
| 2.50 | 79.31 | 0.44 | 43.61 | 0.11 |
| 5.00 | 66.68 | 4.74 | 86.36 | 6.04 |

TABLE 10

Specific activity towards pNP-decanoate and pNP-butyrate by TIL and the TIL variant TIL_locked in the presence or absence of 5 mM dithiothreitol (DTT) as reducing agent.

| | pNP-decanoate | | pNP-butyrate | |
|---|---|---|---|---|
| | Specific activity (umol/min/mg) | stdev | Specific activity (umol/min/mg) | stdev |
| 0 mM DTT | | | | |
| TIL | 230.46 | 17.07 | 64.48 | 5.24 |
| TIL_locked | 7.28 | 0.62 | 8.43 | 1.17 |
| 5 mM DTT | | | | |
| TIL | 219.38 | 38.64 | 58.82 | 1.91 |
| TIL_locked | 256.99 | 31.90 | 156.02 | 13.90 |

TABLE 11

Lipase activity was determined towards the substrates pNP-decanoate or pNP-palmitate embedded in a lipid layer of olive oil or porcine fat (lard), respectively.

| | pNP-decanoate | | pNP-palmitate | |
|---|---|---|---|---|
| 0 mM TCEP | specific activity umol/min/mg | stdev | specific activity umol/min/mg | stdev |
| TIL | 21.68 | 0.64 | 5.65 | 1.54 |
| TIL_locked | 1.85 | 0.43 | 0.50 | 0.11 |
| 5 mM TCEP | Specific activity (umol/min/mg) | stdev | Specific activity (umol/min/mg) | stdev |
| TIL | 19.61 | 1.40 | 6.49 | 0.81 |
| TIL_locked | 15.89 | 0.89 | 5.96 | 0.58 |

The invention claimed is:

1. A method for obtaining a lipase variant of a parent lipase, comprising introducing into a parent lipase an alteration at one or more positions of the parent lipase, wherein the alteration at the one or more positions provides at least one disulfide bond and wherein hydrolytic activity of the lipase variant is reduced as compared to hydrolytic activity of the parent lipase,
   wherein the alteration is selected from one or more amino acid substitutions selected from the group consisting of L57C/N120C, L54C/P101C, A47C/V102C, S24C/G104C, P46C/N186C, S43C/N186C, T40C/P182C, T40C/L216C, T40C/L239C, D38C/A212C, P37C/E240C, P37C/N246C, E36C/N246C, E36C/V249C, A33C/V249C and S31C/V249C, wherein the position corresponds to the positions of SEQ ID NO: 2
   and wherein the amino acid sequence of the lipase variant has at least 90% sequence identity with SEQ ID NO: 2.

2. The method according to claim 1, wherein the lipase variant has a propeptide and a mature polypeptide.

3. The method according to claim 1, wherein the parent lipase has at least 95% sequence identity with SEQ ID NO: 2.

4. The method according to claim 1, wherein the parent lipase is a zygomycete lipase having an amino acid sequence of SEQ ID NO: 2.

5. A lipase variant of a parent lipase, comprising an alteration at one or more positions compared to the parent lipase, wherein the alteration provides at least one disulfide bond and wherein hydrolytic activity of said lipase variant is reduced as compared with hydrolytic activity of the parent lipase,
   wherein the variant comprises one or more amino acid substitutions selected from the group consisting of L57C/N120C, L54C/P101C, A47C/V102C, S24C/G104C, P46C/N186C, S43C/N186C, T40C/P182C, T40C/L216C, T40C/L239C, D38C/A212C, P37C/E240C, P37C/N246C, E36C/N246C, E36C/V249C, A33C/V249C and S31C/V249C, wherein the positions correspond to the positions of SEQ ID NO: 2,
   and wherein the amino acid sequence of the lipase variant has at least 90% sequence identity with SEQ ID NO: 2.

6. A composition comprising the lipase variant of claim 5.

7. The composition according to claim 6, further comprising an activator, wherein the activator is a protease or a reducing agent.

8. A method for increasing hydrolytic activity of the lipase variant of claim 5, comprising a step of bringing said lipase variant into contact with an activator.

9. The lipase variant of claim 5, comprising one or more amino acid substitutions selected from the group consisting of P-46C/N186C, T-40C/P182C, L-54C/P101C, A-24C/G104C, and D-38C/A212C wherein the positions correspond to the positions of SEQ ID NO: 2.

10. The lipase variant of claim 5, having at least 95% sequence identity with SEQ ID NO: 2.

11. The lipase variant of claim 5, having at least 97% sequence identity with SEQ ID NO: 2.

12. The lipase variant of claim 5, having at least 98% sequence identity with SEQ ID NO: 2.

13. The lipase variant of claim 5, having at least 99% sequence identity with SEQ ID NO: 2.

14. The composition of claim 6, formulated as a regular, compact or concentrated liquid; a gel; a paste; a soap bar; a regular or a compacted powder; a granulated solid; a homogenous or a multilayer tablet with two or more layers (same or different phases); a pouch having one or more compartments; a single or a multi-compartment unit dose form; or any combination thereof.

15. A method of cleaning comprising contacting a surface or an item with a composition according to claim 6.

* * * * *